United States Patent
Desai et al.

(10) Patent No.: US 8,546,400 B2
(45) Date of Patent: Oct. 1, 2013

(54) 1,3-OXAZOLE-4-CARBOXAMIDES, 1,3-THIAZOLE-4-CARBOXAMIDES, AND 1,3-IMIDAZOLE-D-CARBOXAMIDES AS INHIBITORS OF CYCLIN DEPENDENT KINASES

(71) Applicant: Neosome Life Sciences, LLC, Bedford, MA (US)

(72) Inventors: Laxman S. Desai, Brookline, MA (US); Srinivas Chittaboina, Woburn, MA (US)

(73) Assignee: Neosome Life Sciences, LLC, Bedford, MA (US)

( * ) Notice: Subject to any disclaimer, the term of this patent is extended or adjusted under 35 U.S.C. 154(b) by 0 days.

(21) Appl. No.: 13/737,328

(22) Filed: Jan. 9, 2013

(65) Prior Publication Data
US 2013/0184288 A1    Jul. 18, 2013

Related U.S. Application Data

(62) Division of application No. 13/478,376, filed on May 23, 2012.

(60) Provisional application No. 61/490,789, filed on May 27, 2011.

(51) Int. Cl.
| | | |
|---|---|---|
| C07D 263/48 | (2006.01) |
| C07D 263/32 | (2006.01) |
| C07D 417/14 | (2006.01) |
| C07D 277/593 | (2006.01) |
| A61K 31/421 | (2006.01) |
| A61K 31/4178 | (2006.01) |
| A61K 31/426 | (2006.01) |
| A61K 31/427 | (2006.01) |
| A61P 35/00 | (2006.01) |
| A61P 1/16 | (2006.01) |
| A61P 9/10 | (2006.01) |
| A61P 37/06 | (2006.01) |

(52) U.S. Cl.
USPC ...... 514/252.19; 514/377; 544/295; 548/234; 548/198; 548/236; 548/338.1

(58) Field of Classification Search
CPC . C07D 277/593; C07D 263/32; C07D 239/20
USPC ............ 544/298–335; 548/100–346.1
See application file for complete search history.

(56) References Cited

U.S. PATENT DOCUMENTS

| | | | |
|---|---|---|---|
| 7,189,712 B2 * | 3/2007 | Brown et al. | 514/227.8 |
| 7,718,676 B2 * | 5/2010 | Moussy et al. | 514/340 |
| 2008/0207572 A1 * | 8/2008 | Moussy et al. | 514/171 |
| 2010/0113471 A1 * | 5/2010 | Moussy et al. | 514/253.1 |

FOREIGN PATENT DOCUMENTS

| | | | |
|---|---|---|---|
| WO | WO 9846582 A1 | * | 10/1998 |
| WO | WO 2009147188 A1 | * | 12/2009 |
| WO | WO 2010078408 A1 | * | 7/2010 |

OTHER PUBLICATIONS

Dhanak et al. "Derivatives of Potent and Selective Phenylalanine Derived CCR3 Recepter Antagonists. Part 2." Bioorg. Med. Chem. Lett. 2001, 11, 1445-1450.*

* cited by examiner

*Primary Examiner* — Joseph K. McKane
*Assistant Examiner* — Amanda L Aguirre
(74) *Attorney, Agent, or Firm* — Foley Hoag LLP

(57) ABSTRACT

Oxazole derivatives are described. The inventive compounds are useful as kinase inhibitors, and may be used in the treatment of cancer, such as prostate cancer, lung cancer, breast cancer, colon cancer, leukemia, CNS cancer, melanoma, ovarian cancer, and renal cancer.

22 Claims, 46 Drawing Sheets

N-(3-((5-(4-cyanophenyl)oxazol-2-yl)amino)phenyl)-1-phenylmethanesulfonamide

| I. Enzymatic Assay Results: | CDK2 % Inhibition (5 uM): | 100% |
|---|---|---|
| | CDK2- IC50: | 140 nM |

| II. MTT (Cell Based Assay) Results: | DU145 (Prostate) IC50: | 1. 492 micro molar |

N-(3-((5-(4-cyanophenyl)oxazol-2-yl)amino)phenyl)methanesulfonamide

I. Enzymatic Assay Results:     CDK2 % Inhibition (5uM):    104%

CDK2- IC50:    27.1 nM

II. MTT (Cell Based Assay) Results:    DU145 (Prostate) IC50:    2.1 micro molar 4-(2-((3-hydroxyphenyl)amino)oxazol-5-yl)benzonitrile

| I. Enzymatic Assay Results: | CDK2 % Inhibition (5 uM): | 104% |
| --- | --- | --- |
| | CDK2- IC50: | 19.3 nM |
| II. MTT (Cell Based Assay) Results: | DU145 (Prostate) IC50: | 1.88 micro molar |

3-((5-(isoquinolin-6-yl)oxazol-2-yl)amino)phenol

I. Enzymatic Assay Results:   CDK2 % Inhibition (5 uM): 105%

CDK2- IC50: 6. 51 nM

II. MTT (Cell Based Assay) Results:   DU145 (Prostate) IC50: 772.2 picomolar (0.772 nM)

3-((5-(1H-indol-2-yl)oxazol-2-yl)amino)phenol

I. Enzymatic Assay Results:       CDK2 % Inhibition (5 uM):    14%

CDK2- IC50:                  Not tested

II. MTT (Cell Based Assay) Results:   Not available yet

N-(3-((5-(1H-indol-2-yl)oxazol-2-yl)amino)phenyl)methanesulfonamide

| I. Enzymatic Assay Results: | CDK2 % Inhibition (5uM): | 90% |
|---|---|---|
| | CDK2- IC50: | 1190 nM |
| II. MTT (Cell Based Assay) Results: | DU145 (Prostate) IC50: | Not availbale yet |

N-(3-((5-(isoquinolin-6-yl)oxazol-2-yl)amino)phenyl)-1-phenylmethanesulfonamide

| | | |
|---|---|---|
| I. Enzymatic Assay Results: | CDK2 % Inhibition (5uM): | 101% |
| | CDK2- IC50: | 13.6 nM |
| II. MTT (Cell Based Assay) Results: | DU145 (Prostate) IC50: | 197.3 pico molar (0.197 nM) |

N-(3-((5-(1H-indol-2-yl)oxazol-2-yl)amino)phenyl)-1-phenylmethanesulfonamide

| | | |
|---|---|---|
| I. Enzymatic Assay Results: | CDK2 % Inhibition (5uM): | 48% |
| | CDK2- IC50: | Not tested |
| II. MTT (Cell Based Assay) Results: | DU145 (Prostate) IC50: | Not available yet |

3-((5-(4-(trifluoromethyl)phenyl)oxazol-2-yl)amino)phenol

| | | |
|---|---|---|
| I. Enzymatic Assay Results: | CDK2 % Inhibition (5uM): | 36% |
| | CDK2- IC50: | Not tested |
| II. MTT (Cell Based Assay) Results: | DU145 (Prostate) IC50: | Not available yet |

N-(3-((5-(4-(trifluoromethyl)phenyl)oxazol-2-yl)amino)phenyl)methanesulfonamide

| I. Enzymatic Assay Results: | CDK2 % Inhibition (5uM): | 60% |
| --- | --- | --- |
| | CDK2- IC50: | 3.7 micro molar |
| II. MTT (Cell Based Assay) Results: | DU145 (Prostate) IC50: | 3.42 micro molar |

1-phenyl-N-(3-((5-(4-(trifluoromethyl)phenyl)oxazol-2-yl)amino)phenyl)methanesulfonamide

| | | |
|---|---|---|
| I. Enzymatic Assay Results: | CDK2 % Inhibition (5uM): | 29% |
| | CDK2- IC50: | Not tested |
| II. MTT (Cell Based Assay) Results: | DU145 (Prostate) IC50: | 9.09 micro molar |

4-(2-((3-(1H-tetrazol-5-yl)phenyl)amino)oxazol-5-yl)benzonitrile

| | | |
|---|---|---|
| I. Enzymatic Assay Results: | CDK2 % Inhibition (5uM): | 101% |
| | CDK2- IC50: | 162 nM (0.162 micro molar) |
| II. MTT (Cell Based Assay) Results: | DU145 (Prostate) IC50: | 121.58 micro molar |

N-(3-((5-(4-cyano-3-fluorophenyl)oxazol-2-yl)amino)phenyl)methanesulfonamide

| I. Enzymatic Assay Results: | CDK2 % Inhibition (5uM): | 93% |
| --- | --- | --- |
| | CDK2- IC50: | 383 nM (0.383 micro molar) |
| II. MTT (Cell Based Assay) Results: | DU145 (Prostate) IC50: | 7.79 micro molar |

N-(3-((5-(4-(1H-tetrazol-5-yl)phenyl)oxazol-2-yl)amino)phenyl)methanesulfonamide

| | | |
|---|---|---|
| I. Enzymatic Assay Results: | CDK2 % Inhibition (5uM): | 84% |
| | CDK2- IC50: | 898 nM (0.898 micro molar) |
| II. MTT (Cell Based Assay) Results: | DU145 (Prostate) IC50: | 90.68 micro molar |

N-(3-((5-(4-cyanophenyl)oxazol-2-yl)amino)phenyl)-1,1,1-trifluoromethanesulfonamide

| | | |
|---|---|---|
| I. Enzymatic Assay Results: | CDK2 % Inhibition (5uM): | 98% |
| | CDK2- IC50: | 674 nM (0.674 micro molar) |
| II. MTT (Cell Based Assay) Results: | DU145 (Prostate) IC50: | 75.98 micro molar | tert-butyl 5-fluoro-2-(2-((3-hydroxyphenyl)amino)oxazol-5-yl)-1H-indole-1-carboxylate

| | | |
|---|---|---|
| I. Enzymatic Assay Results: | CDK2 % Inhibition (5uM): | 3% |
| | CDK2- IC50: | Not Tested |
| II. MTT (Cell Based Assay) Results: | DU145 (Prostate) IC50: | Not available yet |

*tert*-butyl 5-fluoro-2-(2-((3-(methylsulfonamido)phenyl)amino)oxazol-5-yl)-1*H*-indole-1-carboxylate

| I. Enzymatic Assay Results: | CDK2 % Inhibition (5uM): | 9% |
| --- | --- | --- |
| | CDK2- IC50: | Not Tested |
| II. MTT (Cell Based Assay) Results: | DU145 (Prostate) IC50: | Not available yet |

N-(3-((5-(4-cyanophenyl)thiazol-2-yl)amino)phenyl)methanesulfonamide

I. Enzymatic Assay Results:         CDK2 % Inhibition (5uM):    57%

CDK2- IC50:                 Not Tested

II. MTT (Cell Based Assay) Results: DU145 (Prostate) IC50:      Not available yet N-(3-((5-(isoquinolin-6-yl)oxazol-2-yl)amino)phenyl)methanesulfonamide

I. Enzymatic Assay Results:  CDK2 % Inhibition (5uM):  102%

CDK2- IC50:  4.4 nM

II. MTT (Cell Based Assay) Results:  DU145 (Prostate) IC50:  Not available yet

Figure 45

| Structure | CDK2 Inhibition at 5 uM | CDK2 IC50 | Cytotoxicity DU145 (Prostate) IC50 |
|---|---|---|---|
| (isoquinoline-oxazole-NH-phenyl-OH) | 105% | 6.51 nM | 772.2 picomolar (0.772 nM) |
| (isoquinoline-oxazole-NH-phenyl-NHSO2CH2Ph) | 101% | 13.6 nM | 197.3 picomolar (0.197 nM) |
| (isoquinoline-oxazole-NH-phenyl-NHSO2CH3) | 102% | 4.4 nM | TBD |

| Structure | CDK2 Inhibition at 5 uM | CDK2 IC50 | Cytotoxicity DU145 (Prostate) IC50 |
|---|---|---|---|
| 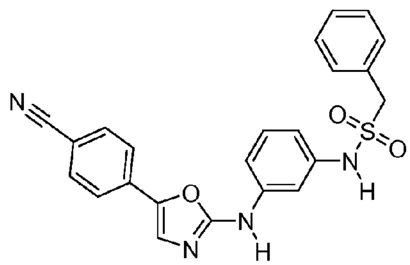 | 100% | 140 nM | 1.492 uM |
|  | 104% | 27.1 nM | 2.1 uM |
|  | 104% | 19.3 nM | 1.88 uM |

| Structure | CDK2 Inhibition at 5 uM | CDK2 IC50 | Cytotoxicity DU145 (Prostate) IC50 |
|---|---|---|---|
| 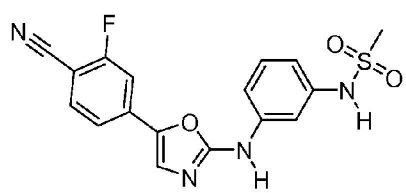 | 93% | 383 nM | 7.79 uM |
| 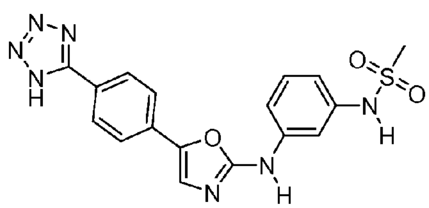 | 84% | 898 nM | 90.68 uM |

| Structure | CDK2 Inhibition at 5 uM | CDK2 IC50 | Cytotoxicity DU145 (Prostate) IC50 |
|---|---|---|---|
| 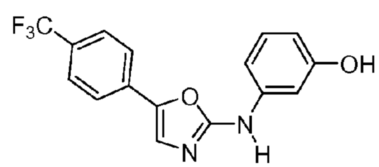 | 36% | TBD | TBD |
| 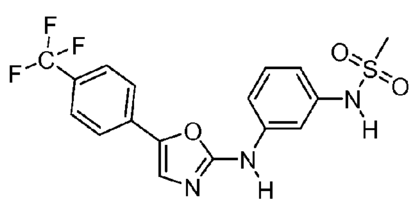 | 60% | 3.7 uM | 3.42 uM |
| 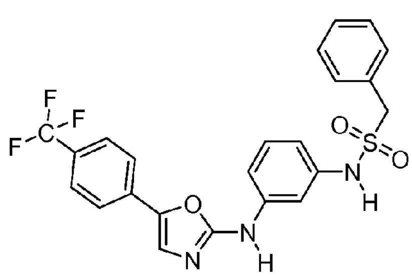 | 29% | TBD | 9.09 uM |

| Structure | CDK2 Inhibition at 5 uM | CDK2 IC50 | Cytotoxicity DU145 (Prostate) IC50 |
|---|---|---|---|
| 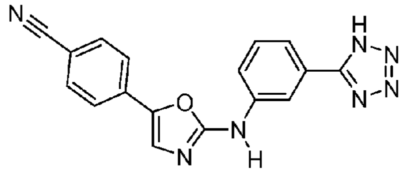 | 101% | 162 nM | 121.58 uM |
| 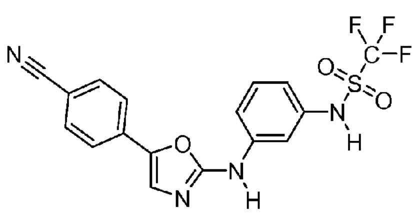 | 98% | 674 nM | 75.98 uM |

Figure 54

| Structure | CDK2 Inhibition at 5 uM | CDK2 IC50 | Cytotoxicity DU145 (Prostate) IC50 |
|---|---|---|---|
| (indole-oxazole-NH-phenyl-OH) | 14% | N/A | N/A |
| (indole-oxazole-NH-phenyl-NHSO2Me) | 90% | 1190 nM | N/A |
| (indole-oxazole-NH-phenyl-NHSO2CH2Ph) | 48% | N/A | N/A |
| (5-F-indole-N-Boc-oxazole-NH-phenyl-OH) | 3% | N/A | N/A |
| (5-F-indole-N-Boc-oxazole-NH-phenyl-NHSO2Me) | 9% | TBD | TBD |
| (6-F-indole-oxazole-NH-phenyl-NHSO2Me) | 79% | TBD | TBD |
| (5-F-indole-oxazole-NH-phenyl-NHSO2Me) | 68% | TBD | TBD |

| Structure | CDK2 Inhibition at 5 uM | CDK2 IC50 | Cytotoxicity DU145 (Prostate) IC50 |
|---|---|---|---|
| 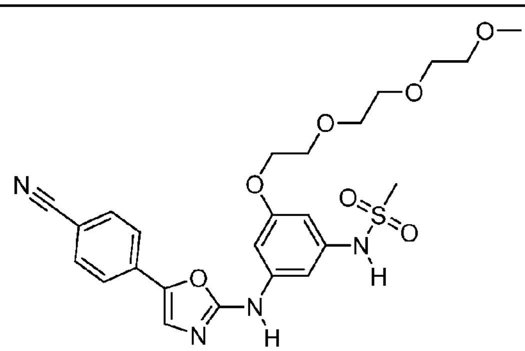 | 99% | 68.7 nM |  |

| Group | Treatment | # of Animals | Dose (mg/kg) | Concentration (mg/mL) | Dosing Volume (mL/kg) | Blood Collection |
|---|---|---|---|---|---|---|
| 1 | Untreated | 3 | N/A | N/A | 10 | Pre-dose |
| 2 | Neos 223 | 3 | 20 | 2 | 10 | 15 min |
| 3 | Neos 223 | 3 | 20 | 2 | 10 | 30 min |
| 4 | Neos 223 | 3 | 20 | 2 | 10 | 1 hr. |
| 5 | Neos 223 | 3 | 20 | 2 | 10 | 2 hr. |
| 6 | Neos 223 | 3 | 20 | 2 | 10 | 4 hr. |
| 7 | Neos 223 | 3 | 20 | 2 | 10 | 6 hr. |
| 8 | Neos 223 | 3 | 20 | 2 | 10 | 8 hr. |
| 9 | Neos 223 | 3 | 20 | 2 | 10 | 24 hr. |
| 10 | Neos 223 | 3 | 20 | 2 | 10 | 48 hr. |

Figure 62

| Group | Time point (hr.) | Dose (mg/kg) | Concentration (ng/ml) |
|---|---|---|---|
| 1 | 0 | 20 | 0.00 |
| 1 | 0.25 | 20 | 749.08 |
| 1 | 0.5 | 20 | 1115.46 |
| 1 | 1 | 20 | 1473.24 |
| 1 | 2 | 20 | 2849.50 |
| 1 | 4 | 20 | 1207.57 |
| 1 | 6 | 20 | 1103.86 |
| 1 | 8 | 20 | 223.86 |
| 1 | 24 | 20 | 4.84 |
| 1 | 48 | 20 | 0.41 |

| AUClast (h*ng/mL) | AUC∞ (h*ng/mL) | D_AUC∞ (h*kg*ng/mL/mg) | Cmax (ng/mL) | T1/2 (h) | Tmax (h) | Vd (mL/kg) | CL (mL/h/kg) |
|---|---|---|---|---|---|---|---|
| 11330.216 | 11331.243 | 566.562 | 2849.500 | 3.588 | 2.0 | 9135.902 | 1764.861 |

1,3-OXAZOLE-4-CARBOXAMIDES, 1,3-THIAZOLE-4-CARBOXAMIDES, AND 1,3-IMIDAZOLE-D-CARBOXAMIDES AS INHIBITORS OF CYCLIN DEPENDENT KINASES

RELATED APPLICATIONS

This application is a divisional application of U.S. application Ser. No. 13/478,376, filed May 23, 2012, which claims the benefit of priority to U.S. Provisional Patent Application Ser. No. 61/490,789, filed May 27, 2011, the contents of both of which are hereby incorporated by reference.

BACKGROUND OF THE INVENTION

Small-molecule kinase inhibitors have emerged over the past decade as an important class of anti-cancer agents. Cyclin dependent kinases (CDK) are of particular interest because their activities are frequently misregulated in a wide variety of human cancers. The cyclin dependent kinases (for example CDK-2) are serine/threonine protein kinases, which are the driving force behind the cell cycle and cell proliferation. Although several molecules that inhibit cell cycle kinases have been developed and clinically screened as potential anticancer agents, none of these has been approved for commercial use because of dystrophia myotonica protein kinase issues. Therefore, there exists a need for new compounds to treat cancers associated with cyclin dependent kinases. It is, therefore, an object of this invention to provide compounds for the treatment or prevention of such diseases.

SUMMARY OF THE INVENTION

In certain embodiments, the invention relates to a compound of Formula I

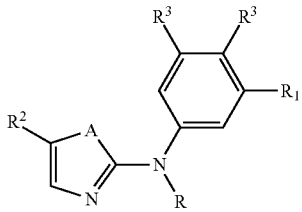

wherein, independently for each occurrence,
R$^1$ is heteroaryl, halo, —NR—SO$_2$-alkyl, —NR—SO$_2$-haloalkyl, —NR—SO$_2$-aralkyl, —OR, —NR—C(O)—R, or —NR$_2$;
R$^2$ is aryl or heteroaryl;
R$^3$ is —H, —OR$^4$, —NR$_2$, or halo;
A is —O—, —S—, or —NR—;
R is —H, or substituted or unsubstituted alkyl, or two R substituents, taken together with the atoms to which they are attached, form a six-membered heterocycloalkyl ring;
R$^4$ is —H, alkyl, or —(CR$_2$CR$_2$—O—)$_x$—R; and
x is 1, 2, 3, 4, 5, 6, 7, or 8.

In certain embodiments, the invention relates to a compound of Formula II

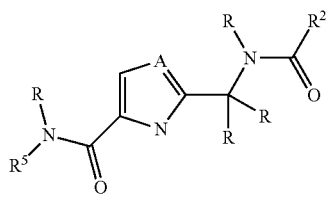

wherein, independently for each occurrence,
R$^2$ is aryl or heteroaryl;
A is —O—, —S—, or —NR—;
R is —H, or alkyl; and
R$^5$ is aryl or heteroaryl.

In certain embodiments, the invention relates to a compound of Formula III

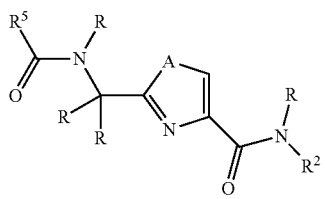

wherein, independently for each occurrence,
R$^2$ is aryl or heteroaryl;
A is —O—, —S—, or —NR—;
R is —H, or alkyl; and
R$^5$ is aryl or heteroaryl.

In certain embodiments, the invention relates to a method of treating cancer, comprising administering to a mammal in need thereof a therapeutically effective amount of any one of the aforementioned compounds.

In certain embodiments, the invention relates to a method of regulating, modulating, or inhibiting CDK2, CDK4, or VEGFR2 in a cell, comprising contacting the cell with a therapeutically effective amount of a compound of any one of the aforementioned compounds.

In certain embodiments, the invention relates to a method of treating a disorder mediated by inappropriate VEGFR2 or CDK activity, comprising administering to a mammal in need thereof a therapeutically effective amount of any one of the aforementioned compounds.

In certain embodiments, the invention relates to a method of treating a disease, comprising administering to a mammal in need thereof a therapeutically effective amount of any one of the aforementioned compounds, wherein the disease is characterized by cellular proliferation; and the disease is associated with neo-vascularization or vascular permeability.

BRIEF DESCRIPTION OF THE FIGURES

FIG. 45 tabulates assay data for various isoquinoline-containing compounds of the invention.

FIG. 54 tabulates assay data for various indole- and fluoroindole-containing compounds of the invention.

FIG. 61 tabulates the experimental variables outlined in Example 22, a pharmacokinetic analysis of a compound of the invention in male ICR mice.

FIG. 62 tabulates the mean plasma concentration of a compound of the invention (Compound 223) after single oral dosing in male ICR mice.

DETAILED DESCRIPTION OF THE INVENTION

Overview

Figure 1:
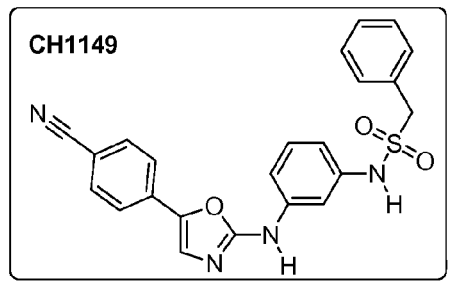
FIG. 1 depicts assay results for a compound of the invention.

In certain embodiments, the invention relates to amino oxazole CDK inhibitors. In certain embodiments, a number of different pharmacophores in these compounds have been identified (for example, isoquinoline nitrogen, tetrazole core, ethylene glycol core, cyano, and sulfonamide). In certain embodiments, the compounds of the invention provide useful leads for the discovery and development of orally active CDK inhibitors.

An in silico screening approach to compounds exhibiting CDK inhibition was utilized; the approach is described in detail below. Three series of compounds were developed, and are described in detail below. In each series, structure-activity relationship studies led to the discovery of high potency compounds with excellent ligand efficiency. In certain embodiments, isoquinoline containing amino-oxazole compounds show sub-nanomolar affinity and good cellular potency.

In certain embodiments, and not wishing to be bound by any particular theory, a key ligand region was identified, and is described in more detail below. In certain embodiments, it is desirable to incorporate ligands at this position. In certain embodiments, it is desirable to incorporate a hydrophilic moiety at this position. In certain embodiments, incorporating a hydrophilic moiety at this position improves water solubility without affecting key interactions of the compound with the protein.

DEFINITIONS

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "heteroatom" is art-recognized and refers to an atom of an element other than carbon or hydrogen. Illustrative heteroatoms include boron, nitrogen, oxygen, phosphorus, sulfur and selenium.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "arylalkoxy" and "heteroalkoxy" as used herein, means an aryl group or heteroaryl group, as defined herein, appended to the parent molecular moiety through an alkoxy group, as defined herein. Representative examples of arylalkoxy include, but are not limited to, 2-chlorophenylmethoxy, 3-trifluoromethylethoxy, and 2,3-methylmethoxy.

The term "arylalkyl" as used herein, means an aryl group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" and "arylcarbonyloxy" as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "amido" as used herein, means —NHC(=O)—, wherein the amido group is bound to the parent molecular moiety through the nitrogen. Examples of amido include alkylamido such as $CH_3C(=O)N(H)—$ and $CH_3CH_2C(=O)N(H)—$.

The term "amino" as used herein, refers to radicals of both unsubstituted and substituted amines appended to the parent molecular moiety through a nitrogen atom. The two groups are each independently hydrogen, alkyl, alkylcarbonyl, alkylsulfonyl, arylcarbonyl, or formyl. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl," as used herein, means a phenyl group or a naphthyl group. The aryl groups of the present invention can be optionally substituted with 1, 2, 3, 4 or 5 substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "arylene," is art-recognized, and as used herein, pertains to a bidentate moiety obtained by removing two hydrogen atoms of an aryl ring, as defined above.

The term "arylalkyl" or "aralkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-yl-ethyl.

The term "arylalkoxy" or "arylalkyloxy" as used herein, means an arylalkyl group, as defined herein, appended to the parent molecular moiety through an oxygen. The term "heteroarylalkoxy" as used herein, means an heteroarylalkyl group, as defined herein, appended to the parent molecular moiety through an oxygen.

The term "arylalkylthio" as used herein, means an arylalkyl group, as defined herein, appended to the parent molecular moiety through an sulfur. The term "heteroarylalkylthio" as used herein, means an heteroarylalkyl group, as defined herein, appended to the parent molecular moiety through an sulfur.

The term "arylalkenyl" as used herein, means an aryl group, as defined herein, appended to the parent molecular moiety through an alkenyl group. A representative example is phenylethylenyl.

The term "arylalkynyl" as used herein, means an aryl group, as defined herein, appended to the parent molecular moiety through an alkynyl group. A representative example is phenylethynyl.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "arylcarbonylalkyl" as used herein, means an arylcarbonyl group, as defined herein, bound to the parent molecule through an alkyl group, as defined herein.

The term "arylcarbonylalkoxy" as used herein, means an arylcarbonylalkyl group, as defined herein, bound to the parent molecule through an oxygen.

The term "aryloxy" as used herein, means an aryl group, as defined herein, appended to the parent molecular moiety through an oxygen. The term "heteroaryloxy" as used herein, means a heteroaryl group, as defined herein, appended to the parent molecular moiety through an oxygen.

The term "carbonyl" as used herein, means a —C(=O)— group.

The term "carboxy" as used herein, means a —CO$_2$H group.

The term "cycloalkyl" as used herein, means monocyclic or multicyclic (e.g., bicyclic, tricyclic, etc.) hydrocarbons containing from 3 to 12 carbon atoms that is completely saturated or has one or more unsaturated bonds but does not amount to an aromatic group. Examples of a cycloalkyl group include cyclopropyl, cyclobutyl, cyclopentyl, cyclopentenyl, cyclohexyl and cyclohexenyl.

The term "cycloalkoxy" as used herein, means a cycloalkyl group, as defined herein, appended to the parent molecular moiety through an oxygen.

The term "cyano" as used herein, means a —CN group.

The term "formyl" as used herein, means a —C(=O)H group.

The term "halo" or "halogen" means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl", as used herein, include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b) thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroarylene," is art-recognized, and as used herein, pertains to a bidentate moiety obtained by removing two hydrogen atoms of a heteroaryl ring, as defined above.

The term "heteroarylalkyl" or "heteroaralkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl) ethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "phosphinyl" as used herein includes derivatives of the H$_3$P— group, wherein the hydrogens are independently replaced with alkyl, adamantyl, fluoroalkyl, cycloalkyl, aryl, heteroaryl, heterocyclyl, aryloxy, or heteroaryloxy groups.

The term "silyl" as used herein includes hydrocarbyl derivatives of the silyl (H$_3$Si—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The definition of each expression, e.g., alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiamers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

For purposes of this invention, the chemical elements are identified in accordance with the Periodic Table of the Elements, CAS version, Handbook of Chemistry and Physics, 67th Ed., 1986-87, inside cover.

The term "effective" amount refers to the amount of a compound of the present invention required to treat or prevent a disease (e.g., cancer), or the amount of a compound of the present invention required to inhibit an enzyme (e.g., CDK2). The effective amount of a compound of the invention used to practice the invention for therapeutic or prophylactic treatment of diseases varies depending upon the manner of administration, the age, body weight, and general health of the subject. An effective amount of a compound, as defined herein may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the compound are outweighed by the therapeutically beneficial effects. A therapeutically effective amount of a compound (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "pharmaceutical composition" refers to a composition containing a compound of the invention formulated with one or more pharmaceutical-grade excipients in a manner that conforms with the requirements of a governmental agency regulating the manufacture and sale of pharmaceuticals as part of a therapeutic regimen for the treatment or prevention of disease in a mammal (e.g., manufactured according to GMP regulations and suitable for administration to a human). Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or any other formulation described herein.

The term "pharmaceutically acceptable carrier" refers to any such carriers known to those skilled in the art to be suitable for the particular mode of administration. For example, the term "pharmaceutically acceptable carrier"

includes any and all solvents, dispersion media, coatings, antibacterial and antifungal agents, isotonic and absorption delaying agents and the like, that may be used as a media for a pharmaceutically acceptable substance. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

As used herein, the term "treating" refers to administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

The term "subject" includes humans, and non-human animals amenable to therapy, e.g., preferably mammals and animals susceptible to a disease (e.g., cancer), including non-human primates, transgenic animals, mice, rats, dogs, cats, rabbits, pigs, chickens, sheep, horses, and cows. Preferably, the subject is a human subject.

As used herein, the phrase "therapeutic effect" refers to a local or systemic effect in animals, particularly mammals, and more particularly humans, caused by an agent. The phrases "therapeutically-effective amount" and "effective amount" mean the amount of an agent that produces some desired effect in at least a sub-population of cells. A therapeutically effective amount includes an amount of an agent that produces some desired local or systemic effect at a reasonable benefit/risk ratio applicable to any treatment. For example, certain agents used in the methods of the present invention may be administered in a sufficient amount to produce a reasonable benefit/risk ratio applicable to such treatment.

Compound Design

Overview

Figure 41:
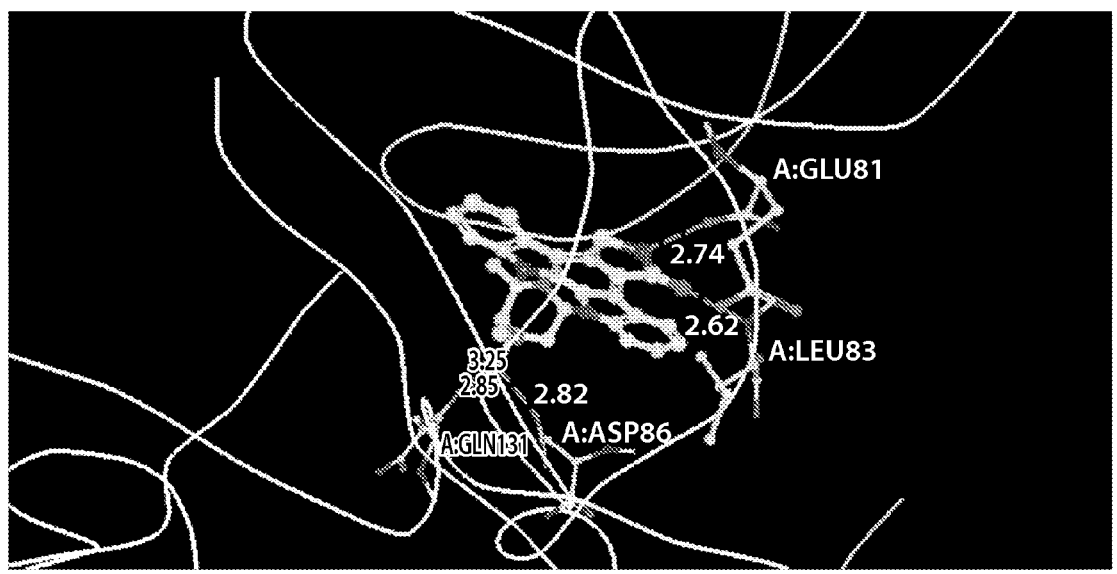
FIG. 41 depicts a simulation of a CDK2-staurosporine complex.

A Staurosporine-CDK2 co-crystal structure (PDB #1AQ1), was used to predict the binding mode of the aminooxazole at the ATP binding site. Staurosporine is a prototypical ATP-competitive kinase inhibitor in that it binds to many kinases with high affinity, though with little selectivity. This lack of specificity has precluded its clinical use. Staurosporine exhibits nanomolar IC50 values against a wide range of protein kinases. The structure of a CDK2 staurosporine complex (FIG. 41) explains the tight binding of this inhibitor, and suggests features to be exploited in the design of specific inhibitors of CDKs.

Figure 42A:
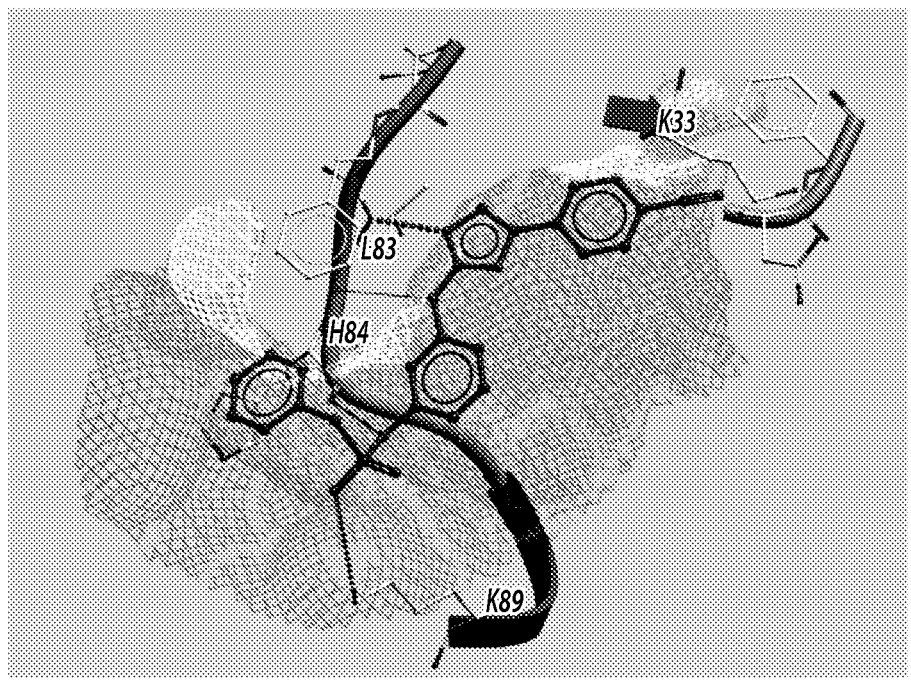
FIG. 42 depicts molecular docking structures of CDK2 complexed with various compounds of the invention. The drawings show that hydrogen-bonding interactions may include those between oxazole-N— and L83 hinge backbone —NH—, and between the aniline-NH— and L83 hinge backbone carbonyl-O—.
Figure 42B:
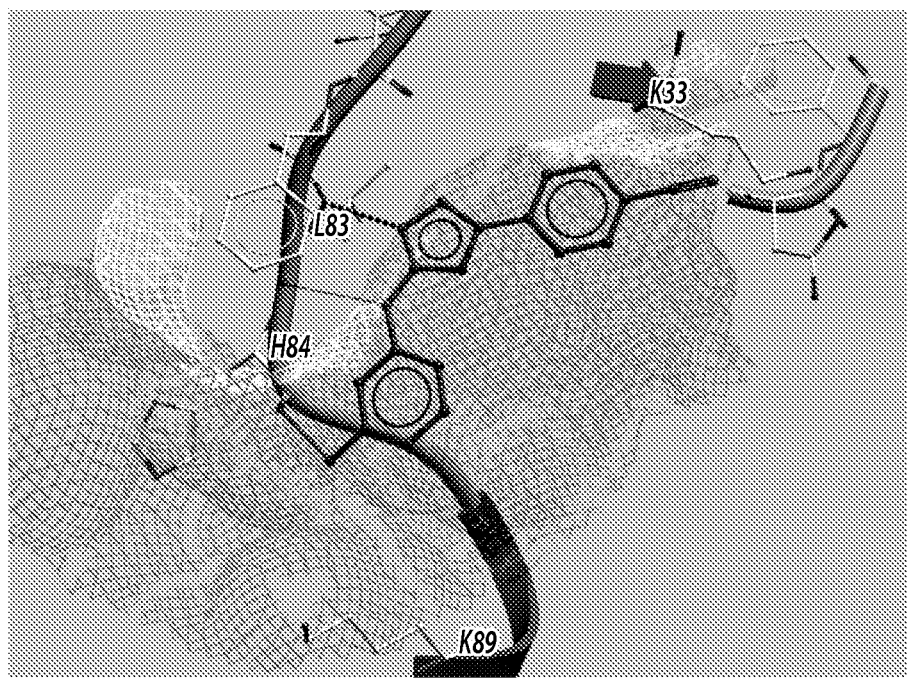
Figure 43:
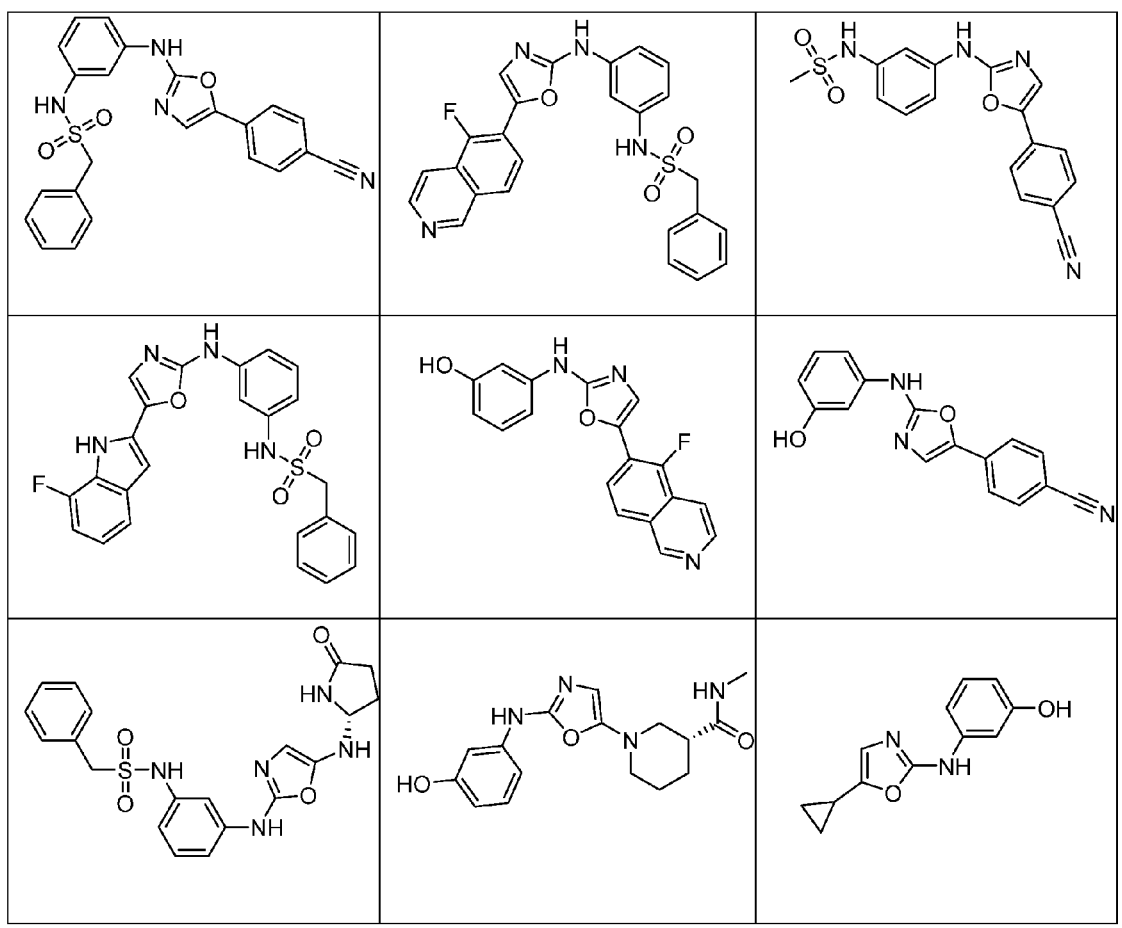
FIG. 43 depicts compounds predicted to display desirable hydrogen bonding interactions.

The L83 (leucine) of the peptide backbone was thought to bind to the inhibitor via hydrogen donor and acceptor bonds with the aniline and oxazole nitrogens, respectively. In certain embodiments, the invention relates to in silico-based drug discovery to derive synthetic inhibitors of CDK with improved selectivity and pharmaceutical properties. In certain embodiments, the invention relates to chemotypes designed to be CDK inhibitors utilizing the structure of 1AQ1. The molecular docking structures of CDK2 complexed with various compounds of the invention show that the key hydrogen bonding interactions may include those between oxazole-N— and L83 hinge backbone —NH—, and between the aniline-NH— and L83 hinge backbone carbonyl-O— (FIG. 42). In certain embodiments, modeling shows that the above-mentioned hydrogen bonds are maintained in complexes with the compounds of the invention. In certain embodiments, exemplary compounds maintaining the predicted arrangement are depicted in FIG. 43.

Isoquinoline Series

Not wishing to be bound by any particular theory, the nitrogen atom in isoquinoline (FIG. 44) is thought to bind with the K33 (lysine) of CDK2 via hydrogen acceptor. In certain embodiments, compounds comprising an isoquinoline moiety showed sub-nanomolar CDK2 inhibition.

Figure 44:
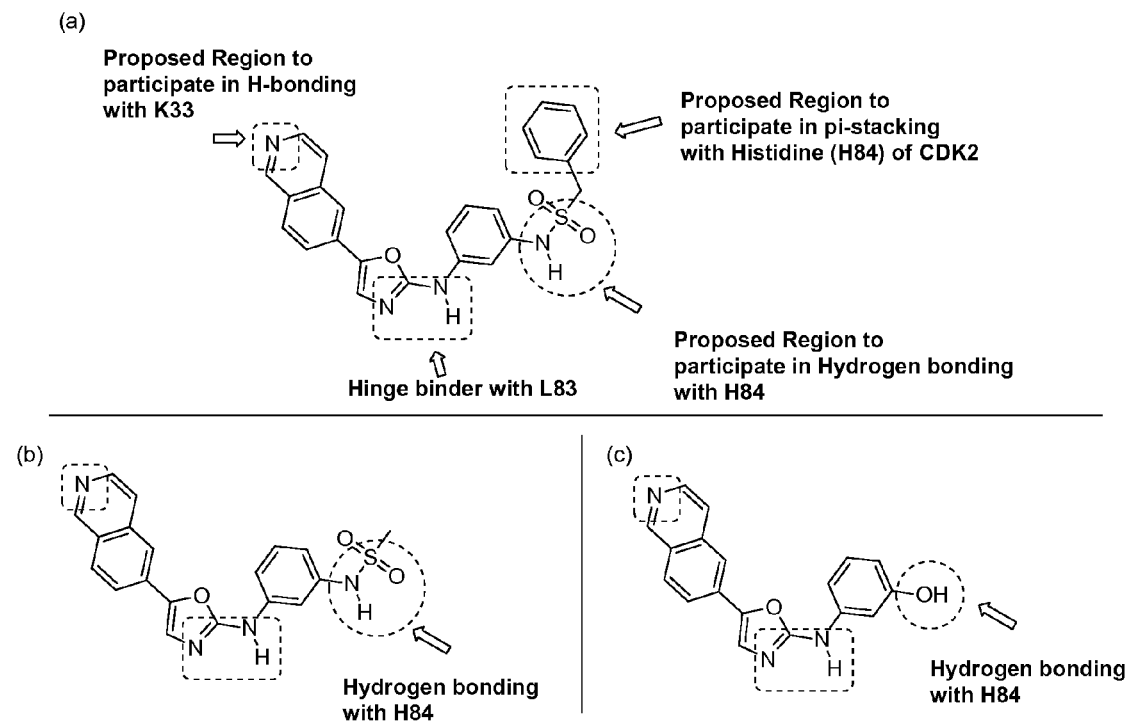
FIG. 44 depicts predicted bonding interactions for various isoquinoline-containing compounds of the invention.

Not wishing to be bound by any particular theory, sulfonamide (FIG. 44 (a) and FIG. 44 (b)) or phenolic (FIG. 44 (c)) substituents were thought to impart increased potency by virtue of the aralkyl (FIG. 44 (a)) or alkyl (FIG. 44 (b)) sulfonamide substituent sitting in a small hydrophobic pocket, coupled with sulfonamide hydrogen involving in a hydrogen bond with the backbone nitrogen of histidine (H84). In certain embodiments, amino oxazole potency was dependent on the presence of a 3-sulfonamide (—NH—SO$_2$—) or phenolic substituent.

FIG. 45 depicts a summary of the activities of various compounds of the invention comprising an isoquinoline substituent. In certain embodiments, compounds with this core structure show unique hydrogen bonding patterns.

Figure 57:
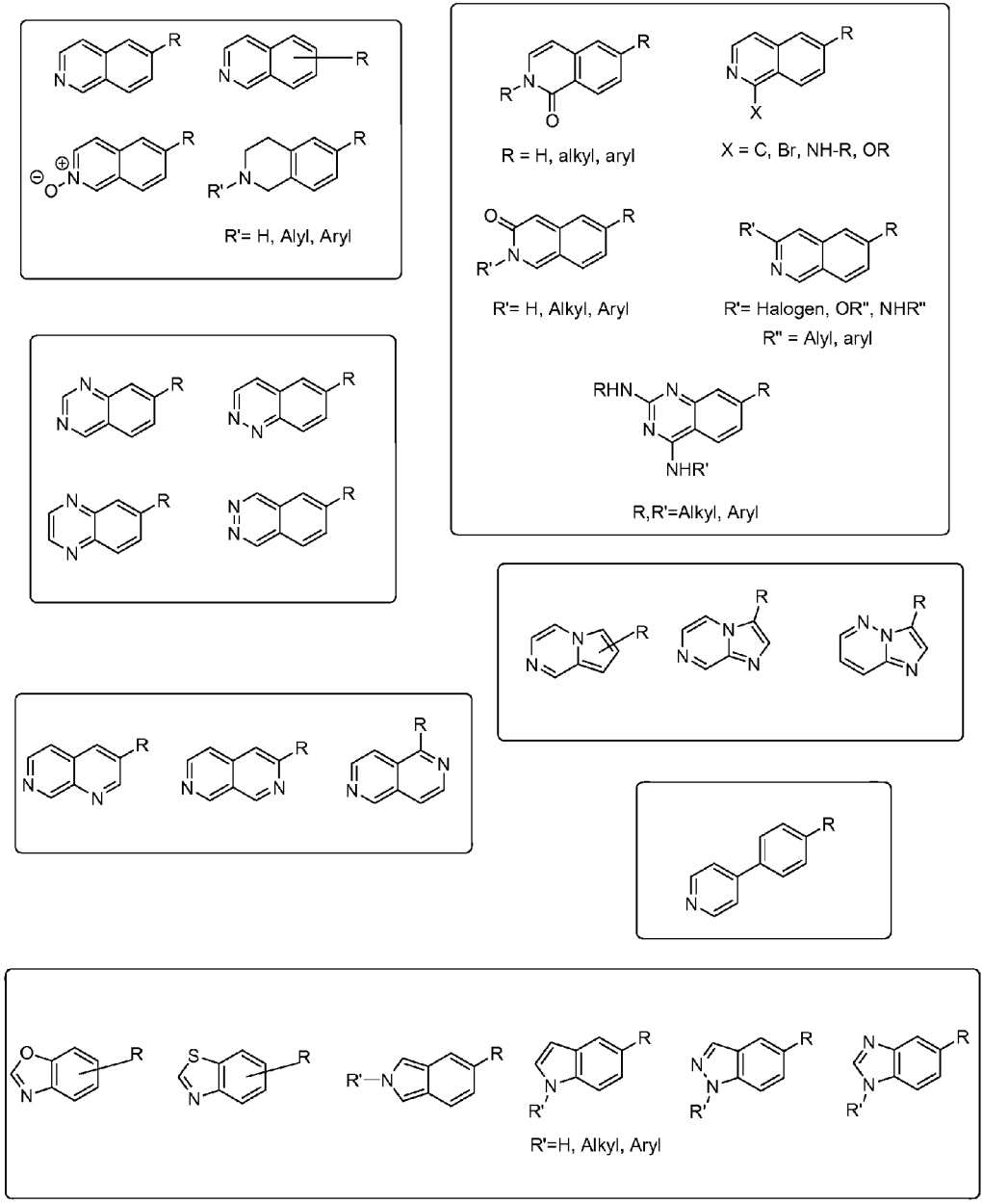
FIG. 57 depicts various isoquinoline isosteres that may be incorporated in embodiments of the invention.

FIG. 57 depicts various embodiments of isoquinoline isosteres that may be used in embodiments of the invention.

Cyanophenyl Series

Figure 46:
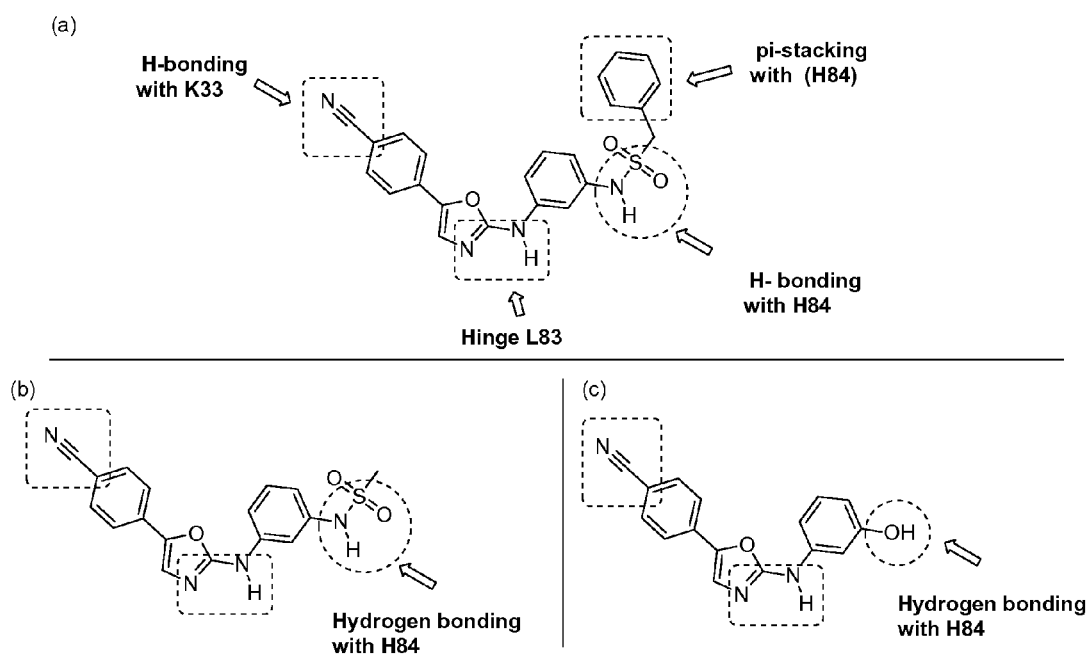
FIG. 46 depicts predicted bonding interactions for various 4-cyanophenyl-containing compounds of the invention.

Not wishing to be bound by any particular theory, the nitrogen atom of 4-cyanophenyl (FIG. 46) is predicted to bind with the K33 via hydrogen acceptor. In certain embodiments, compounds comprising a 4-cyanophenyl substituent showed sub-nanomolar CDK2 inhibition.

Figure 47:
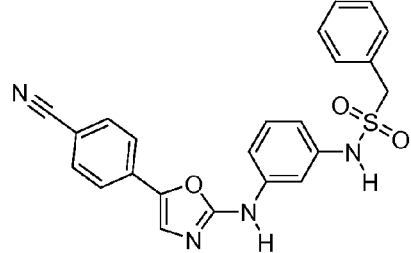
FIG. 47 tabulates assay data for various 4-cyanophenyl-containing compounds of the invention.
Figure 47:
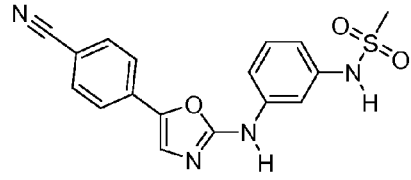
Figure 47:
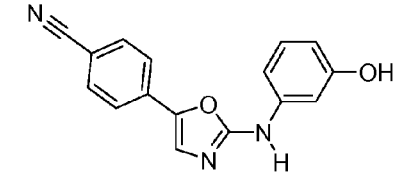

FIG. 47 depicts a summary of the activities of various compounds of the invention comprising a 4-cyanophenyl substituent.

Optimization at —CN Region

Figure 48:
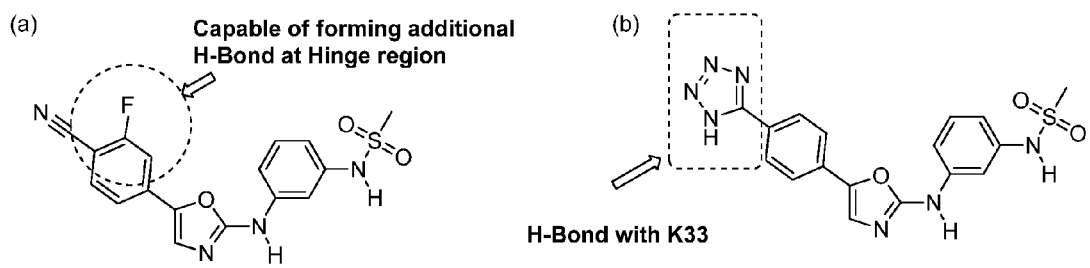
FIG. 48 depicts predicted bonding interactions for various analogs of 4-cyanophenyl-containing compounds of the invention (fluorinated 4-cyanophenyl and tetrazole).
Figure 49:
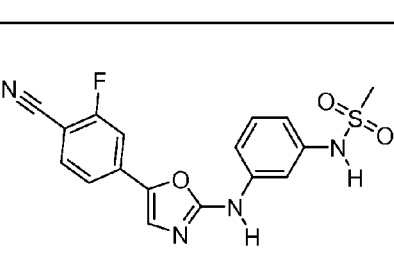
FIG. 49 tabulates assay data for various analogs of 4-cyanophenyl-containing compounds of the invention (fluorinated 4-cyanophenyl and tetrazole).
Figure 49:
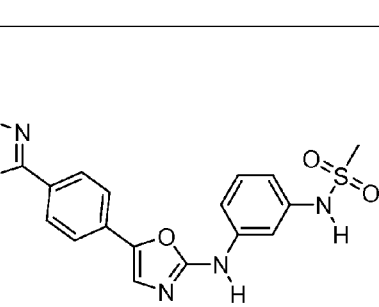

In certain embodiments, introduction of a fluorine substituent on the phenyl ring, or replacement of 4-CN with tetrazole resulted in retention of activity (FIG. 48 and FIG. 49). Not wishing to be bound by any particular theory, these results may confirm the presence of key interactions in the 4-CN region. In certain embodiments, 4-CN may be further optimized.

Figure 50:
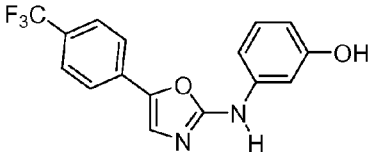
FIG. 50 tabulates assay data for various analogs of 4-cyanophenyl-containing compounds of the invention (4-trifluoromethylphenyl).
Figure 50:
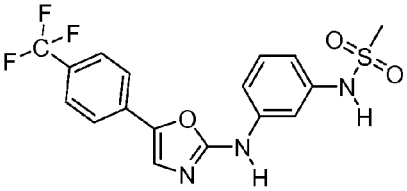
Figure 50:
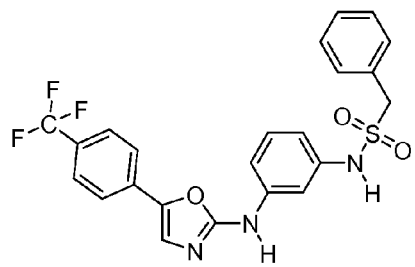

In certain embodiments, replacement of 4-CN with —CF$_3$ resulted in 40% loss of activity (FIG. 50). Not wishing to be bound by any particular theory, this result may confirm the presence of key hydrogen bonding interactions in the 4-CN region.

Optimization at Sulfonamide Region

Figures 51, 52:
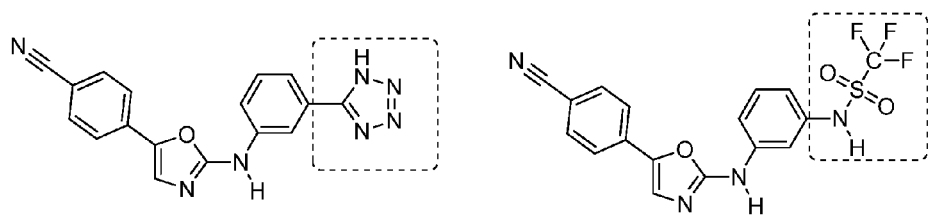
FIG. 51 depicts predicted bonding interactions for various analogs of sulfonamide-containing compounds of the invention (tetrazole and trifluoromethylsulfonamide).
FIG. 52 tabulates assay data for various analogs of sulfonamide-containing compounds of the invention (tetrazole and trifluoromethylsulfonamide).

In certain embodiments, replacement of the sulfonamide substituent with a tetrazole substituent resulted in retention of activity (FIG. 51 and FIG. 52). In certain embodiments, resulting tetrazole analogs are equally potent. In certain embodiments, fluorinated sulfonamides are equally potent. In certain embodiments, it may be desirable to include a hydrogen-bond donor or a more water soluble moiety in this position.

Fluoroindole Series

Figure 53:
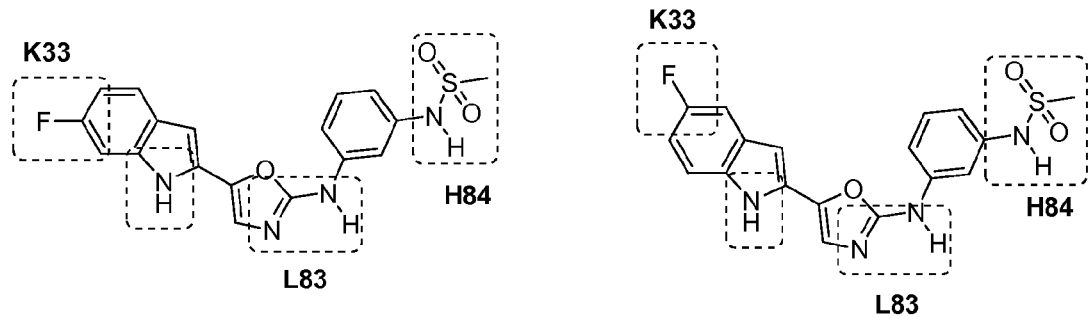
FIG. 53 depicts predicted bonding interactions for various fluoroindole-containing compounds of the invention.

Not wishing to be bound by any particular theory, incorporation of a fluoroindole moiety may increase potency of certain compounds of the invention by enabling hydrogen bonding with K33 of CDK-2. In certain embodiments, compounds of the invention comprising a fluoroindole moiety inhibited CDK-2 up to 79% and 68% (FIGS. 53 and 54).

Optimizing Solubility

Figures 55, 56:
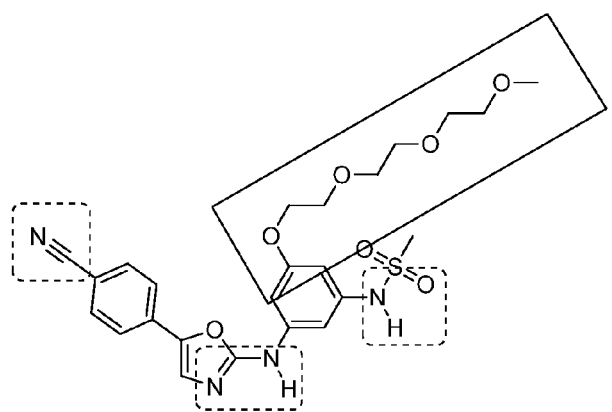
FIG. 55 depicts predicted bonding interactions for an oligo(ethylene glycol)-containing compound of the invention.
FIG. 56 tabulates assay data for an oligo(ethylene glycol)-containing compound of the invention.

In certain embodiments, compounds of the invention suffer from lower than desirable water solubility. In certain embodiments, a low pharmacokinetic profile may be attributed to low water solubility. In certain embodiments, incorporation of a hydrophilic substituent may increase potency of compounds of the invention. In certain embodiments, the hydrophilic substituent is ethylene glycol (FIGS. 55 and 56).

Exemplary Compounds of the Invention

In certain embodiments, the invention relates to a compound of Formula I

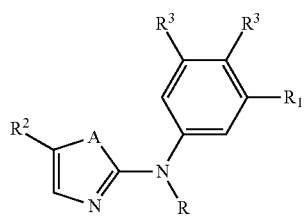

I wherein, independently for each occurrence,

R¹ is heteroaryl, halo, —NR—SO₂-alkyl, —NR—SO₂-haloalkyl, —NR—SO₂-aralkyl, —OR, —NR—C(O)—R, or —NR₂;

R² is aryl or heteroaryl;

R³ is —H, —OR⁴, —NR₂, or halo;

A is —O—, —S—, or —NR—;

R is —H, or substituted or unsubstituted alkyl, or two R substituents, taken together with the atoms to which they are attached, form a six-membered heterocycloalkyl ring;

R⁴ is —H, alkyl, or —(CR₂CR₂—O—)ₓ—R; and x is 1, 2, 3, 4, 5, 6, 7, or 8.

In certain embodiments, the invention relates to any one of the aforementioned compounds, wherein R¹ is —NR—SO₂-alkyl, —NR—SO₂-haloalkyl, —NR—SO₂-aralkyl, or —OR.

In certain embodiments, the invention relates to any one of the aforementioned compounds, wherein R¹ is —NR—SO₂-alkyl. In certain embodiments, the invention relates to any one of the aforementioned compounds, wherein R¹ is —NR—SO₂—CH₃. In certain embodiments, the invention relates to any one of the aforementioned compounds, wherein R¹ is —NR—SO₂—CH₂CH₃.

In certain embodiments, the invention relates to any one of the aforementioned compounds, wherein R¹ is —NR—SO₂-haloalkyl. In certain embodiments, the invention relates to any one of the aforementioned compounds, wherein R¹ is —NR—SO₂—CF₃. In certain embodiments, the invention relates to any one of the aforementioned compounds, wherein R¹ is —NR—SO₂—CHF₂. In certain embodiments, the invention relates to any one of the aforementioned compounds, wherein R¹ is —NR—SO₂—CH₂F.

In certain embodiments, the invention relates to any one of the aforementioned compounds, wherein R¹ is —NR—SO₂-aralkyl. In certain embodiments, the invention relates to any one of the aforementioned compounds, wherein R¹ is —NR—SO₂-benzyl.

In certain embodiments, the invention relates to any one of the aforementioned compounds, wherein R¹ is —OR. In certain embodiments, the invention relates to any one of the aforementioned compounds, wherein R¹ is —OH. In certain embodiments, the invention relates to any one of the aforementioned compounds, wherein R¹ is —OCH₃. In certain embodiments, the invention relates to any one of the aforementioned compounds, wherein R¹ is —OCH₂CH₃. In certain embodiments, the invention relates to any one of the aforementioned compounds, wherein R¹ is

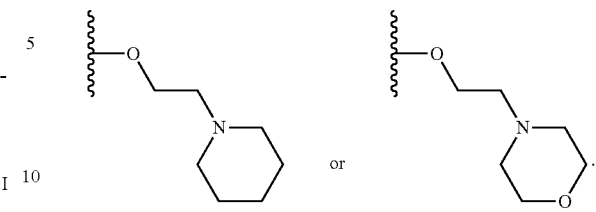

In certain embodiments, the invention relates to any one of the aforementioned compounds, wherein R¹ is —NR₂. In certain embodiments, the invention relates to any one of the aforementioned compounds, wherein R¹ is —NH₂. In certain embodiments, the invention relates to any one of the aforementioned compounds, wherein R¹ is

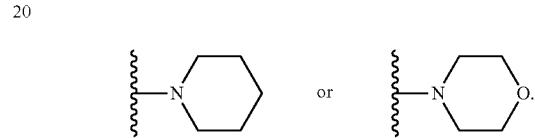

In certain embodiments, the invention relates to any one of the aforementioned compounds, wherein R¹ is unsubstituted heteroaryl. In certain embodiments, the invention relates to any one of the aforementioned compounds, wherein R¹ is

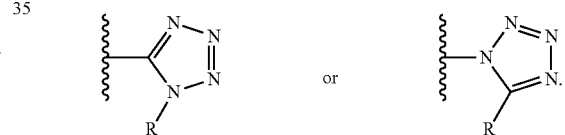

In certain embodiments, the invention relates to any one of the aforementioned compounds, wherein R² is substituted aryl. In certain embodiments, the invention relates to any one of the aforementioned compounds, wherein R² is substituted or unsubstituted heteroaryl. In certain embodiments, the invention relates to any one of the aforementioned compounds, wherein R² is substituted heteroaryl. In certain embodiments, the invention relates to any one of the aforementioned compounds, wherein R² is unsubstituted heteroaryl.

In certain embodiments, the invention relates to any one of the aforementioned compounds, wherein R² is substituted phenyl. In certain embodiments, the invention relates to any one of the aforementioned compounds, wherein R² is 4-substituted phenyl. In certain embodiments, the invention relates to any one of the aforementioned compounds, wherein R² is 3,4-disubstituted phenyl. In certain embodiments, the invention relates to any one of the aforementioned compounds, wherein R² is substituted aryl; and R² is substituted with —CN, tetrazolyl, alkyl, haloalkyl, halo, —OR, or —NR₂. In certain embodiments, the invention relates to any one of the aforementioned compounds, wherein R² is

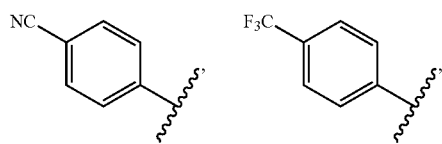

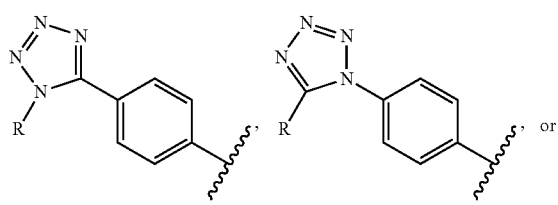

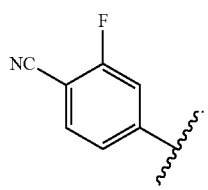

In certain embodiments, the invention relates to any one of the aforementioned compounds, wherein $R^2$ is substituted heteroaryl. In certain embodiments, the invention relates to any one of the aforementioned compounds, wherein $R^2$ is substituted indolyl or substituted isoquinolinyl. In certain embodiments, the invention relates to any one of the aforementioned compounds, wherein $R^2$ is fluoro-substituted indolyl or fluoro-substituted isoquinolinyl. In certain embodiments, the invention relates to any one of the aforementioned compounds, wherein $R^2$ is

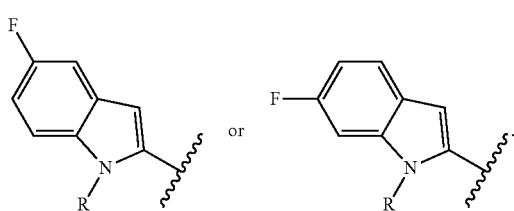

In certain embodiments, the invention relates to any one of the aforementioned compounds, wherein $R^2$ is

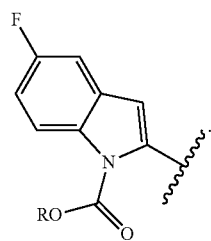

In certain embodiments, the invention relates to any one of the aforementioned compounds, wherein $R^2$ is

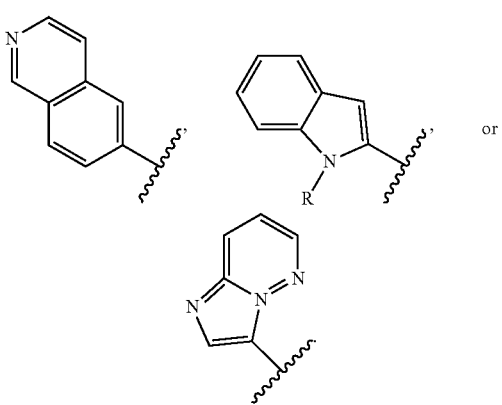

and n is 1, 2, 3, 4, 5, or 6. In certain embodiments, the invention relates to any one of the aforementioned compounds, wherein $R^2$ is In certain embodiments, the invention relates to any one of the aforementioned compounds, wherein $R^2$ is unsubstituted indolyl or unsubstituted isoquinolinyl. In certain embodiments, the invention relates to any one of the aforementioned compounds, wherein $R^2$ is In certain embodiments, the invention relates to any one of the aforementioned compounds, wherein $R^2$ is substituted or unsubstituted

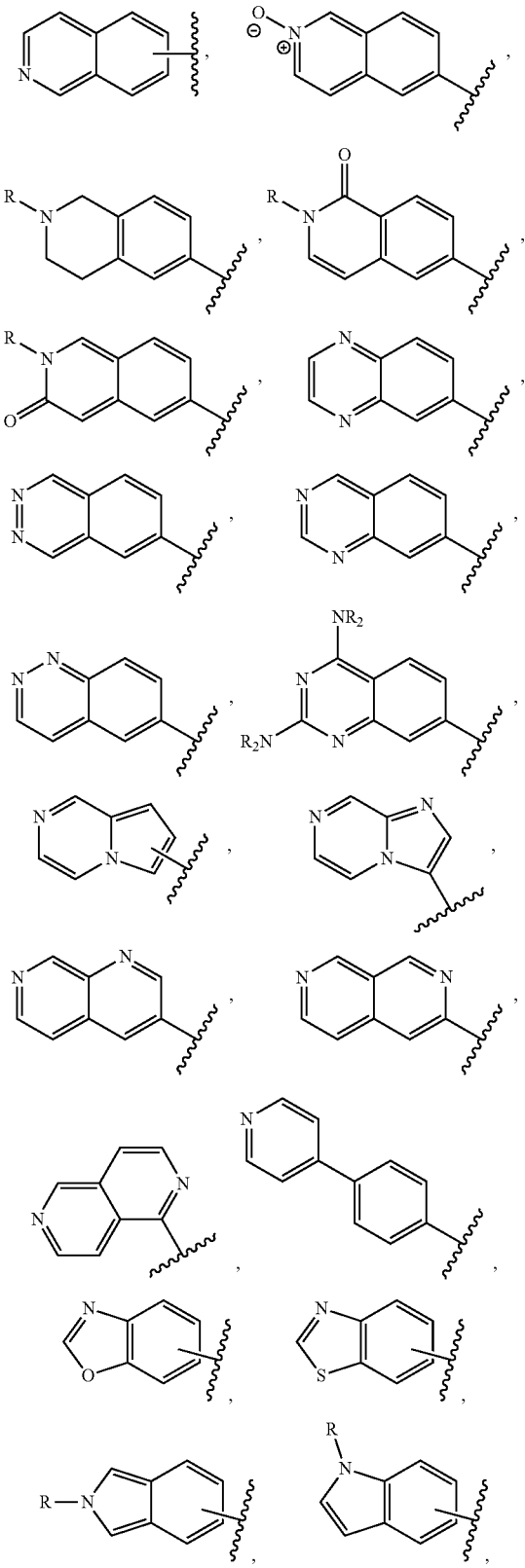

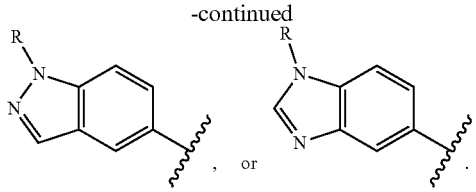

, or .

In certain embodiments, the invention relates to any one of the aforementioned compounds, wherein $R^3$ is —H, —OR$^4$, —NR$_2$, or halo.

In certain embodiments, the invention relates to any one of the aforementioned compounds, wherein $R^3$ is —H.

In certain embodiments, the invention relates to any one of the aforementioned compounds, wherein $R^3$ is —OR$^4$. In certain embodiments, the invention relates to any one of the aforementioned compounds, wherein $R^3$ is —OH. In certain embodiments, the invention relates to any one of the aforementioned compounds, wherein $R^3$ is —O-alkyl. In certain embodiments, the invention relates to any one of the aforementioned compounds, wherein $R^3$ is —OCH$_3$. In certain embodiments, the invention relates to any one of the aforementioned compounds, wherein $R^3$ is —O(CH$_2$CH$_2$—O—)$_x$—R. In certain embodiments, the invention relates to any one of the aforementioned compounds, wherein $R^3$ is —O(CH$_2$CH$_2$—O—)$_3$—R. In certain embodiments, the invention relates to any one of the aforementioned compounds, wherein $R^3$ is —O(CH$_2$CH$_2$—O—)$_x$-alkyl. In certain embodiments, the invention relates to any one of the aforementioned compounds, wherein $R^3$ is —O(CH$_2$CH$_2$—O—)$_x$—CH$_3$.

In certain embodiments, the invention relates to any one of the aforementioned compounds, wherein $R^3$ is —NR$_2$. In certain embodiments, the invention relates to any one of the aforementioned compounds, wherein $R^3$ is —NH$_2$. In certain embodiments, the invention relates to any one of the aforementioned compounds, wherein $R^3$ is

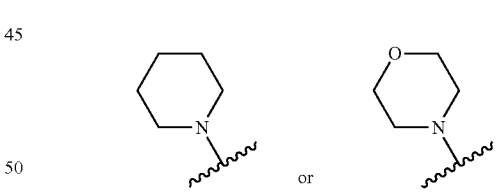

or .

In certain embodiments, the invention relates to any one of the aforementioned compounds, wherein $R^3$ is halo. In certain embodiments, the invention relates to any one of the aforementioned compounds, wherein $R^3$ is fluoro or chloro. In certain embodiments, the invention relates to any one of the aforementioned compounds, wherein $R^3$ is fluoro.

In certain embodiments, the invention relates to any one of the aforementioned compounds, wherein A is —O— or —S—. In certain embodiments, the invention relates to any one of the aforementioned compounds, wherein A is —O—. In certain embodiments, the invention relates to any one of the aforementioned compounds, wherein A is —S—.

In certain embodiments, the invention relates to a compound of Formula II

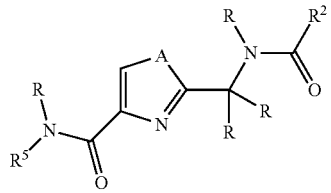

wherein, independently for each occurrence, $R^2$ is aryl or heteroaryl;

A is —O—, —S—, or —NR—;

R is —H, or alkyl; and $R^5$ is aryl or heteroaryl.

In certain embodiments, the invention relates to any one of the aforementioned compounds, wherein $R^2$ is aryl. In certain embodiments, the invention relates to any one of the aforementioned compounds, wherein $R^2$ is substituted aryl.

In certain embodiments, the invention relates to any one of the aforementioned compounds, wherein $R^2$ is substituted phenyl. In certain embodiments, the invention relates to any one of the aforementioned compounds, wherein $R^2$ is 4-substituted phenyl. In certain embodiments, the invention relates to any one of the aforementioned compounds, wherein $R^2$ is 3-substituted phenyl. In certain embodiments, the invention relates to any one of the aforementioned compounds, wherein $R^2$ is 3,4-disubstituted phenyl. In certain embodiments, the invention relates to any one of the aforementioned compounds, wherein $R^2$ is substituted aryl; and $R^2$ is substituted with —CN, tetrazolyl, alkyl, haloalkyl, halo, —OR, or —NR$_2$. In certain embodiments, the invention relates to any one of the aforementioned compounds, wherein $R^2$ is

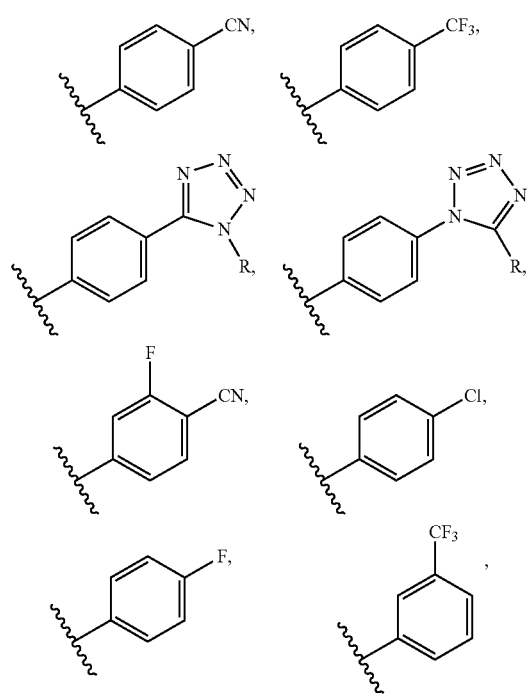

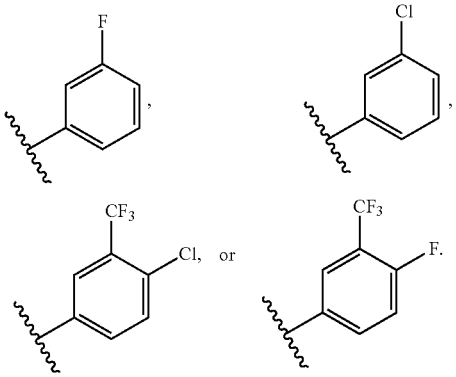

In certain embodiments, the invention relates to any one of the aforementioned compounds, wherein A is —O— or —S—. In certain embodiments, the invention relates to any one of the aforementioned compounds, wherein A is —O—. In certain embodiments, the invention relates to any one of the aforementioned compounds, wherein A is —S—.

In certain embodiments, the invention relates to any one of the aforementioned compounds, wherein R is —H. In certain embodiments, the invention relates to any one of the aforementioned compounds, wherein R is alkyl. In certain embodiments, the invention relates to any one of the aforementioned compounds, wherein R is methyl, ethyl, n-propyl, iso-propyl, n-butyl, sec-butyl, iso-butyl, or tert-butyl. In certain embodiments, the invention relates to any one of the aforementioned compounds, wherein R is iso-propyl.

In certain embodiments, the invention relates to any one of the aforementioned compounds, wherein $R^5$ is substituted or unsubstituted heteroaryl. In certain embodiments, the invention relates to any one of the aforementioned compounds, wherein $R^5$ is substituted heteroaryl. In certain embodiments, the invention relates to any one of the aforementioned compounds, wherein $R^5$ is unsubstituted heteroaryl. In certain embodiments, the invention relates to any one of the aforementioned compounds, wherein $R^5$ is pyridinyl, pyrazinyl, pyrimidinyl, pyridazinyl, or triazinyl. In certain embodiments, the invention relates to any one of the aforementioned compounds, wherein $R^5$ is

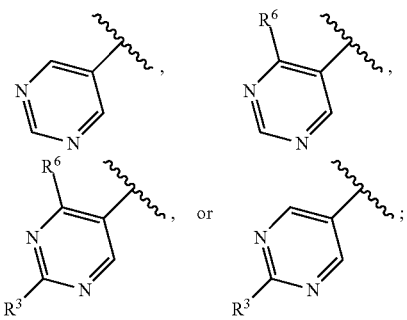

$R^3$ is —H, —OR$^4$, —NR$_2$, or halo; $R^6$ is halo, alkyl, haloalkyl, —OR$^4$, or —NR$^2$; and $R^4$ is —H, alkyl, or —(CR$_2$CR$_2$—O—)$_x$—R. In certain embodiments, the invention relates to any one of the aforementioned compounds, wherein $R^5$ is In certain embodiments, the invention relates to any one of the aforementioned compounds, wherein R⁵ is

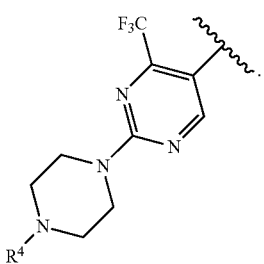

In certain embodiments, the invention relates to any one of the aforementioned compounds, wherein R⁵ is

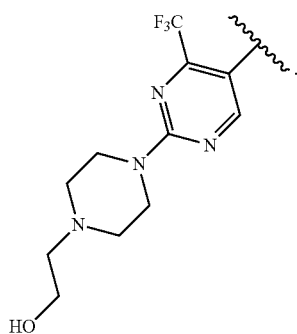

In certain embodiments, the invention relates to a compound of the following structure:

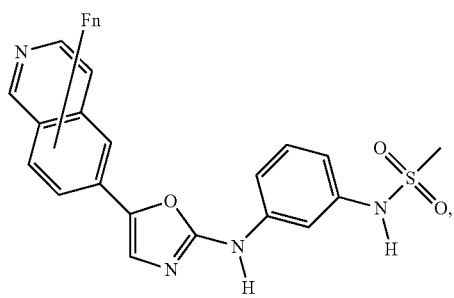

wherein n is 1, 2, 3, 4, 5, or 6.

In certain embodiments, the invention relates to a compound of Formula III

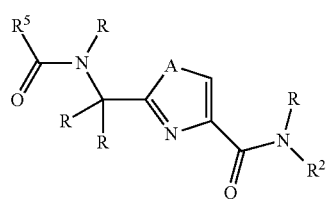

III wherein, independently for each occurrence,
R² is aryl or heteroaryl;
A is —O—, —S—, or —NR—;
R is —H, or alkyl; and
R⁵ is aryl or heteroaryl.

In certain embodiments, the invention relates to any one of the aforementioned compounds, wherein R² is aryl. In certain embodiments, the invention relates to any one of the aforementioned compounds, wherein R² is substituted aryl.

In certain embodiments, the invention relates to any one of the aforementioned compounds, wherein R² is substituted phenyl. In certain embodiments, the invention relates to any one of the aforementioned compounds, wherein R² is 4-substituted phenyl. In certain embodiments, the invention relates to any one of the aforementioned compounds, wherein R² is 3-substituted phenyl. In certain embodiments, the invention relates to any one of the aforementioned compounds, wherein R² is 3,4-disubstituted phenyl. In certain embodiments, the invention relates to any one of the aforementioned compounds, wherein R² is substituted aryl; and R² is substituted with —CN, tetrazolyl, alkyl, haloalkyl, halo, —OR, or —NR₂. In certain embodiments, the invention relates to any one of the aforementioned compounds, wherein R² is

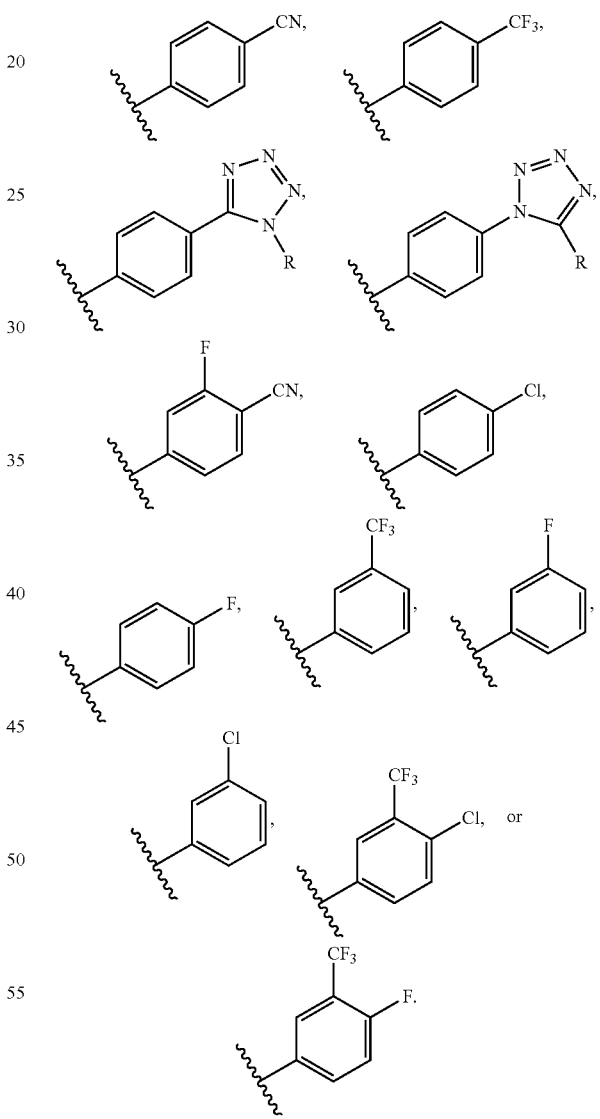

In certain embodiments, the invention relates to any one of the aforementioned compounds, wherein A is —O— or —S—. In certain embodiments, the invention relates to any one of the aforementioned compounds, wherein A is —O—. In certain embodiments, the invention relates to any one of the aforementioned compounds, wherein A is —S—.

In certain embodiments, the invention relates to any one of the aforementioned compounds, wherein R is —H. In certain embodiments, the invention relates to any one of the aforementioned compounds, wherein R is alkyl. In certain embodiments, the invention relates to any one of the aforementioned compounds, wherein R is methyl, ethyl, n-propyl, iso-propyl, n-butyl, sec-butyl, iso-butyl, or tert-butyl. In certain embodiments, the invention relates to any one of the aforementioned compounds, wherein R is iso-propyl.

In certain embodiments, the invention relates to any one of the aforementioned compounds, wherein $R^5$ is substituted or unsubstituted heteroaryl. In certain embodiments, the invention relates to any one of the aforementioned compounds, wherein $R^5$ is substituted heteroaryl. In certain embodiments, the invention relates to any one of the aforementioned compounds, wherein $R^5$ is unsubstituted heteroaryl. In certain embodiments, the invention relates to any one of the aforementioned compounds, wherein $R^5$ is pyridinyl, pyrazinyl, pyrimidinyl, pyridazinyl, or triazinyl. In certain embodiments, the invention relates to any one of the aforementioned compounds, wherein $R^5$ is

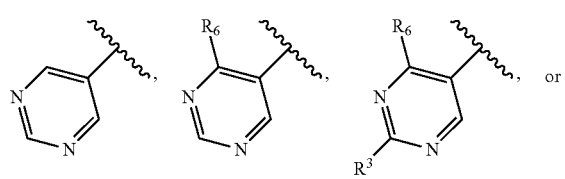

$R^3$ is —H, —$OR^4$, —$NR_2$, or halo; $R^6$ is halo, alkyl, haloalkyl, —$OR^4$, or —$NR^2$; and $R^4$ is —H, alkyl, or —$(CR_2CR_2$—O—$)_x$—R. In certain embodiments, the invention relates to any one of the aforementioned compounds, wherein $R^5$ is

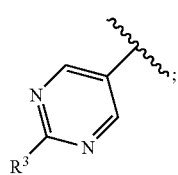

In certain embodiments, the invention relates to any one of the aforementioned compounds, wherein $R^5$ is

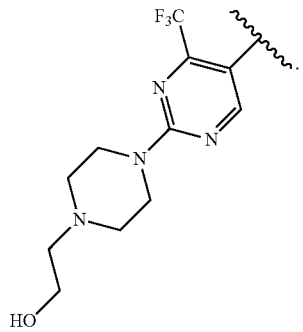

In certain embodiments, the invention relates to a compound selected from the group consisting of:

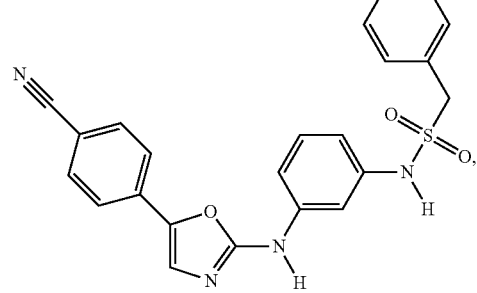

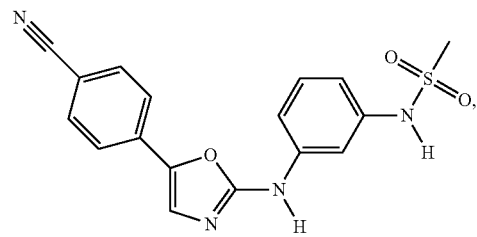

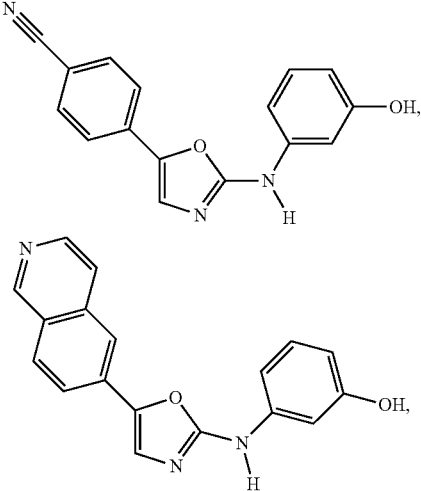

27
-continued
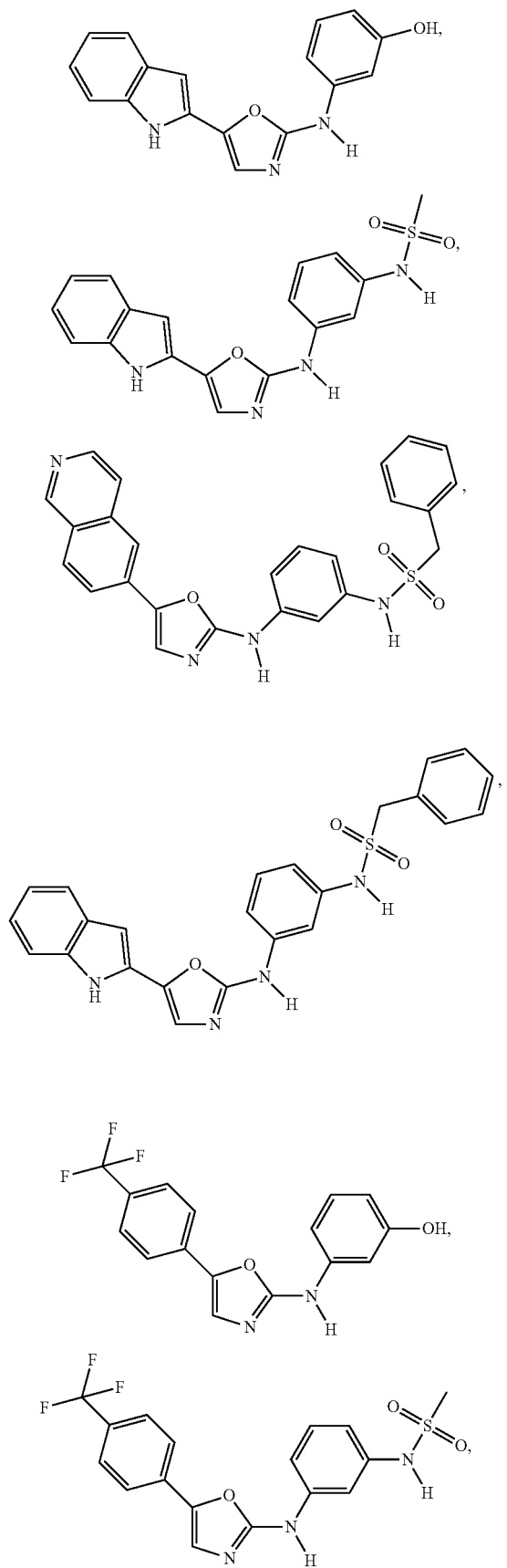
28
-continued
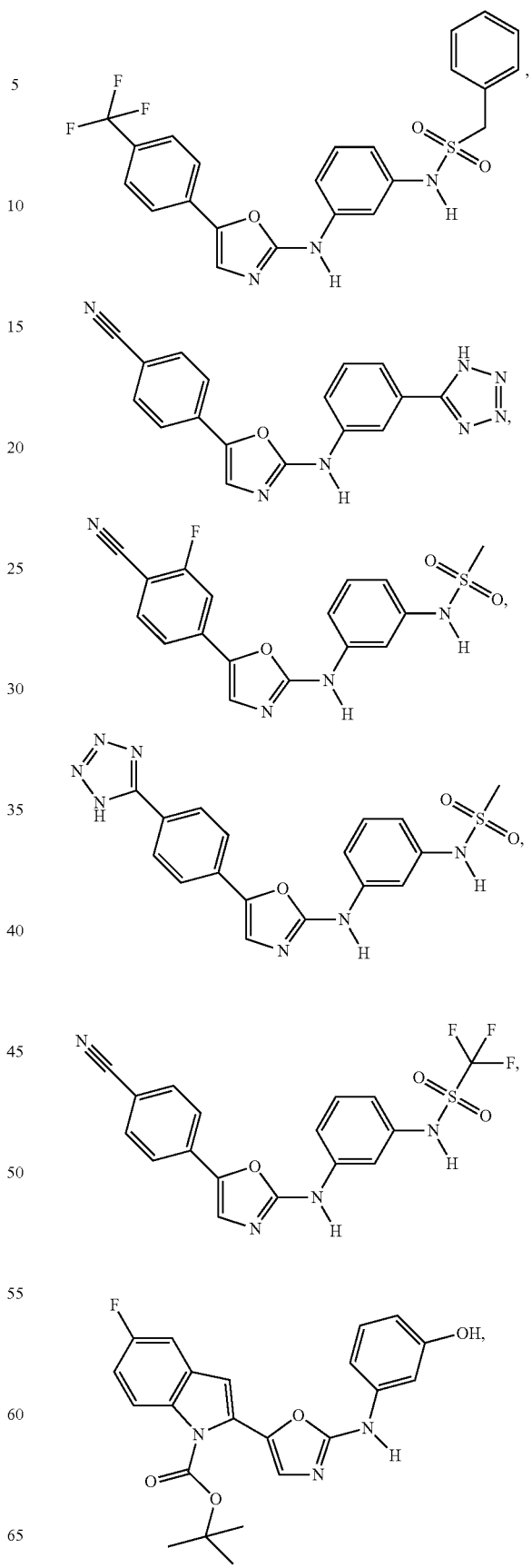

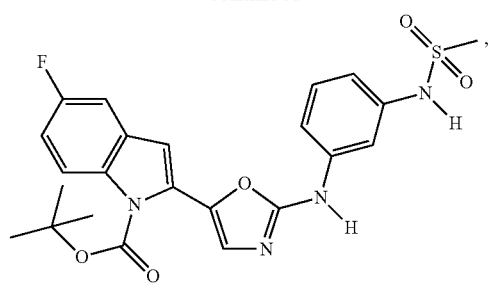
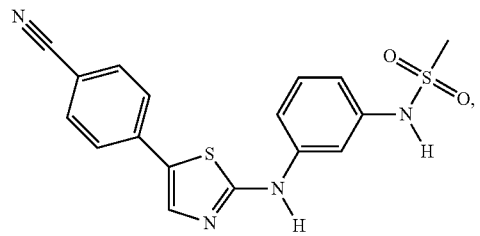
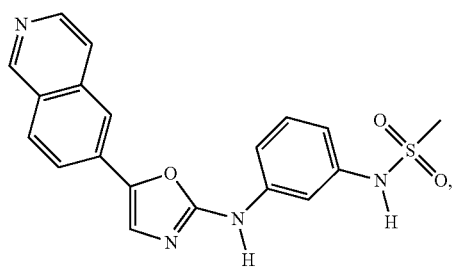
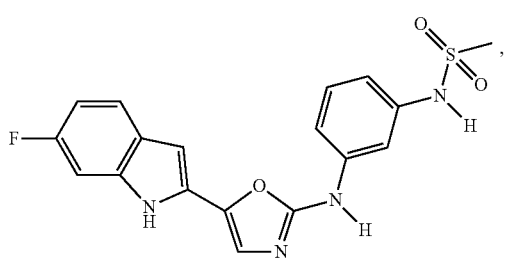
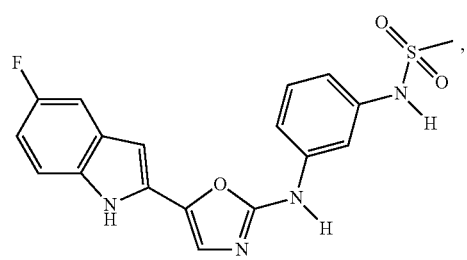
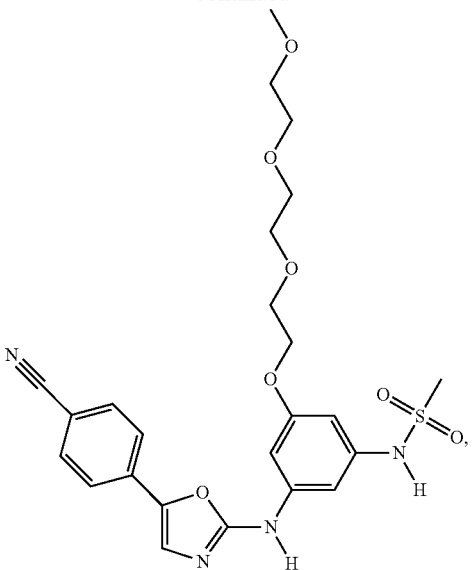
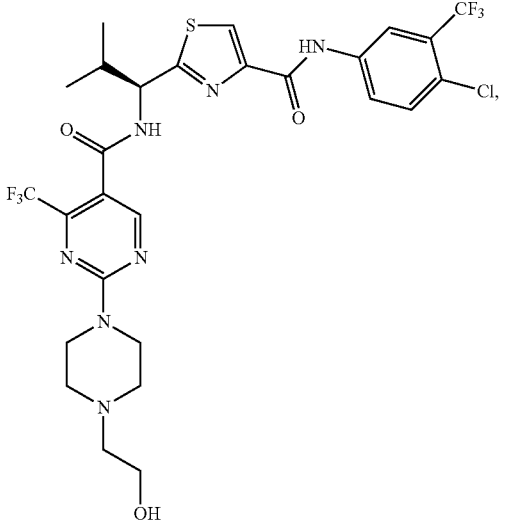
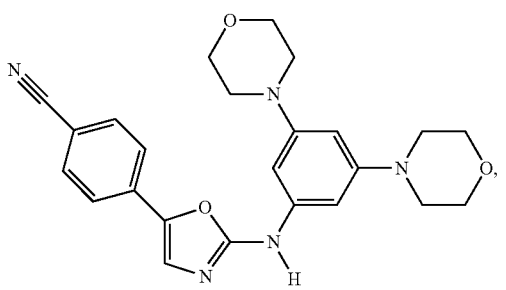
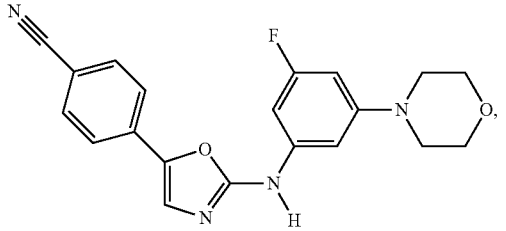

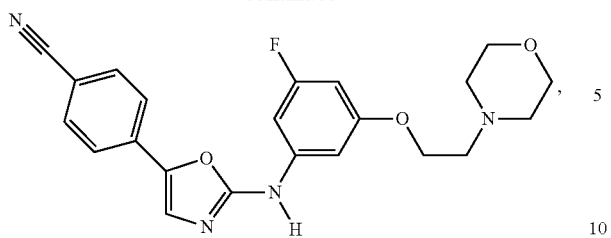
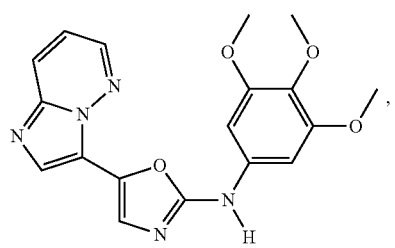
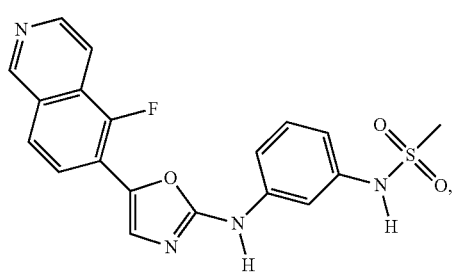
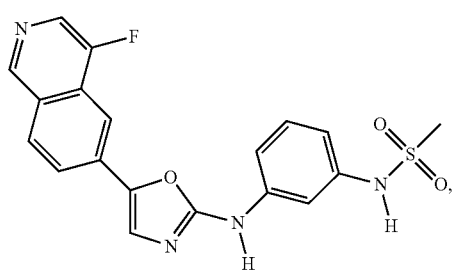
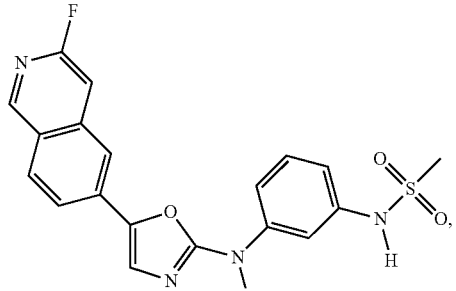
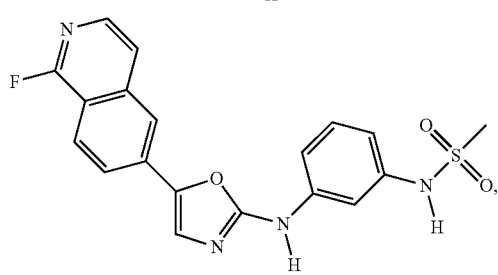
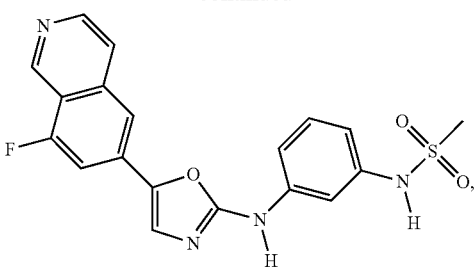
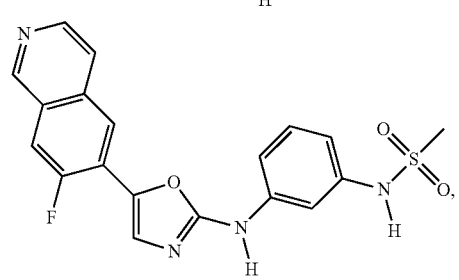
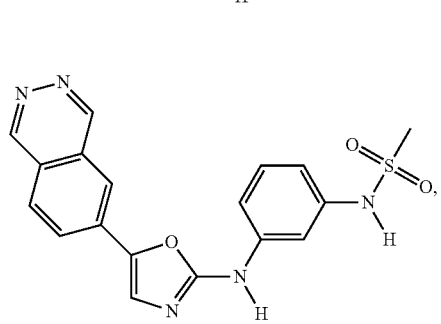
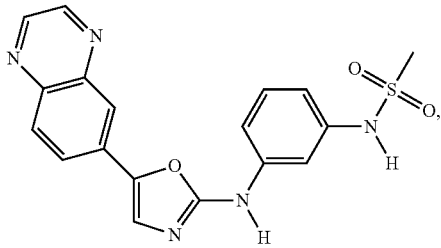
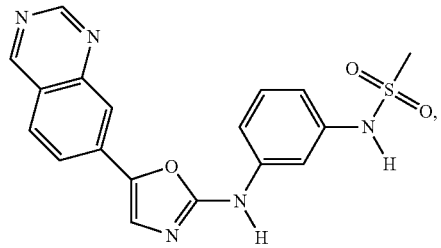
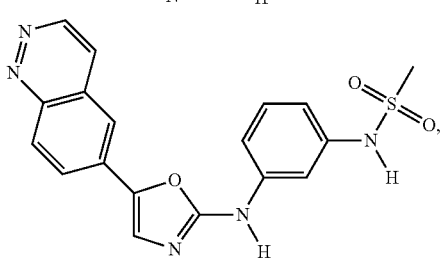

33
-continued
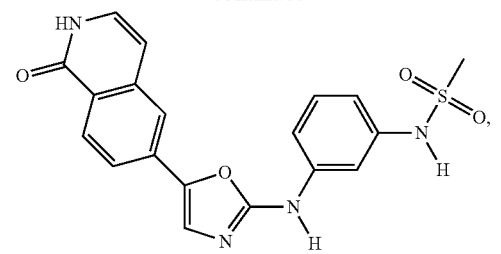
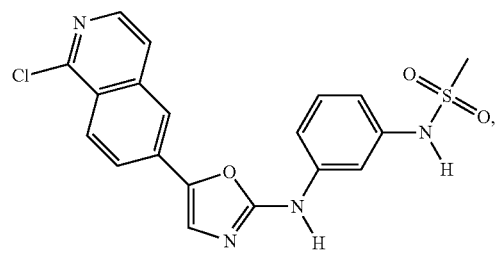
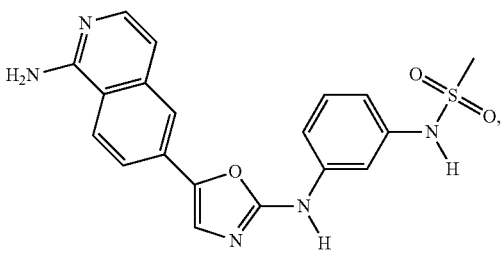
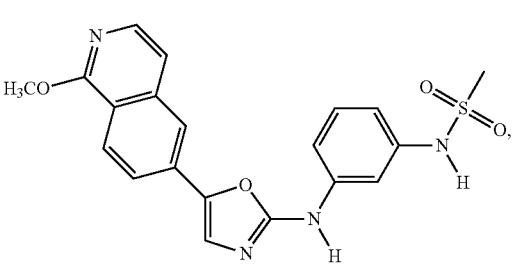
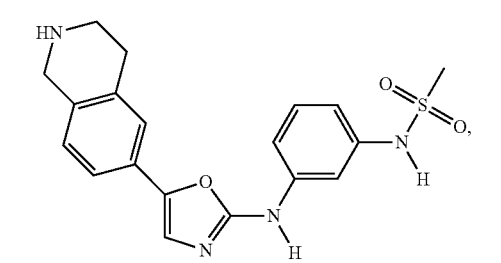
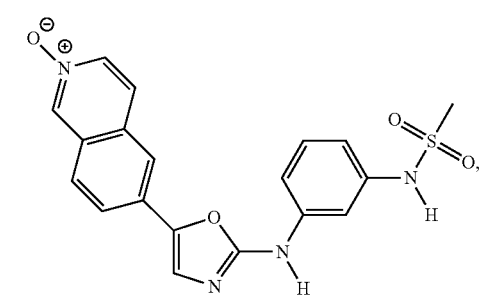
34
-continued
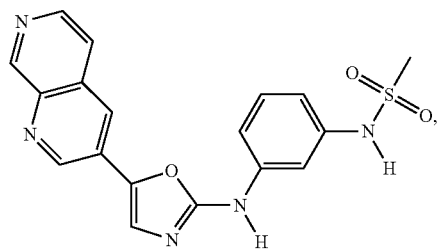
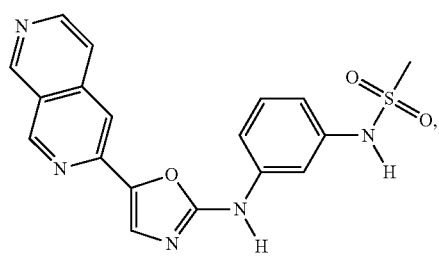
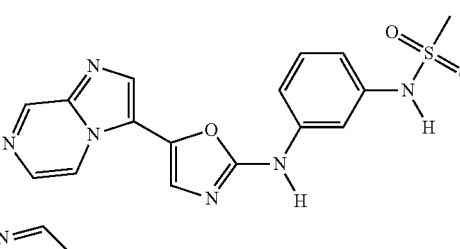
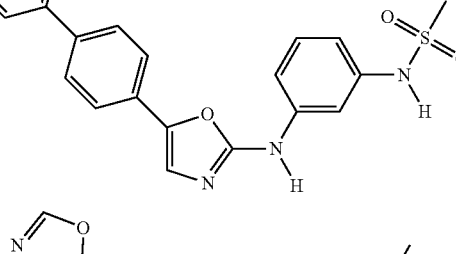
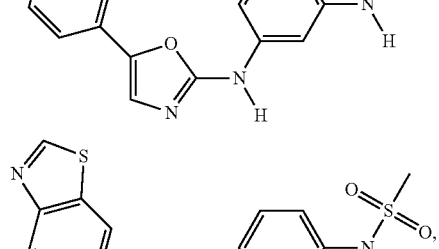
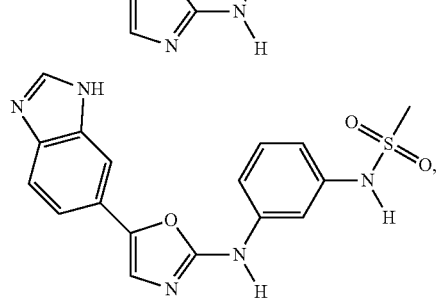

-continued

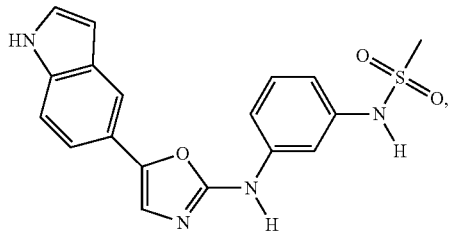

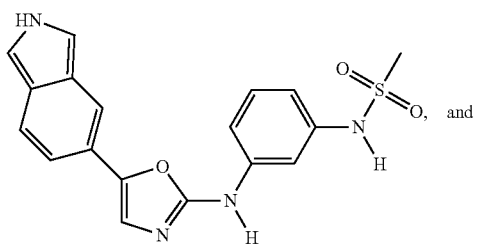

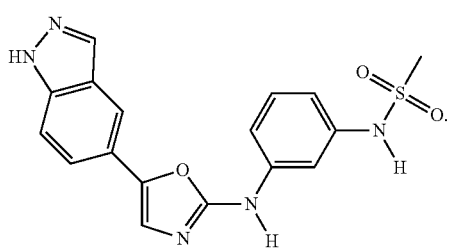 [SMILES: CS(=O)(=O)Nc1cccc(Nc2ncc(-c3ccc4[nH]ncc4c3)o2)c1]

In certain embodiments, the invention relates to a compound of the following structure:

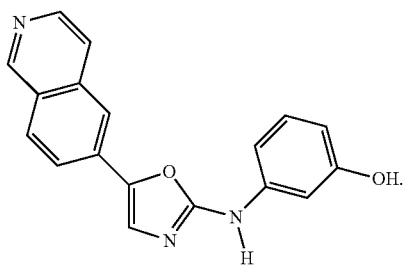 [SMILES: Oc1cccc(Nc2ncc(-c3ccc4cnccc4c3)o2)c1]

In certain embodiments, the invention relates to a compound of the following structure:

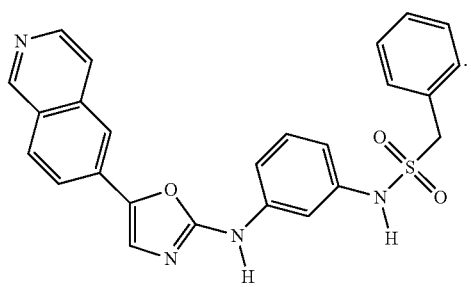 [SMILES: O=S(=O)(Cc1ccccc1)Nc1cccc(Nc2ncc(-c3ccc4cnccc4c3)o2)c1 ; "."]

In certain embodiments, the invention relates to a compound of the following structure:

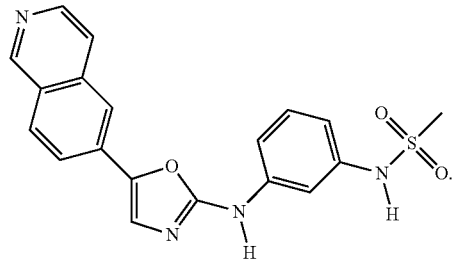 [SMILES: CS(=O)(=O)Nc1cccc(Nc2ncc(-c3ccc4cnccc4c3)o2)c1]

In certain embodiments, the invention relates to a compound of the following structure:

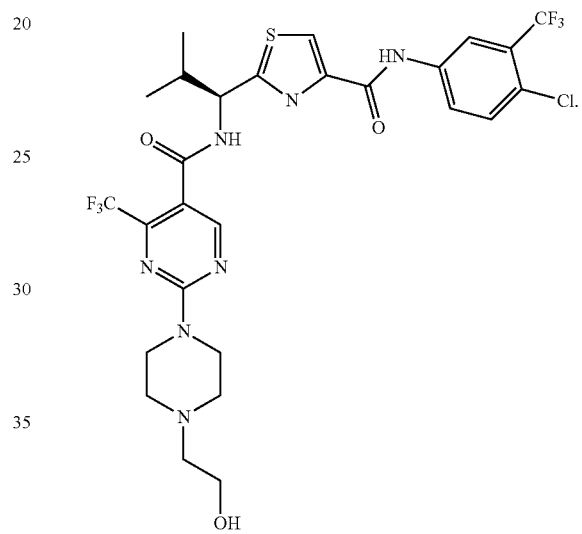

In certain embodiments, the invention relates to any one of the aforementioned compounds, provided the compound is not

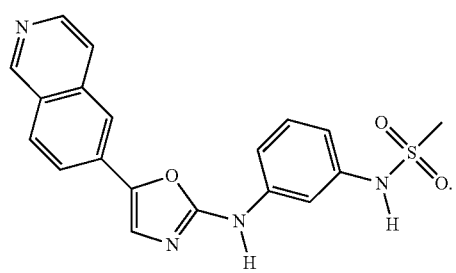 [SMILES: CS(=O)(=O)Nc1cccc(Nc2ncc(-c3ccc4cnccc4c3)o2)c1]

Exemplary Methods of the Invention

In certain embodiments, the invention relates to a method of treating cancer, comprising administering to a mammal in need thereof a therapeutically effective amount of any one of the aforementioned compounds.

In certain embodiments, the invention relates to any one of the aforementioned methods,
wherein the cancer is prostate cancer, lung cancer (e.g., non-small cell lung cancer), breast cancer, colon cancer, leukemia, central nervous system (CNS) cancer, melanoma, ovarian cancer, or renal cancer.

In certain embodiments, the invention relates to any one of the aforementioned methods, wherein the mammal is human.

In certain embodiments, and not wishing to be bound by any particular theory, the aforementioned compounds are believed to have anticancer activity as a result of inhibition of the protein kinase CDK2, CDK4, or VEGFR2 and its effect on selected cell lines whose growth is dependent on CDK2, CDK4, or VEGFR2 kinase activity.

In certain embodiments, the invention relates to a method of treating a disorder mediated by inappropriate VEGFR2 or CDK activity.

In certain embodiments, the inappropriate CDK activity referred to herein may be any CDK activity that deviates from the normal CDK activity expected in a particular mammalian subject. In certain embodiments, inappropriate CDK activity may take the form of, for instance, an abnormal increase in activity, or an aberration in the timing- and or control of CDK activity. In certain embodiments, such inappropriate activity may result from overexpression or mutation of the protein kinase or ligand leading to inappropriate or uncontrolled activation of the receptor. In certain embodiments, unwanted CDK activity may reside in an abnormal source, such as a malignancy. In certain embodiments, the level of CDK activity does not have to be abnormal to be considered inappropriate, rather the activity derives from an abnormal source.

In certain embodiments, the inappropriate VEGFR2 activity referred to herein may be any VEGFR2 activity that deviates from the normal VEGFR2 activity expected in a particular mammalian subject. In certain embodiments, inappropriate VEGFR2 activity may take the form of an abnormal increase in activity, or an aberration in the timing and or control of VEGFR2 activity. In certain embodiments, such inappropriate activity may result from overexpression or mutation of the protein kinase or ligand leading to inappropriate or uncontrolled activation of the receptor. In certain embodiments, unwanted VEGFR2 activity may reside in an abnormal source, such as a malignancy. In certain embodiments, the level of VEGFR2 activity does not have to be abnormal to be considered inappropriate, rather the activity derives from an abnormal source.

In certain embodiments, the invention relates to a method of regulating, modulating, or inhibiting CDK2 and/or CDK4 for the prevention and/or treatment of disorders related to unregulated CDK activity, and/or inhibiting VEGFR2 for the prevention and/or treatment of disorders related to unregulated VEGFR2 activity. In certain embodiments, the compounds of the present invention can be used in the treatment of certain forms of cancer. In certain embodiments, the compounds of the present invention can be used to provide additive or synergistic effects with certain existing cancer chemotherapies and radiation, and/or be used to provide protection from the epithelial cytotoxic effects of certain existing cancer chemotherapies and radiation.

In certain embodiments, the invention relates to a method of treating a disease, comprising administering to a mammal in need thereof a therapeutically effective amount of any one of the aforementioned compounds, wherein the disease is characterized by cellular proliferation; and the disease is associated with neo-vascularization or vascular permeability. In certain embodiments, the disease includes, but is not limited to: blood vessel proliferative disorders including arthritis and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, proliferative retinopathies, organ transplant rejection and glomerulopathies; and metabolic disorders include psoriasis, diabetes mellitus, chronic wound healing, inflammation and neurodegenerative diseases.

EXEMPLIFICATION

The invention now being generally described, it will be more readily understood by reference to the following examples, which are included merely for purposes of illustration of certain aspects and embodiments of the present invention, and are not intended to limit the invention.

Example 1

Materials, Techniques, and General Procedures

The materials, techniques, and general procedures apply to the remainder of the Examples. Reactions were monitored by thin layer chromatography (TLC) with 0.25 mm E. Merck precoated silica gel plates (60 F254). Visualization was accomplished with either UV light, or by immersion in solutions of ninhydrin, β-Naphthal, p-anisaldehyde, or phosphomolybdic acid (PMA) followed by heating on a hot plate for about 10 s. Purification of reaction products was carried out by MPLC (Biotage) chromatography using (220-440 mesh) or by re-crystallization where it is necessary. Formations of products were confirmed by using LC/MS (Applied Biosystem). Various synthetic methodologies may be found in WO 2004/032882, WO 2006/122250, WO 2009/011880, WO 2007/076161, and WO 2009/012242, all of which are hereby incorporated by reference in their entireties.

Example 2

Synthesis of N-(3-((5-(4-cyanophenyl)oxazol-2-yl)amino)phenyl)-1-phenylmethanesulfonamide

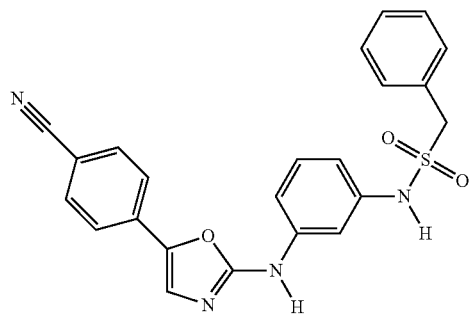 [SMILES: N#Cc1ccc(-c2cnc(Nc3cccc(NS(=O)(=O)Cc4ccccc4)c3)o2)cc1]

N-(3-((5-(4-cyanophenyl)oxazol-2-yl)amino)phenyl)-1-phenylmethanesulfonamide

CH1149

Figure 2:
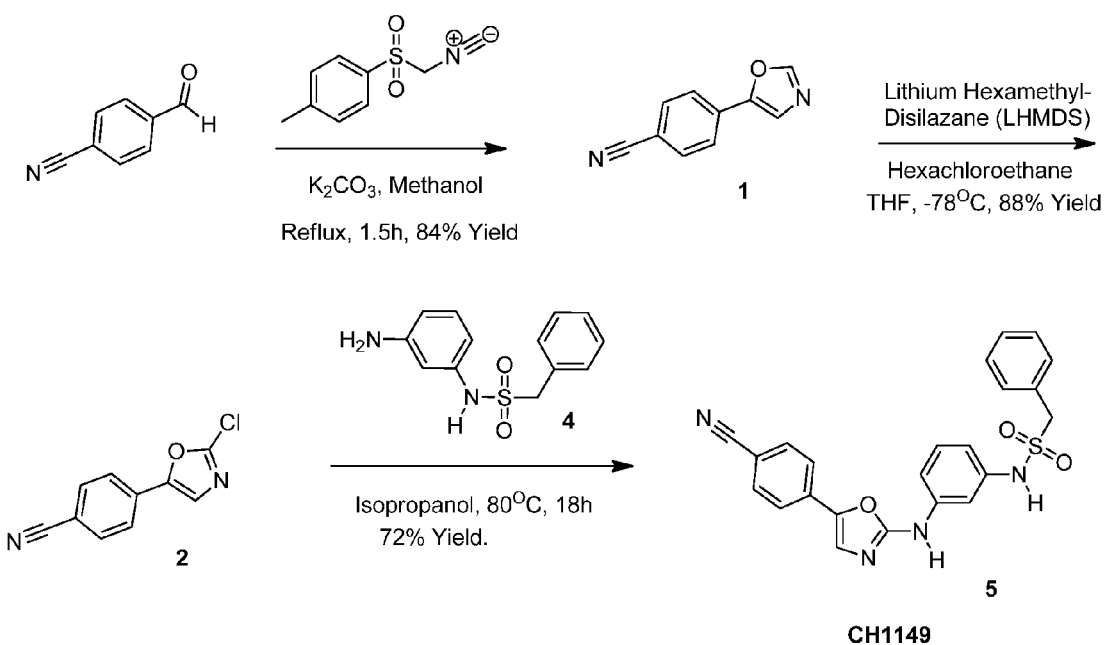
FIG. 2 depicts an exemplary synthetic route for the preparation of a compound of the invention.
Figure 3:
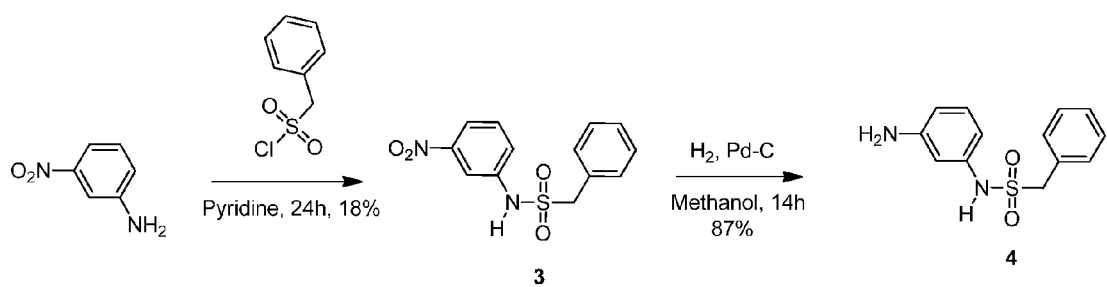
FIG. 3 depicts an exemplary synthetic route for the preparation of an intermediate compound of the invention.
Figure 4:
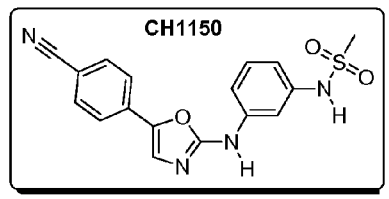
FIG. 4 depicts assay results for a compound of the invention.

The general synthetic scheme for CH1149 (compound 5) is found in FIG. 2. The synthetic scheme depicting the synthesis of sulfonamide intermediate 4 is depicted in FIG. 3.

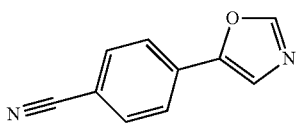 [SMILES: N#Cc1ccc(-c2cnco2)cc1]

Compound 1: 4-(oxazol-5-yl)benzonitrile

To a 500 mL round-bottom flask was added 4-cyanobenzaldehyde (5.00 g, 38.1 mmol), methanol (200 mL), p-toluene sulfonylmethyl isocyanide (8.33 g, 42.66 mmol), followed by potassium carbonate (6.85 g, 49.56 mmol). The reaction mixture was stirred at reflux for about 1.5 hour and followed by TLC. The solvent was then evaporated and saturated aq.NaHCO$_3$ was added. The resultant suspension was extracted with CH$_2$Cl$_2$ (3×100 mL). Combined organic layers were washed with brine, dried (anhydrous Na$_2$SO$_4$), and concentrated to leave a yellow solid. Trituration with hexane afforded a solid which was collected by filtration and dried. Crude product was further purified by re-crystallization using hot-CH$_2$Cl$_2$ and cold-hexane to afford title compound 1 (5.48 g, 84% yield). MS (ES) m/z 171 (M+H$^+$).

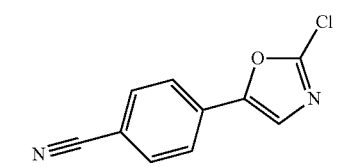 [SMILES: N#Cc1ccc(-c2cnc(Cl)o2)cc1]

Compound 2: 4-(2-chlorooxazol-5-yl)benzonitrile

LiHMDS (1.06 M in THF, 21.0 mL, 21.15 mmol) was added to a solution of 1 (3.00 g, 17.64 mmol) in THF (100 mL) at −78° C., and the mixture was stirred at −78° C. for 1 h. A solution of hexachloroethane (6.27 g, 26.48 mmol) in THF (9 mL) was added at −78° C., and the mixture was stirred at −78° C. for 2 h and allowed to warm to room temperature and stirred for 14 h. The reaction was quenched by adding EtOAc:H$_2$O (50 mL:15 mL), and then extracted with ethyl acetate. The extracts were washed with brine, dried (Na$_2$SO$_4$) and concentrated. The product was purified by column chromatography (Acetone/hexane as an eluent) to provide 2 (3.15 g, 88% yield) as white solid. MS (ES) m/z 205 (M+H$^+$).

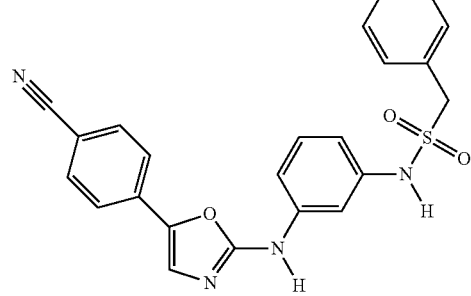

Compound 5: N-(3-((5-(4-cyanophenyl)oxazol-2-yl)amino)phenyl)-1-phenylmethanesulfonamide A mixture of 4-(2-chlorooxazol-5-yl)benzonitrile 2 (0.20 g, 0.98 mmol) and N-(3-aminophenyl)-1-phenylmethanesulfonamide 4 (0.256 g, 0.98 mmol) in 2-propanol (20 mL) was heated to 80° C. for 18 h with stirring. Upon cooling, a white solid precipitated out which was filtered off, washed with 2-propanol, and dried. This was then triturated with ether and filtered to yield the title product, a white solid, as the hydrochloride salt of 5 (0.15 g, 36%). Free amine containing filtrate was evaporated and silica column purified (Biotage) (Acetone/hexane as an eluent) to provide 5 (0.15 g, 36% yield) as pale yellow solid. MS (ES) m/z 431 (M+H$^+$).

(NOTE: In most cases, the product deposits as the hydrochloride salt and free amine; however, when the aniline has phenoxy or sulfonamide substitution, the free base is recovered. Hydrochloride salts can be converted to the free base by partitioning between ethyl acetate and aqueous sodium bicarbonate and overnight stirring.)

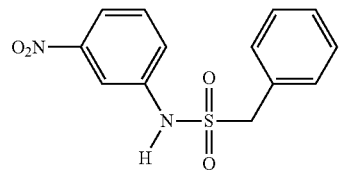 [SMILES: Nc1cccc(NS(=O)(=O)Cc2ccccc2)c1]

Compound 3: N-(3-nitrophenyl)-1-phenylmethanesulfonamide

3-Nitroaniline (4.00 g, 28.96 mmol) was treated with pyridine (1.1 equiv, 4.5 g, 56.96 mmol) in THF at room temperature for 10 min, followed by the addition of phenylmethanesulfonyl chloride (1.0 equiv, 6.05 g, 1.0 mmol) at 0° C. The reaction mixture was warmed to room temperature for 24 h. The reaction was quenched with aqueous NaHCO$_3$ (saturated aqueous) and extracted with CH$_2$Cl$_2$. The organic phase was dried over Na$_2$SO$_4$. After evaporation of organic solvent, the crude product was purified by column (Biotage) chromatography (Acetone/hexane as an eluent) to afford compound 3 (1.51 g, 18% yield). MS (ES) m/z 293 (M+H$^+$).

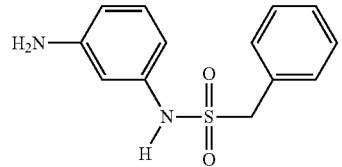

Compound 4: N-(3-aminophenyl)-1-phenylmethanesulfonamide

Nitro-substituted amide 3 (0.5 g, 1.71 mmol) was dissolved in methanol (20 mL) treated with H$_2$ (balloon pressure) for 14 h in the presence of Pd/C (catalytic, 100 mg). The reaction was monitored by TLC until the starting material was no longer detected. The Pd/C residue was removed by filtration over celite pad, followed by rotary evaporation of the solvent obtained 0.39 g of 4 (87% yield). The crude product was further used without further purification. MS (ES) m/z 263 (M+H$^+$).

Example 3

Synthesis of N-(3-((5-(4-cyanophenyl)oxazol-2-yl)amino)phenyl)methanesulfonamide

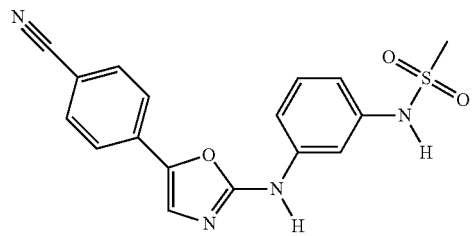 [SMILES: CS(=O)(=O)Nc1cccc(Nc2ncc(-c3ccc(C#N)cc3)o2)c1]

N-(3-((5-(4-cyanophenyl)oxazol-2-yl)amino)phenyl)methanesulfonamide

CH1150

Figure 5:
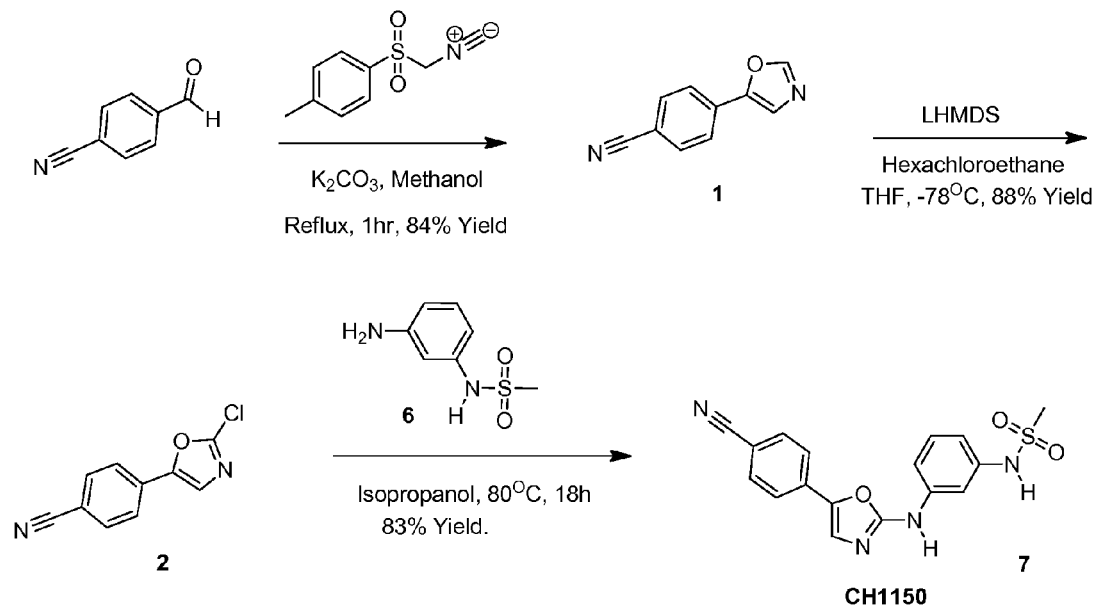
FIG. 5 depicts an exemplary synthetic route for the preparation of a compound of the invention.
Figure 6:
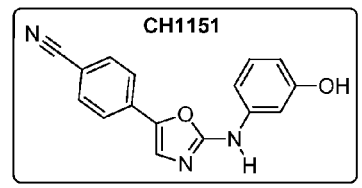
FIG. 6 depicts assay results for a compound of the invention.

The general synthetic scheme for CH1150 (compound 7) is found in FIG. 5. Compound 1 and compound 2 were prepared as described in Example 2, above.

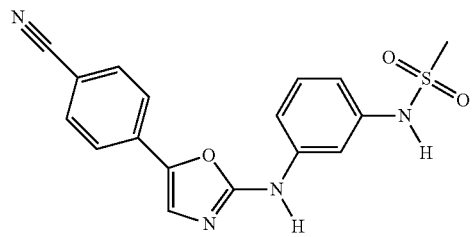

Compound 7: N-(3-((5-(4-cyanophenyl)oxazol-2-yl)amino)phenyl)methanesulfonamide

A mixture of 4-(2-chlorooxazol-5-yl)benzonitrile 2 (0.20 g, 0.98 mmol) and commercially available N-(3-aminophenyl)methanesulfonamide 6 (0.182 g, 0.98 mmol) in 2-propanol (20 mL) was heated to 80° C. for 18 h with stirring. Upon cooling, a white solid precipitated out which was filtered off, washed with 2-propanol, and dried. This was then triturated with ether and filtered to yield the title product, a white solid, as the hydrochloride salt of 7 (0.14 g, 40%). Free amine containing filtrate was evaporated and silica column purified (Biotage) (Acetone/hexane as an eluent) to provide 7 (0.151 g, 44% yield) as pale yellow solid. MS (ES) m/z 355 (M+H$^+$).

Example 4

Synthesis of 4-(2-((3-hydroxyphenyl)amino)oxazol-5-yl)benzonitrile

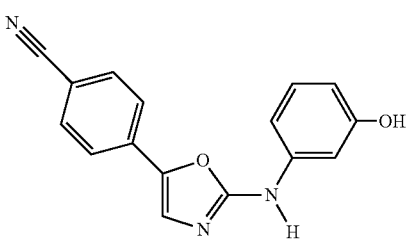 [SMILES: N#Cc1ccc(-c2cnc(Nc3cccc(O)c3)o2)cc1]

4-(2-((3-hydroxyphenyl)amino)oxazol-5-yl)benzonitrile

CH1151

Figure 7:
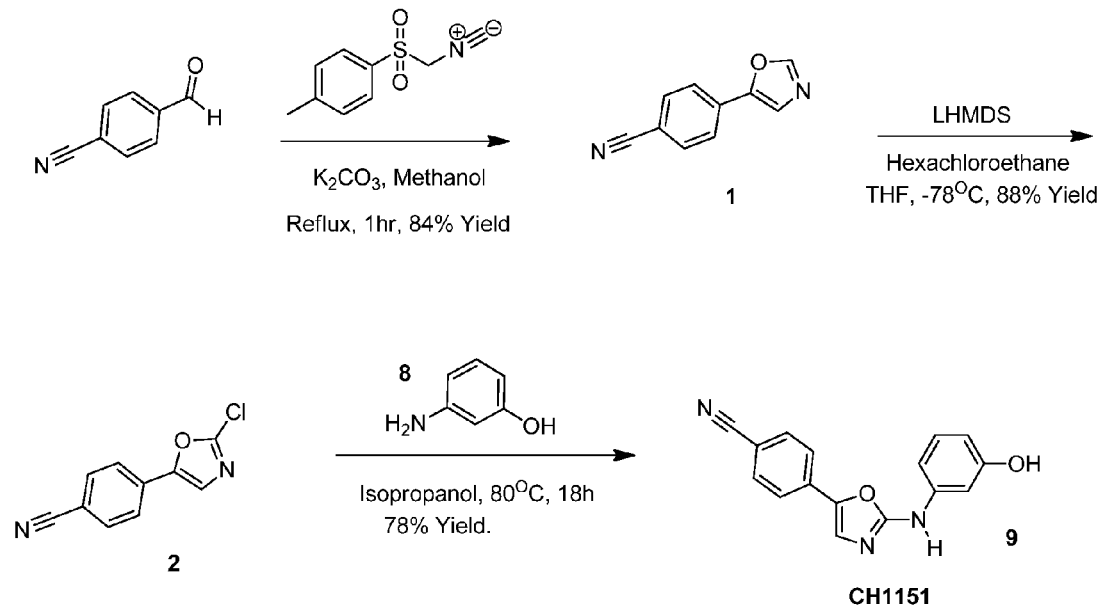
FIG. 7 depicts an exemplary synthetic route for the preparation of a compound of the invention.
Figure 8:
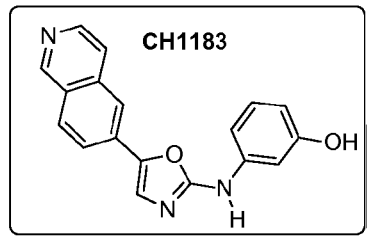
FIG. 8 depicts assay results for a compound of the invention.

The general synthetic scheme for CH1151 (compound 9) is found in FIG. 7. Compound 1 and compound 2 were prepared as described in Example 2, above.

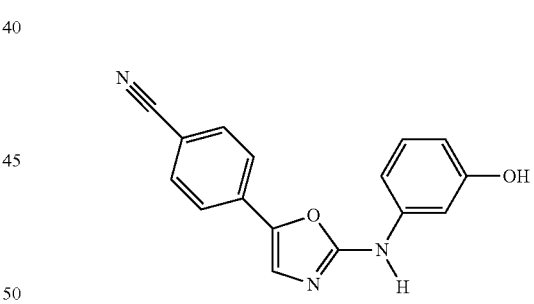

Compound 9: 4-(2-((3-hydroxyphenyl)amino)oxazol-5-yl)benzonitrile

A mixture of 4-(2-chlorooxazol-5-yl)benzonitrile 2 (0.21 g, 1.02 mmol) and commercially available 3-aminophenol 8 (0.112 g, 0.28 mmol) in 2-propanol (20 mL) was heated to 80° C. for 18 h with stirring. Upon cooling, solvent was evaporated and silica column purified (Biotage) (Acetone/hexane as an eluent) to provide 9 (0.217 g, 78% yield) as pale yellow solid. MS (ES) m/z 278 (M+H$^+$).

(NOTE: In this case, the entire product is isolated as free base due to phenolic functionality. No hydrochloride salt is observed)

Example 5

Synthesis of 3-((5-(isoquinolin-6-yl)oxazol-2-yl)amino)phenol

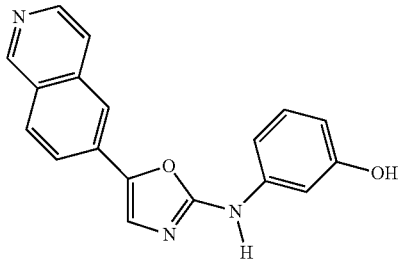 [SMILES: Oc1cccc(Nc2ncc(-c3ccc4cnccc4c3)o2)c1]

3-((5-(isoquinolin-6-yl)oxazol-2-yl)amino)phenol

CH1183

Figure 9:
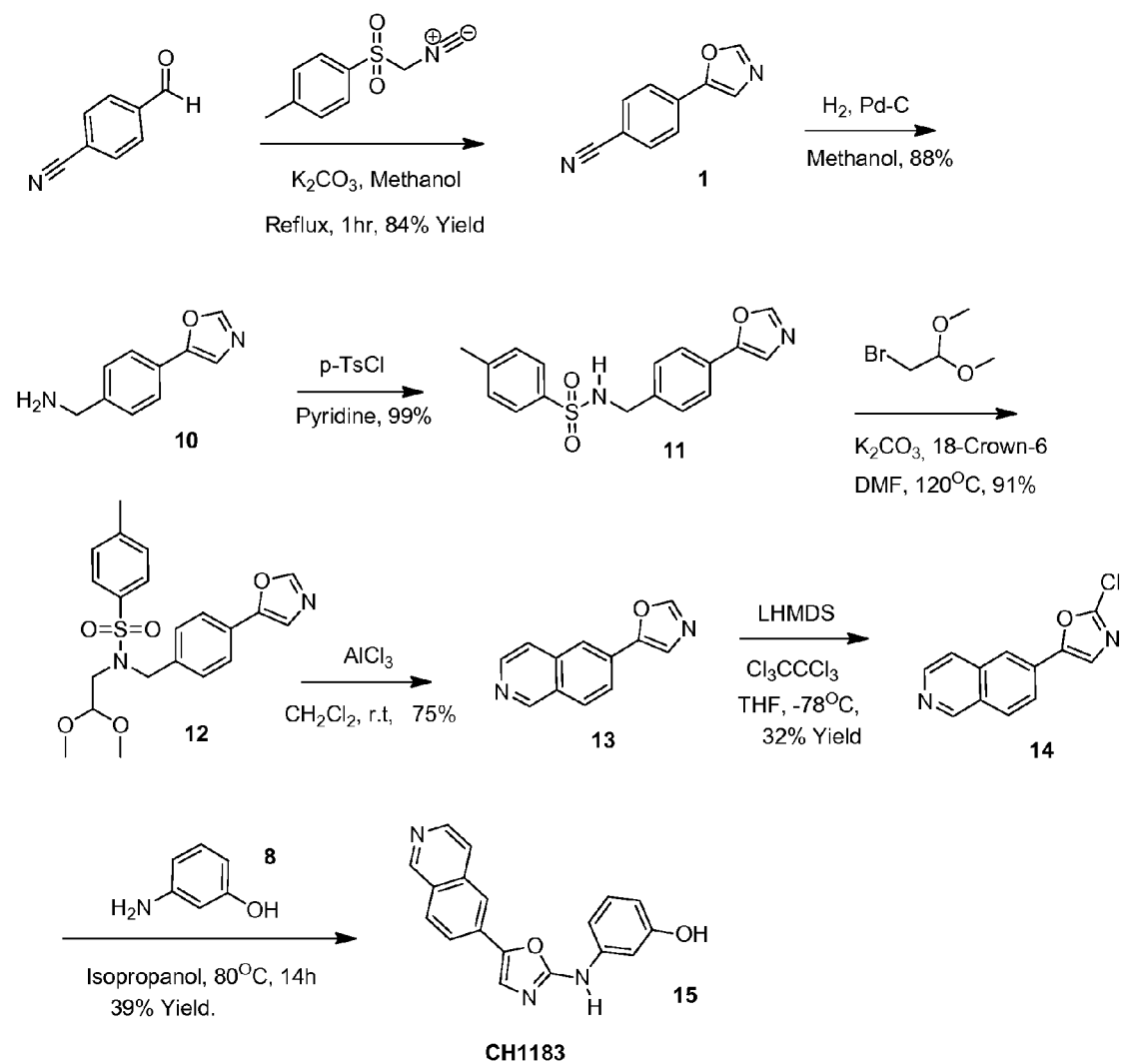
FIG. 9 depicts an exemplary synthetic route for the preparation of a compound of the invention.
Figure 10:
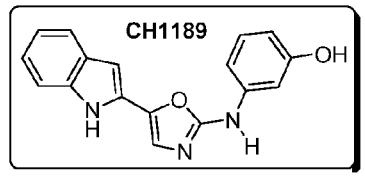
FIG. 10 depicts assay results for a compound of the invention.

The general synthetic scheme for CH1183 (compound 15) is found in FIG. 9. Compound 1 was prepared as described in Example 2, above.

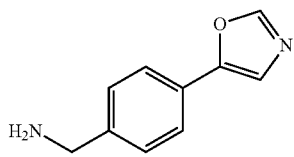 [SMILES: NCc1ccc(-c2cnco2)cc1]

Compound 10: (4-(oxazol-5-yl)phenyl)methanamine 4-(oxazol-5-yl)benzonitrile 1 (1.50 g, 8.82 mmol) was dissolved in methanol (20 mL) treated with $H_2$ (balloon pressure) for 14 h in the presence of Pd/C (catalytic, 150 mg). The reaction was monitored by TLC until the starting material was no longer detected. The Pd/C residue was removed by filtration over celite pad, followed by rotary evaporation of the solvent obtained 1.34 g of 10 (88% yield). The crude product was further used without further purification. MS (ES) m/z 175 (M+H$^+$).

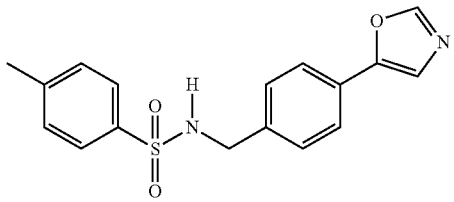 [SMILES: Cc1ccc(S(=O)(=O)NCc2ccc(-c3cnco3)cc2)cc1]

Compound 11: 4-methyl-N-(4-(oxazol-5-yl)benzyl)benzenesulfonamide

Crude (4-(oxazol-5-yl)phenyl)methanamine 10 (1.34 g, 7.70 mmol) was dissolved in anhydrous pyridine (30 mL). At room temperature p-toluenesulfonyl-chloride (1.75 g, 8.47 mmol) was added and the solution was stirred at ambient temperature for 6 hours. The reaction was quenched with aq. NaHCO$_3$ and the solvent was evaporated. Residue was diluted with CH$_2$Cl$_2$, washed with 1N HCl and aq. NaHCO$_3$, organic layer was dried over anhydrous sodium sulfate and evaporated. Final silica gel chromatography (MPLC, Biotage) using Hexane:Acetone as an eluent gave 2.50 g (99% yield) of the title compound 11. MS (ES) m/z 329 (M+H$^+$).

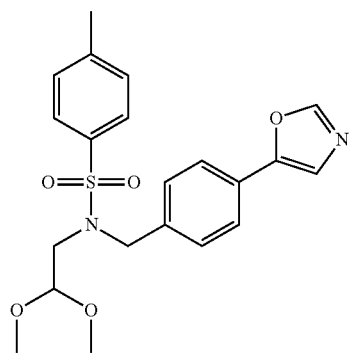 [SMILES: COC(CN(Cc1ccc(-c2cnco2)cc1)S(=O)(=O)c1ccc(C)cc1)OC]

Compound 12: N-(2,2-dimethoxyethyl)-4-methyl-N-(4-(oxazol-5-yl)benzyl)benzenesulfonamide To stirred solution of 4-methyl-N-(4-(oxazol-5-yl)benzyl)benzenesulfonamide 11 (2.5 g, 7.62 mmol) in anhydrous DMF (15 mL) were added bromoacetaldehyde dimethylacetal (1.54 mL, 9.14 mmol), potassium carbonate (1.02 g, 22.86 mmol), 18-crown-6 (0.2 g, 1.52 mmol). The resulting mixture was heated at 120° C. for 12 hours. Reaction was quenched with aq. NaHCO$_3$ and the solvent was evaporated. Residue was diluted with CH$_2$Cl$_2$, washed with water, brine, organic layer was dried over anhydrous sodium sulfate and evaporated. Final silica gel chromatography (MPLC, Biotage) using Hexane:Acetone as an eluent gave 2.90 g (91% yield) of the title compound 12. MS (ES) m/z 417 (M+H$^+$).

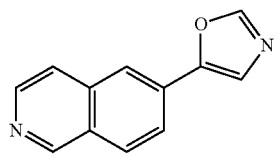 [SMILES: c1cc2cc(-c3cnco3)ccc2cn1]

Compound 13: 5-(isoquinolin-6-yl)oxazole

To a stirred suspension of AlCl$_3$ (0.90 g, 6.74 mmol) in anhydrous dichloromethane (40 mL) a solution of N-(2,2-dimethoxyethyl)-4-methyl-N-(4-(oxazol-5-yl)benzyl)benzene-sulfonamide 12 (0.565 g, 1.35 mmol) in CH$_2$Cl$_2$ was added and the reaction was stirred at room temperature for 1 hour. After standing for overnight, the reaction mixture was poured into ice, the organic layer was separated and the aqueous layer was extracted with $CH_2Cl_2$. The combined organic layers were washed with 1N-NaOH and saturated sodium hydrogen carbonate. After drying with anhydrous sodium sulfate and evaporation of the solvent, the crude product was purified by silica gel chromatography (Biotage) using Acetone:Hexane as an eluent to yield 0.202 g (75% yield) of the title compound 13. Detected mass m/z 197 (M+H$^+$).

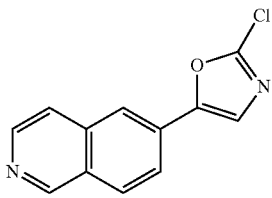 [SMILES: Clc1ncc(-c2ccc3cnccc3c2)o1]

Compound 14: 2-chloro-5-(isoquinolin-6-yl)oxazole

LiHMDS (1.06 M in THF, 1.16 mL, 1.23 mmol) was added to a solution of 5-(isoquinolin-6-yl)oxazole 13 (0.202 g, 1.03 mmol) in THF (20 mL) at −78° C., and the mixture was stirred at −78° C. for 1 h. A solution of hexachloroethane (0.365 g, 1.545 mmol) in THF (5 mL) was added at −78° C., and the mixture was stirred at −78° C. for 2 h and allowed to warm to room temperature and stirred for 14 h. The reaction was quenched by adding EtOAC:$H_2O$ (50 mL:15 mL), and then extracted with Ethyl acetate. The extracts were washed with brine, dried ($Na_2SO_4$) and concentrated. The product was purified by column chromatography (Acetone/hexane as an eluent) to provide title compound 14 (0.074 g, 32% yield) as white solid. MS (ES) m/z 231 (M+H$^+$).

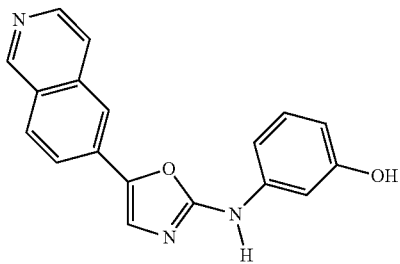 [SMILES: Oc1cccc(Nc2ncc(-c3ccc4cnccc4c3)o2)c1]

Compound 15: 3-((5-(isoquinolin-6-yl)oxazol-2-yl) amino)phenol

A mixture of 2-chloro-5-(isoquinolin-6-yl)oxazole 14 (0.074 g, 0.321 mmol) and commercially available 3-aminophenol 8 (0.038 g, 0.348 mmol) in 2-propanol (20 mL) was heated to 80° C. for 18 h with stirring. Upon cooling, solvent was evaporated and silica column purified (Biotage) (Acetone/hexane as an eluent) to provide title compound 15 (0.038 g, 39% yield) as pale yellow solid. MS (ES) m/z 304 (M+H$^+$).

(NOTE: In this case, the entire product is isolated as free base due to phenolic functionality. No hydrochloride salt is observed).

Example 6

Synthesis of 3-((5-(1H-indol-2-yl)oxazol-2-yl) amino)phenol

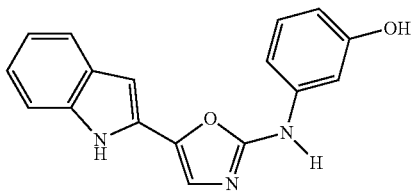 [SMILES: Oc1cccc(Nc2ncc(-c3cc4ccccc4[nH]3)o2)c1]

3-((5-(1H-indol-2-yl)oxazol-2-yl)amino)phenol

CH1189

Figure 11:
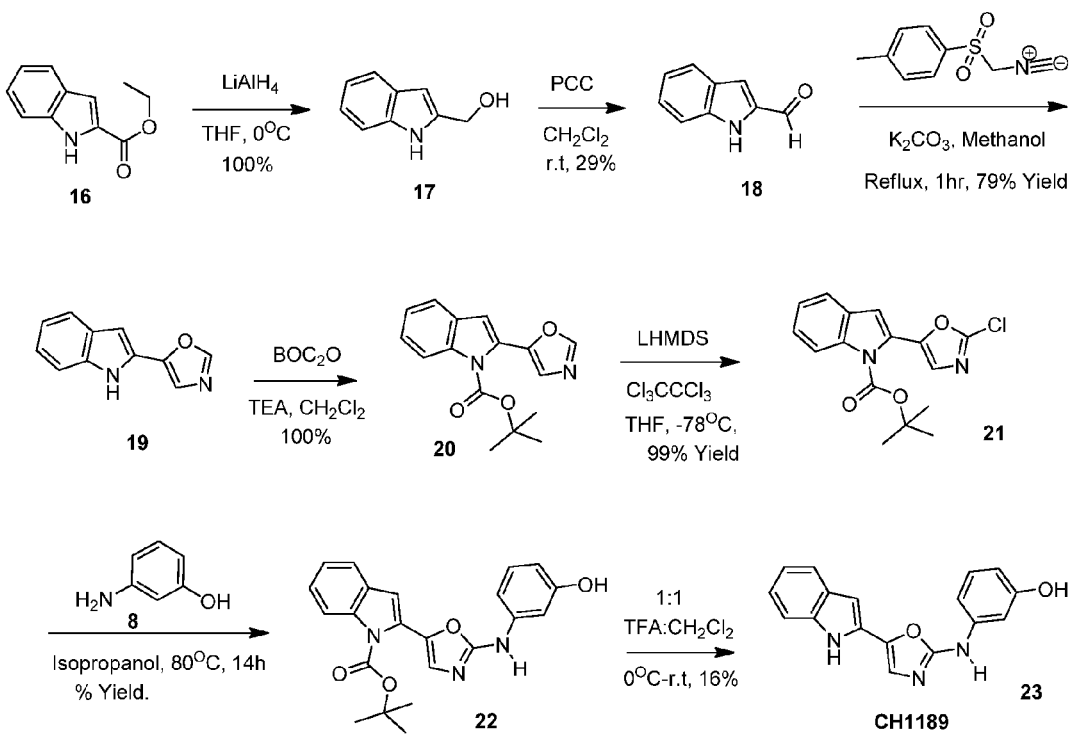
FIG. 11 depicts an exemplary synthetic route for the preparation of a compound of the invention.
Figure 12:
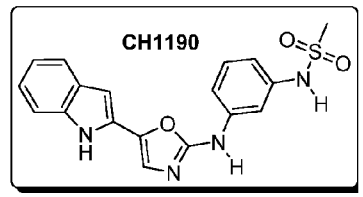
FIG. 12 depicts assay results for a compound of the invention.

The general synthetic scheme for CH1189 (compound 23) is found in FIG. 11.

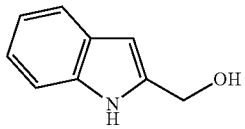 [SMILES: OCc1cc2ccccc2[nH]1]

Compound 17: (1H-indol-2-yl)methanol

To ethyl 1H-indole-2-carboxylate 16 (6.5 g, 34.35 mmol) in THF at 0° C. was added lithium aluminum hydride solution (1M, in THF 1.43 g, 37.78 mmol) dropwise and the reaction mixture was stirred for 3.5 hours at 0° C. The reaction mixture was quenched with $H_2O$, 15% NaOH, and $H_2O$ before it was filtered and rinsed with THF. Reaction mixture was dried (anhydrous $Na_2SO_4$) and evaporation of the solvent gave 5.37 g (100% yield) of the crude (1H-indol-2-yl)methanol 17 which was used directly in the next step.

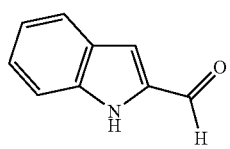 [SMILES: O=Cc1cc2ccccc2[nH]1]

Compound 18: 1H-indole-2-carbaldehyde

To a stirred solution of crude (1H-indol-2-yl)methanol 17 (5.37 g, 36.53 mmol) in anhydrous $CH_2Cl_2$ (50 mL) at cold-bath temperature (~10° C.) was added portionwise pyridinium chlorochromate (PCC) (9.44 g, 40.18 mmol). Reaction was stirred at ambient temperature for 2 hours. Reaction was diluted with $CH_2Cl_2$ and filtered through a pad of celite and washed with $CH_2Cl_2$. After evaporation of solvent, crude product was silica-column chromatographed (Biotage) using Acetone:Hexane as an eluent to yield 1H-indole-2-carbaldehyde 18 (1.52 g, 29% yield).

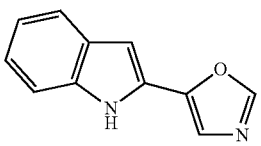 [SMILES: c1ccc2[nH]c(-c3cnco3)cc2c1]

Compound 19: 5-(1H-indol-2-yl)oxazole

To a 100 mL round-bottom flask was added 1H-indole-2-carbaldehyde 18 (1.52 g, 10.48 mmol), methanol (50 mL), p-toluene sulfonylmethyl isocyanide (2.25 g, 11.52 mmol), followed by potassium carbonate (1.86 g, 13.45 mmol). The reaction mixture was stirred at reflux for about 1.5 hour and followed by TLC. The solvent was then evaporated and saturated aq.NaHCO$_3$ was added. The resultant suspension was extracted with CH$_2$Cl$_2$ (3×30 mL). Combined organic layers were washed with brine, dried (anhydrous Na$_2$SO$_4$), and concentrated to leave a yellow solid. Crude product was further purified by silica-column chromatographed (Biotage) using Acetone:Hexane as an eluent to yield 5-(1H-indol-2-yl)oxazole 19 (1.54 g, 79% yield). MS (ES) m/z 185 (M+H$^+$).

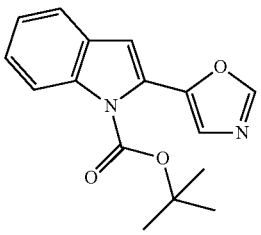 [SMILES: CC(C)(C)OC(=O)n1c(-c2cnco2)cc2ccccc21]

Compound 20: tert-butyl 2-(oxazol-5-yl)-1H-indole-1-carboxylate

To a stirred solution of 5-(1H-indol-2-yl)oxazole 19 (1.54 g, 8.36 mmol) in anhydrous CH$_2$Cl$_2$ (25 mL) at room temperature were added di tert-butyldicarbonate (BOC$_2$O) (2.55 g, 11.68 mmol), 4-Dimethylamino Pyridine (DMAP) (0.2 g, 1.63 mmol) and Triethylamine (2.2 mL, 16.13 mmol). Reaction was stirred for 6 hours at ambient temperature. It was concentrated and crude product was purified by silica-column chromatographed (Biotage) using Acetone:Hexane as an eluent to yield tert-butyl 2-(oxazol-5-yl)-1H-indole-1-carboxylate 20 (2.37 g, 100% yield). MS (ES) m/z 285 (M+H$^+$).

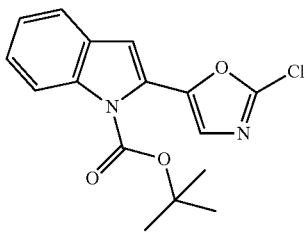 [SMILES: CC(C)(C)OC(=O)n1c(-c2cnc(Cl)o2)cc2ccccc21]

Compound 21: tert-butyl 2-(2-chlorooxazol-5-yl)-1H-indole-1-carboxylate

LiHMDS (1.06 M in THF, 9.54 mL, 10.00 mmol) was added to a solution of tert-butyl 2-(oxazol-5-yl)-1H-indole-1-carboxylate 20 (2.37 g, 8.34 mmol) in THF (20 mL) at −78° C., and the mixture was stirred at −78° C. for 1 h. A solution of hexachloroethane (2.96 g, 12.50 mmol) in THF (5 mL) was added at −78° C., and the mixture was stirred at −78° C. for 2 h and allowed to warm to room temperature and stirred for 14 h. The reaction was quenched by adding EtOAC:H$_2$O (50 mL:15 mL), and then extracted with Ethyl acetate. The extracts were washed with brine, dried (Na$_2$SO$_4$) and concentrated. The product was purified by column chromatography (Acetone/hexane as an eluent) to provide tert-butyl 2-(2-chlorooxazol-5-yl)-1H-indole-1-carboxylate 21 (2.64 g, 99% yield) as white solid. MS (ES) m/z 319 (M+H$^+$).

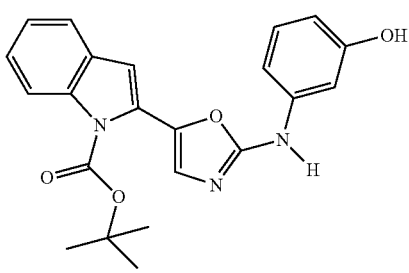 [SMILES: CC(C)(C)OC(=O)n1c(-c2cnc(Nc3cccc(O)c3)o2)cc2ccccc21]

Compound 22: tert-butyl 2-(2-((3-hydroxyphenyl)amino)oxazol-5-yl)-1H-indole-1-carboxylate A mixture of tert-butyl 2-(2-chlorooxazol-5-yl)-1H-indole-1-carboxylate 21 (0.23 g, 0.723 mmol) and commercially available 3-aminophenol 8 (0.079 g, 0.724 mmol) in 2-propanol (20 mL) was heated to 80° C. for 14 h with stirring. Upon cooling, solvent was evaporated and silica column purified (Biotage) (Acetone/hexane as an eluent) to provide tert-butyl 2-(2-((3-hydroxyphenyl)amino)oxazol-5-yl)-1H-indole-1-carboxylate 22 (0.209 g, 74% yield) as solid. MS (ES) m/z 392 (M+H$^+$). (NOTE: In this case, the entire product is isolated as free base due to phenolic functionality. No hydrochloride salt is observed).

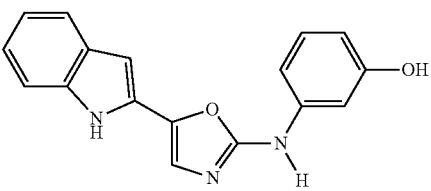 [SMILES: Oc1cccc(Nc2ncc(-c3cc4ccccc4[nH]3)o2)c1]

Compound 23: 3-((5-(1H-indol-2-yl)oxazol-2-yl)amino)phenol

To a stirred solution of tert-butyl 2-(2-((3-hydroxyphenyl)amino)oxazol-5-yl)-1H-indole-1-carboxylate 22 (0.125 g, 0.319 mmol) in anhydrous CH$_2$Cl$_2$ (20 mL) was added 1:1 mixture of CH$_2$Cl$_2$:Trifluoroacetic acid (5 mL) at 0° C. Reaction was stirred for 1 hour at ambient temperature. It was quenched with aq. saturated NaHCO$_3$ and CH$_2$Cl$_2$ layer was separated. After evaporation of solvent, crude product was purified using preparative-TLC to obtain 3-((5-(1H-indol-2-yl)oxazol-2-yl)amino)phenol 23 (0.027 g, 16% yield).

Example 7

Synthesis of N-(3-((5-(1H-indol-2-yl)oxazol-2-yl)amino)phenyl)methanesulfonamide

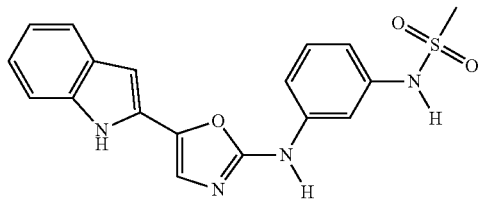 [SMILES: CS(=O)(=O)Nc1cccc(Nc2ncc(-c3cc4ccccc4[nH]3)o2)c1]

N-(3-((5-(1H-indol-2-yl)oxazol-2-yl)amino)phenyl)methanesulfonamide

CH1190

Figure 13:
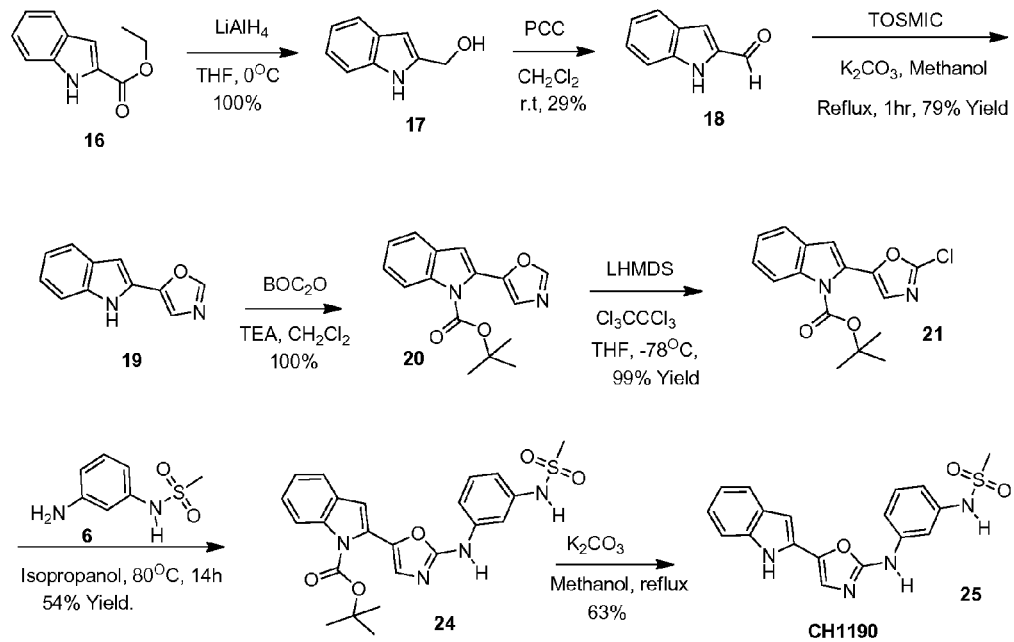
FIG. 13 depicts an exemplary synthetic route for the preparation of a compound of the invention.
Figure 14:
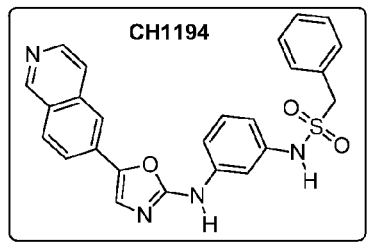
FIG. 14 depicts assay results for a compound of the invention.

The general synthetic scheme for CH1190 (compound 25) is found in FIG. 13. Compound 17, compound 18, compound 19, compound 20, and compound 21 were prepared as described above.

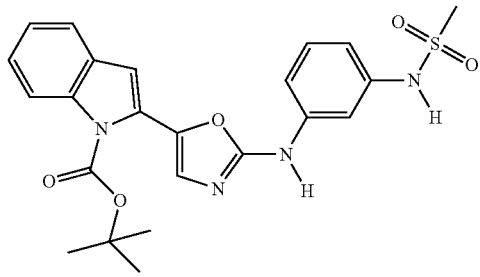 [SMILES: CC(C)(C)OC(=O)n1c(-c2cnc(Nc3cccc(NS(C)(=O)=O)c3)o2)cc2ccccc21]

Compound 24: tert-butyl 2-(2-((3-(methylsulfonamido)phenyl)amino)oxazol-5-yl)-1H-indole-1-carboxylate A mixture of tert-butyl 2-(2-chlorooxazol-5-yl)-1H-indole-1-carboxylate 21 (0.281 g, 0.883 mmol) and commercially available N-(3-aminophenyl)methanesulfonamide 6 (0.321 g, 1.723 mmol) in 2-propanol (20 mL) was heated to 80° C. for 14 h with stirring. Upon cooling, solvent was evaporated and silica column purified (Biotage) (Acetone/hexane as an eluent) to provide tert-butyl 2-(2-((3-(methylsulfonamido) phenyl)amino)oxazol-5-yl)-1H-indole-1-carboxylate 24 (0.221 g, 54% yield) as solid. MS (ES) m/z 469 (M+H$^+$).

(NOTE: In this case, the entire product is isolated as free base due to sulfonamide functionality. No hydrochloride salt is observed).

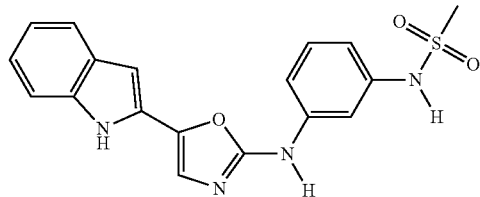 [SMILES: CS(=O)(=O)Nc1cccc(Nc2ncc(-c3cc4ccccc4[nH]3)o2)c1]

Compound 25: N-(3-((5-(1H-indol-2-yl)oxazol-2-yl)amino)phenyl)methanesulfonamide To a stirred solution of tert-butyl 2-(2-((3-(methylsulfonamido) phenyl)amino)oxazol-5-yl)-1H-indole-1-carboxylate 24 (0.221 g, 0.472 mmol) in methanol (30 mL) was added potassium carbonate (0.652 g, 4.71 mmol) at room temperature. Reaction mixture was refluxed for 2 hours. After completion of the reaction (as judged by TLC) it was concentrated using rotavapour and the crude product was purified by MPLC column chromatography (Biotage; Acetone/hexane as an eluent) to provide N-(3-((5-(1H-indol-2-yl)oxazol-2-yl)amino)phenyl)methanesulfonamide 25 (0.11 g, 63% yield) as a solid. MS (ES) m/z 369 (M+H$^+$).

Example 8

Synthesis of N-(3-((5-(isoquinolin-6-yl)oxazol-2-yl)amino)phenyl)-1-phenylmethanesulfonamide

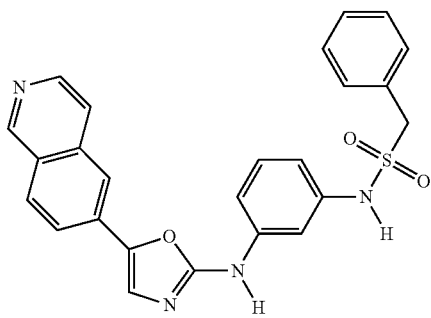 [SMILES: O=S(=O)(Cc1ccccc1)Nc1cccc(Nc2ncc(-c3ccc4cnccc4c3)o2)c1]

N-(3-((5-(isoquinolin-6-yl)oxazol-2-yl)amino)phenyl)-1-phenylmethanesulfonamide
CH1194

N-(3-((5-(isoquinolin-6-yl)oxazol-2-yl)amino)phenyl)-1-phenylmethanesulfonamide

CH1194

Figure 15:
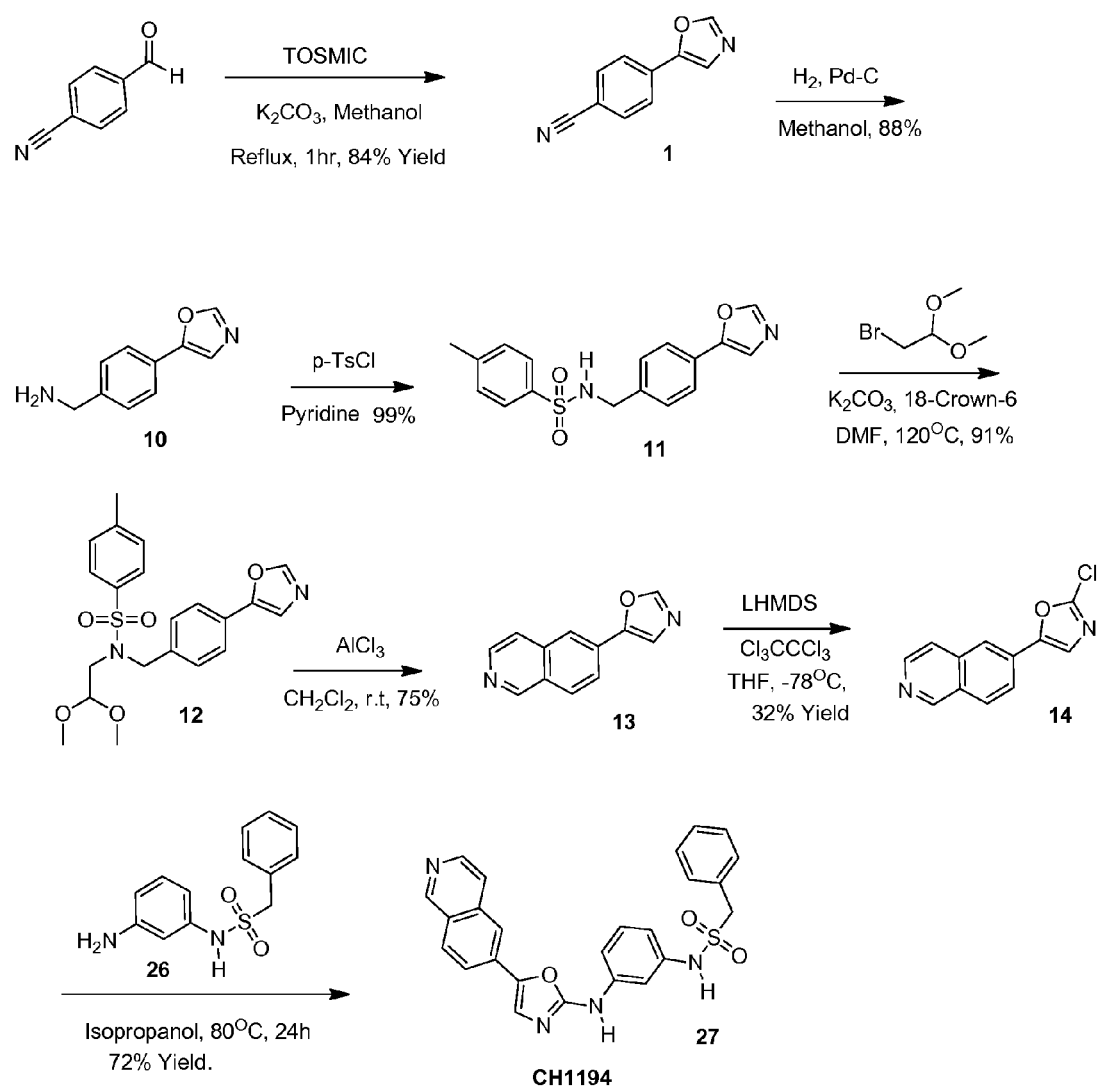
FIG. 15 depicts an exemplary synthetic route for the preparation of a compound of the invention.
Figure 16:
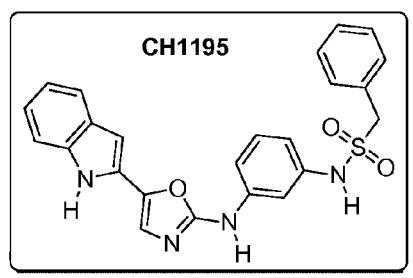
FIG. 16 depicts assay results for a compound of the invention.

The general synthetic scheme for CH1194 (compound 27) is found in FIG. 15. Compound 1, compound 10, compound 11, compound 12, compound 13, and compound 14 were prepared as described above.

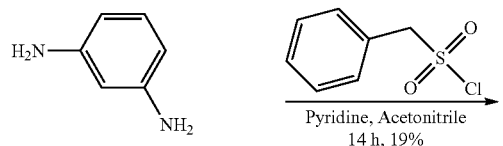

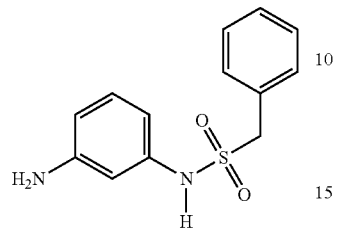

Compound 26:
N-(3-aminophenyl)-1-phenylmethanesulfonamide

To a stirred solution of phenylenediamine (6.93 g, 64.08 mmol) in CH$_3$CN was added pyridine (6.05 g, 76.89 mmol). After stirring at room temperature for 10 minutes it was cooled to ~10° c. and added phenylmethylsulfonyl chloride (6 g, 32.04 mmol). Reaction was further stirred for 14 hours at ambient temperature. Reaction was quenched with aqueous NaHCO$_3$ (saturated) and stirred for 30 minutes. Solid was filtered, and dried under high vacuum to obtain crude N-(3-aminophenyl)-1-phenylmethanesulfonamide 26 (3.1 g, 19% yield). MS (ES) m/z 263 (M+H$^+$).

(NOTE: In this case, the entire product is isolated as free base due to sulfonamide functionality. No hydrochloride salt is observed).

Example 9

Synthesis of N-(3-((5-(1H-indol-2-yl)oxazol-2-yl)amino)phenyl)-1-phenylmethanesulfonamide

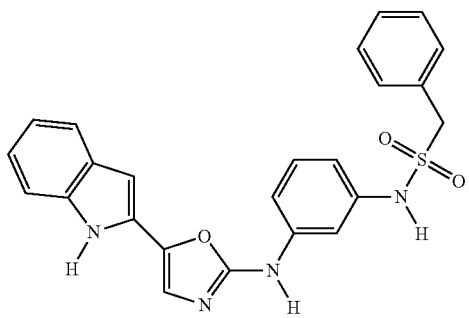

N-(3-((5-(1H-indol-2-yl)oxazol-2-yl)amino)phenyl)-1-phenylmethanesulfonamide
CH1195

N-(3-((5-(1H-indol-2-yl)oxazol-2-yl)amino)phenyl)-1-phenylmethanesulfonamide

CH1195

Figure 17:
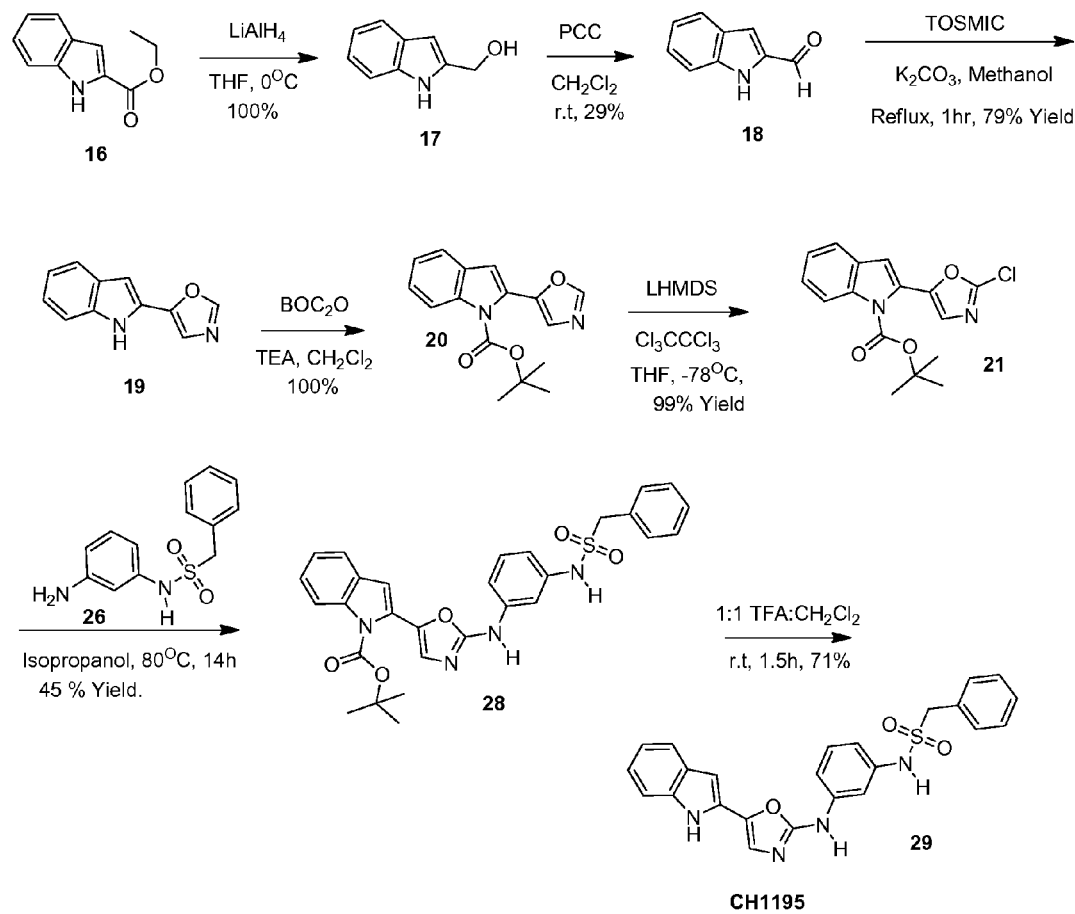
FIG. 17 depicts an exemplary synthetic route for the preparation of a compound of the invention.
Figure 18:
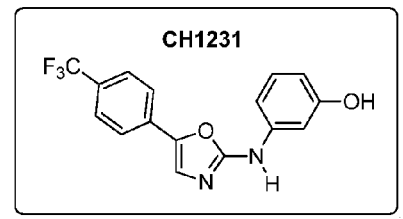
FIG. 18 depicts assay results for a compound of the invention.

The general synthetic scheme for CH1195 (compound 29) is found in FIG. 17. Compound 17, compound 18, compound 19, compound 20, and compound 21 were prepared as described above.

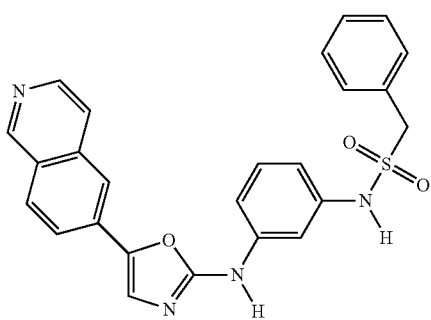

Compound 27: N-(3-((5-(isoquinolin-6-yl)oxazol-2-yl)amino)phenyl)-1-phenylmethanesulfonamide A mixture of 2-chloro-5-(isoquinolin-6-yl)oxazole 14 (0.069 g, 0.30 mmol) and N-(3-aminophenyl)-1-phenylmethanesulfonamide 26 (0.157 g, 0.599 mmol) in 2-propanol (20 mL) was heated to 80° C. for 24 h with stirring. Upon cooling, solvent was evaporated and silica column purified (Biotage) (Acetone/hexane as an eluent) to provide N-(3-((5-(isoquinolin-6-yl)oxazol-2-yl)amino)phenyl)-1-phenylmethanesulfonamide 27 (0.099 g, 72% yield) as pale yellow solid. MS (ES) m/z 457 (M+H$^+$).

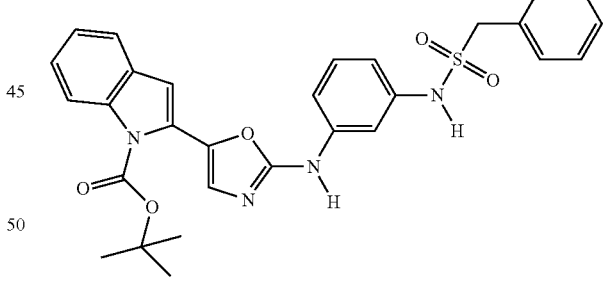

Compound 28: tert-butyl 2-(2-((3-(phenylmethylsulfonamido)phenyl)amino)oxazol-5-yl)-1H-indole-1-carboxylate A mixture of tert-butyl 2-(2-chlorooxazol-5-yl)-1H-indole-1-carboxylate 21 (0.31 g, 0.974 mmol) and N-(3-aminophenyl)-1-phenylmethanesulfonamide 26 (3.1 g, 1.948 mmol) in 2-propanol (20 mL) was heated to 80° C. for 14 h with stirring. Upon cooling, solvent was evaporated and silica column purified (Biotage) (Acetone/hexane as an eluent) to provide tert-butyl 2-(2-((3-(phenylmethylsulfonamido)phenyl)amino)oxazol-5-yl)-1H-indole-1-carboxylate 28 (0.24 g, 45% yield) as solid. MS (ES) m/z 545 (M+H$^+$).

(NOTE: In this case, the entire product is isolated as free base due to phenolic functionality. No hydrochloride salt is observed).

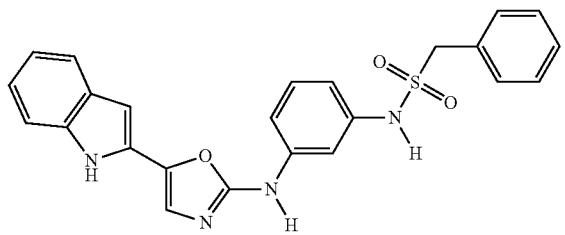 [SMILES: O=S(=O)(Cc1ccccc1)Nc1cccc(Nc2ncc(-c3cc4ccccc4[nH]3)o2)c1]

Compound 29: N-(3-((5-(1H-indol-2-yl)oxazol-2-yl)amino)phenyl)-1-phenylmethanesulfonamide To a stirred solution of tert-butyl 2-(2-((3-(phenylmethylsulfonamido)phenyl)amino)oxazol-5-yl)-1H-indole-1-carboxylate 28 (0.24 g, 0.441 mmol) in anhydrous $CH_2Cl_2$ (20 mL) was added 1:1 mixture of $CH_2Cl_2$:Trifluoroacetic acid (10 mL) at room temperature. Reaction was stirred for 1.5 hour at ambient temperature. It was quenched with aq. saturated $NaHCO_3$ and $CH_2Cl_2$ layer was separated. After evaporation of solvent, crude product was purified using MPLC silica column (Biotage) (Acetone/hexane as an eluent) to obtain N-(3-((5-(1H-indol-2-yl)oxazol-2-yl)amino)phenyl)-1-phenyl methane sulfonamide 29 (0.14 g, 71% yield).

Example 10

Synthesis of 3-((5-(4-(trifluoromethyl)phenyl)oxazol-2-yl)amino)phenol

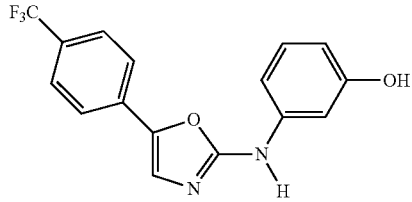 [SMILES: Oc1cccc(Nc2ncc(-c3ccc(C(F)(F)F)cc3)o2)c1]

3-((5-(4-(trifluoromethyl)phenyl)oxazol-2-yl)amino)phenol

CH1231

Figure 19:
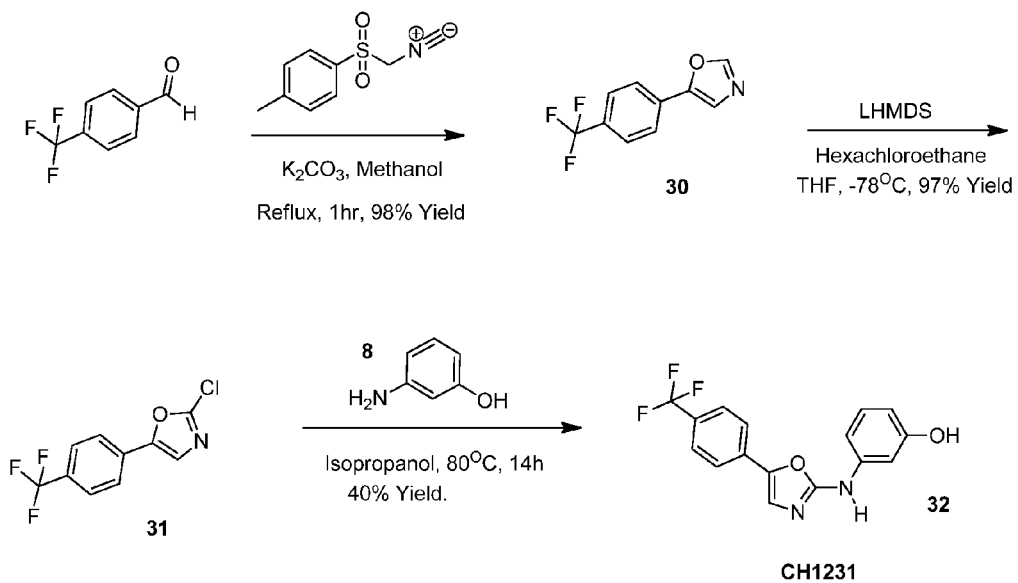
FIG. 19 depicts an exemplary synthetic route for the preparation of a compound of the invention.
Figure 20:
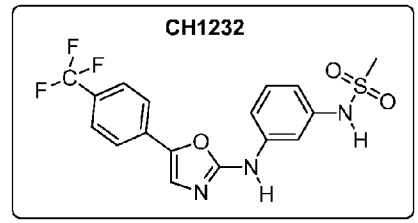
FIG. 20 depicts assay results for a compound of the invention.

The general synthetic scheme for CH1231 (compound 32) is found in FIG. 19.

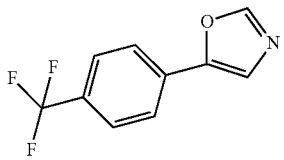 [SMILES: FC(F)(F)c1ccc(-c2cnco2)cc1]

Compound 30: 5-(4-(trifluoromethyl)phenyl)oxazole

To a 250 mL round-bottom flask was added 4-(trifluoromethyl)benzaldehyde (4.50 g, 25.84 mmol), methanol (100 mL), p-toluene sulfonylmethyl isocyanide (5.55 g, 28.42 mmol), followed by potassium carbonate (4.60 g, 33.33 mmol). The reaction mixture was stirred at reflux for about 1 hour and followed by TLC. The solvent was then evaporated and saturated aq.$NaHCO_3$ was added. The resultant suspension was extracted with $CH_2Cl_2$ (3×20 mL). Combined organic layers were washed with brine, dried (anhydrous $Na_2SO_4$), and concentrated to leave a yellow solid. The product was purified by MPLC column chromatography (Biotage; Acetone/hexane as an eluent) to provide 544-(trifluoromethyl)phenyl)oxazole 30 (5.38 g, 98% yield) as white solid. MS (ES) m/z 214 (M+H$^+$).

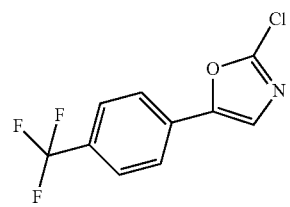 [SMILES: FC(F)(F)c1ccc(-c2cnc(Cl)o2)cc1]

Compound 31: 2-chloro-5-(4-(trifluoromethyl)phenyl)oxazole

LiHMDS (1.06 M in THF, 28.59 mL, 30.3 mmol) was added to a solution of 5-(4-(trifluoromethyl)phenyl)oxazole 30 (5.38 g, 25.25 mmol) in THF (100 mL) at −78° C., and the mixture was stirred at −78° C. for 1 h. A solution of hexachloroethane (8.96 g, 37.87 mmol) in THF (10 mL) was added at −78° C., and the mixture was stirred at −78° C. for 2 h and allowed to warm to room temperature and stirred for 14 h. The reaction was quenched by adding EtOAC:H$_2$O (50 mL:15 mL), and then extracted with Ethyl acetate. The extracts were washed with brine, dried (Na$_2$SO$_4$) and concentrated. The product was purified by column chromatography (Acetone/hexane as an eluent) to provide 2-chloro-5-(4-(trifluoromethyl)phenyl)oxazole 31 (6.05 g, 97% yield) as white solid. MS (ES) m/z 248 (M+H$^+$).

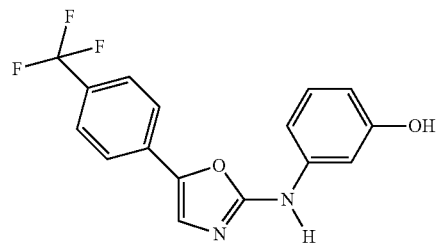 [SMILES: Oc1cccc(Nc2ncc(-c3ccc(C(F)(F)F)cc3)o2)c1]

Compound 32: 3-((5-(4-(trifluoromethyl)phenyl)oxazol-2-yl)amino)phenol

A mixture of 2-chloro-5-(4-(trifluoromethyl)phenyl)oxazole 31 (0.511 g, 2.06 mmol) and commercially available 3-aminophenol 8 (0.225 g, 2.06 mmol) in 2-propanol (20 mL) was heated to 80° C. for 14 h with stirring. Upon cooling, solvent was evaporated and silica column purified (Biotage)

(Acetone/hexane as an eluent) to provide 3-(5-(4-(trifluoromethyl)phenyl)oxazol-2-yl)amino)phenol 32 (0.26 g, 40% yield) as a solid. MS (ES) m/z 321 (M+H⁺).

(NOTE: In this case, the entire product is isolated as free base due to phenolic functionality. No hydrochloride salt is observed)

Example 11

Synthesis of N-(3-((5-(4-(trifluoromethyl)phenyl)oxazol-2-yl)amino)phenyl)methanesulfonamide

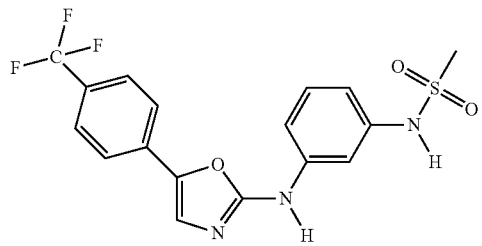 [SMILES: CS(=O)(=O)Nc1cccc(Nc2ncc(-c3ccc(C(F)(F)F)cc3)o2)c1]

N-(3-((5-(4-(trifluoromethyl)phenyl)oxazol-2-yl)amino)phenyl)methanesulfonamide

CH1232

Figure 21:
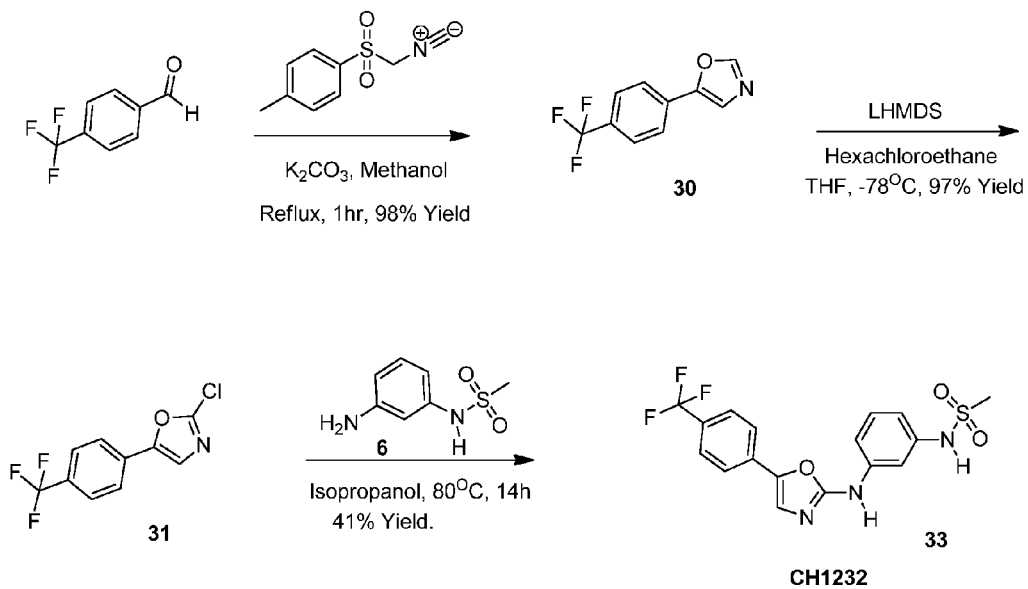
FIG. 21 depicts an exemplary synthetic route for the preparation of a compound of the invention.
Figure 22:
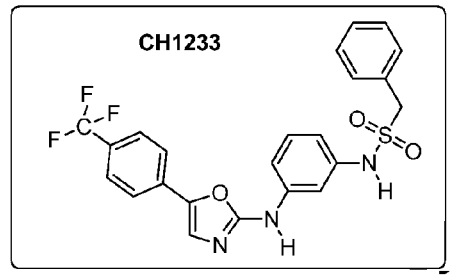
FIG. 22 depicts assay results for a compound of the invention.

The general synthetic scheme for CH1232 (compound 33) is found in FIG. 21. Compound 30 and compound 31 were prepared as described above.

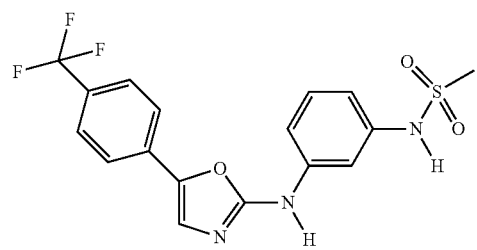 [SMILES: CS(=O)(=O)Nc1cccc(Nc2ncc(-c3ccc(C(F)(F)F)cc3)o2)c1]

Compound 33: N-(3-((5-(4-(trifluoromethyl)phenyl)oxazol-2-yl)amino)phenyl)methanesulfonamide A mixture of 2-chloro-5-(4-(trifluoromethyl)phenyl)oxazole 31 (0.599 g, 2.42 mmol) and commercially available N-(3-aminophenyl)methanesulfonamide 6 (0.451 g, 2.42 mmol) in 2-propanol (20 mL) was heated to 80° C. for 14 h with stirring. Upon cooling, solvent was evaporated and silica column purified (Biotage) (Acetone/hexane as an eluent) to provide N-(3-((5-(4-(trifluoromethyl)phenyl)oxazol-2-yl)amino)phenyl)methane sulfonamide 33 (0.393 g, 41% yield) as a solid. MS (ES) m/z 398 (M+H⁺).

(NOTE: In this case, the entire product is isolated as free base due to phenolic functionality. No hydrochloride salt is observed)

Example 12

Synthesis of 1-phenyl-N-(3-((5-(4-(trifluoromethyl)phenyl)oxazol-2-yl)amino)phenyl)methanesulfonamide

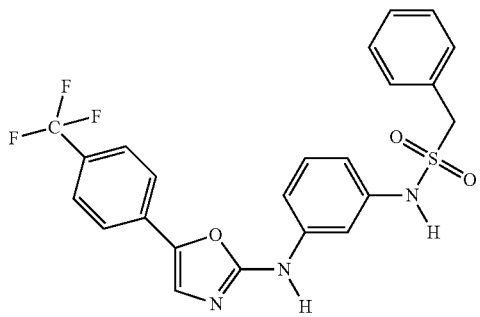 [SMILES: O=S(=O)(Cc1ccccc1)Nc1cccc(Nc2ncc(-c3ccc(C(F)(F)F)cc3)o2)c1]

1-phenyl-N-(3-((5-(4-(trifluoromethyl)phenyl)oxazol-2-yl)amino)phenyl)methanesulfonamide

CH1233

Figure 23:
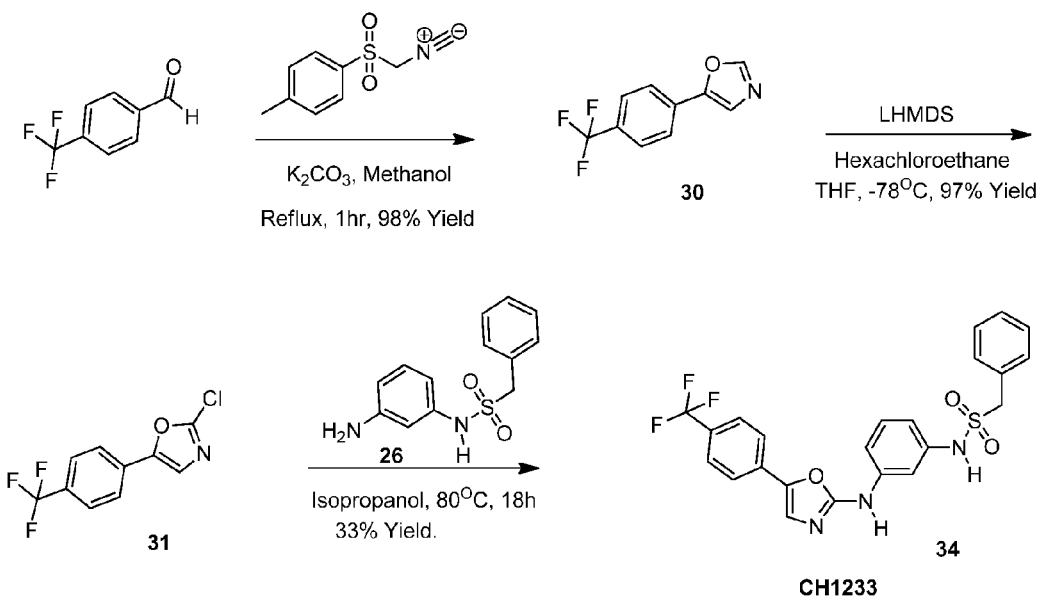
FIG. 23 depicts an exemplary synthetic route for the preparation of a compound of the invention.
Figure 24:
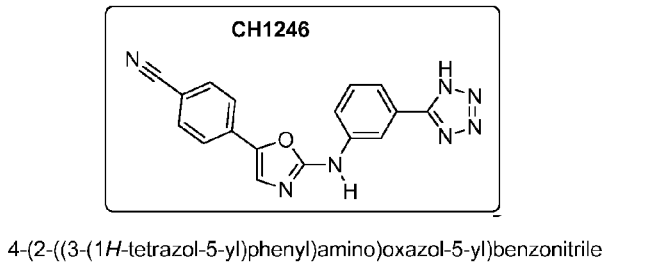
FIG. 24 depicts assay results for a compound of the invention.

The general synthetic scheme for CH1233 (compound 34) is found in FIG. 23. Compound 30 and compound 31 were prepared as described above.

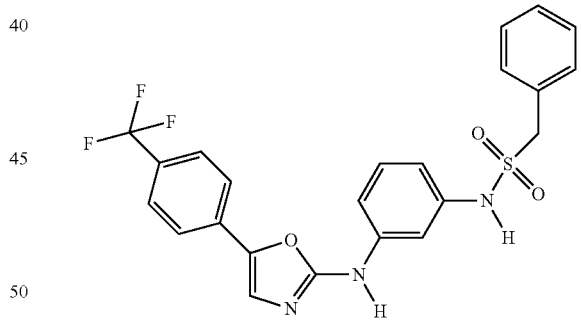

Compound 34: 1-phenyl-N-(3-((5-(4-(trifluoromethyl)phenyl)oxazol-2-yl)amino)phenyl)methane sulfonamide A mixture of 2-chloro-5-(4-(trifluoromethyl)phenyl)oxazole 31 (0.651 g, 2.63 mmol) and N-(3-aminophenyl)-1-phenylmethanesulfonamide 26 (0.69 g, 2.63 mmol) in 2-propanol (50 mL) was heated to 80° C. for 18 h with stirring. Upon cooling, solvent was evaporated and silica column purified (Biotage) (Acetone/hexane as an eluent) to provide 1-phenyl-N-(3-((5-(4-(trifluoromethyl)phenyl)oxazol-2-yl)amino)phenyl)methane sulfonamide. 34 (0.407 g, 33% yield) as a solid. MS (ES) m/z 474 (M+H⁺).

Example 13

Synthesis of 4-(2-((3-(1H-tetrazol-5-yl)phenyl)amino)oxazol-5-yl)benzonitrile

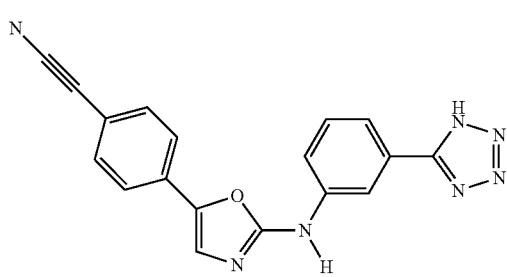 [SMILES: NC#Cc1ccc(-c2cnc(Nc3cccc(-c4nnn[nH]4)c3)o2)cc1]

4-(2-((3-(1H-tetrazol-5-yl)phenyl)amino)oxazol-5-yl)benzonitrile

CH1246

Figure 25:
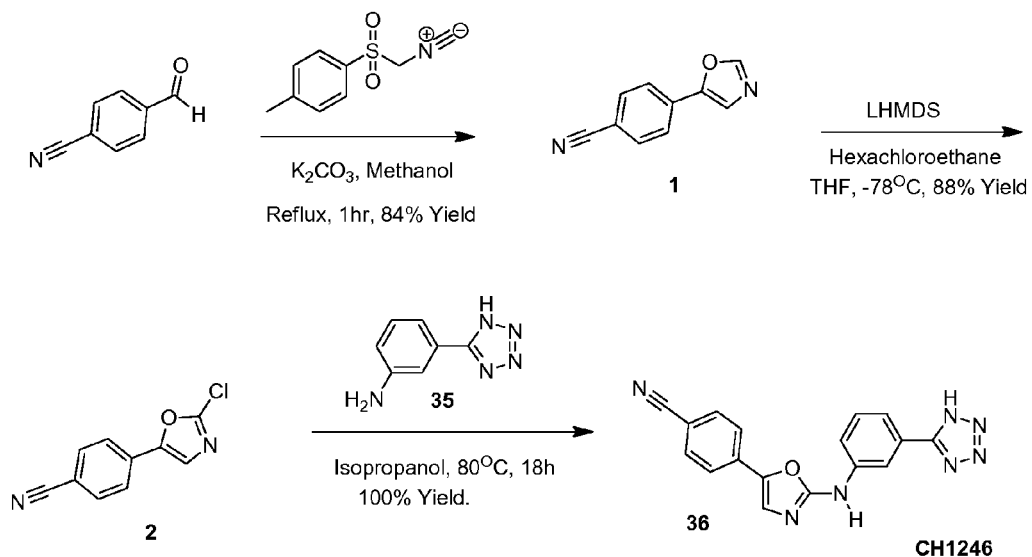
FIG. 25 depicts an exemplary synthetic route for the preparation of a compound of the invention.
Figure 26:
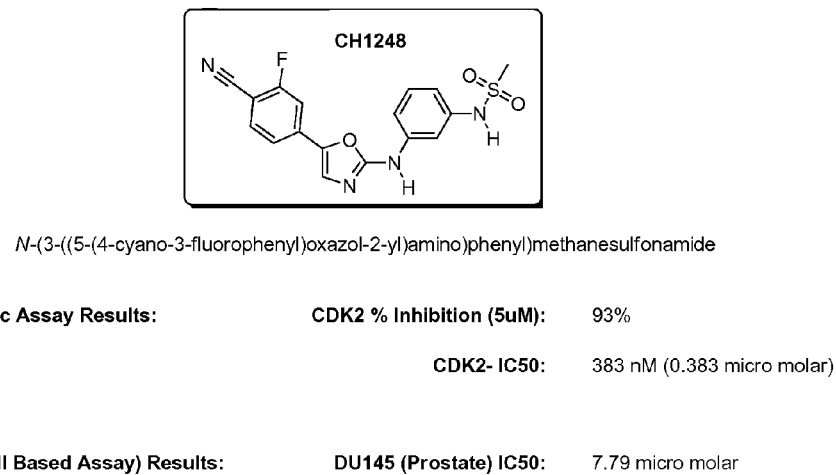
FIG. 26 depicts assay results for a compound of the invention.

The general synthetic scheme for CH1246 (compound 36) is found in FIG. 25. Compound 1 and compound 2 were prepared as described above.

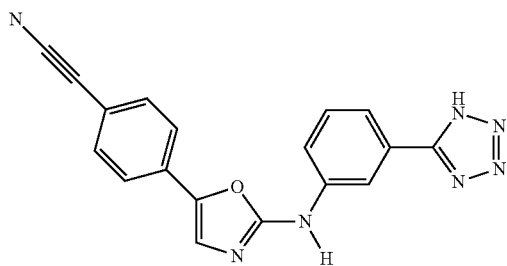 [SMILES: NC#Cc1ccc(-c2cnc(Nc3cccc(-c4nnn[nH]4)c3)o2)cc1]

Compound 36: 4-(2-((3-(1H-tetrazol-5-yl)phenyl)amino)oxazol-5-yl)benzonitrile

A mixture of 4-(2-chlorooxazol-5-yl)benzonitrile 2 (0.216 g, 1.05 mmol) and commercially available 3-(1H-tetrazol-5-yl)aniline 35 (0.17 g, 1.05 mmol) in 2-propanol (20 mL) was heated to 80° C. for 18 h with stirring. Upon cooling, a white solid precipitated out which was filtered off, washed with 2-propanol, and dried. This was further purified by dissolving into DMSO and re-precipitated with addition of water. Resulting solid was filtered, washed with water, methanol and dried under high vacuum to yield 4-(2-((3-(1H-tetrazol-5-yl)phenyl)amino)oxazol-5-yl)benzonitrile 36 as a white solid (0.348 g, 100%). MS (ES) m/z 330 (M+H$^+$).

Example 14

Synthesis of N-(3-((5-(4-cyano-3-fluorophenyl)oxazol-2-yl)amino)phenyl)methanesulfonamide

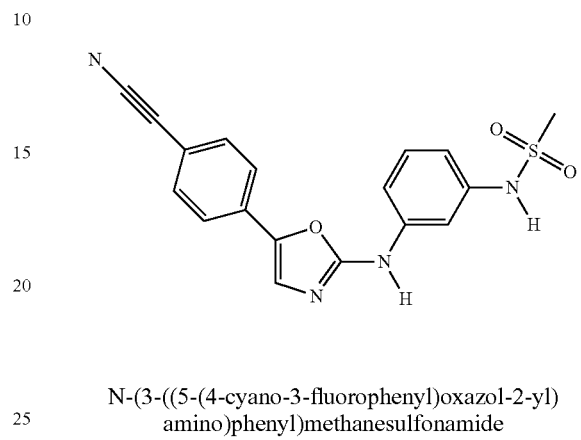

N-(3-((5-(4-cyano-3-fluorophenyl)oxazol-2-yl)amino)phenyl)methanesulfonamide

CH1248

Figure 27:
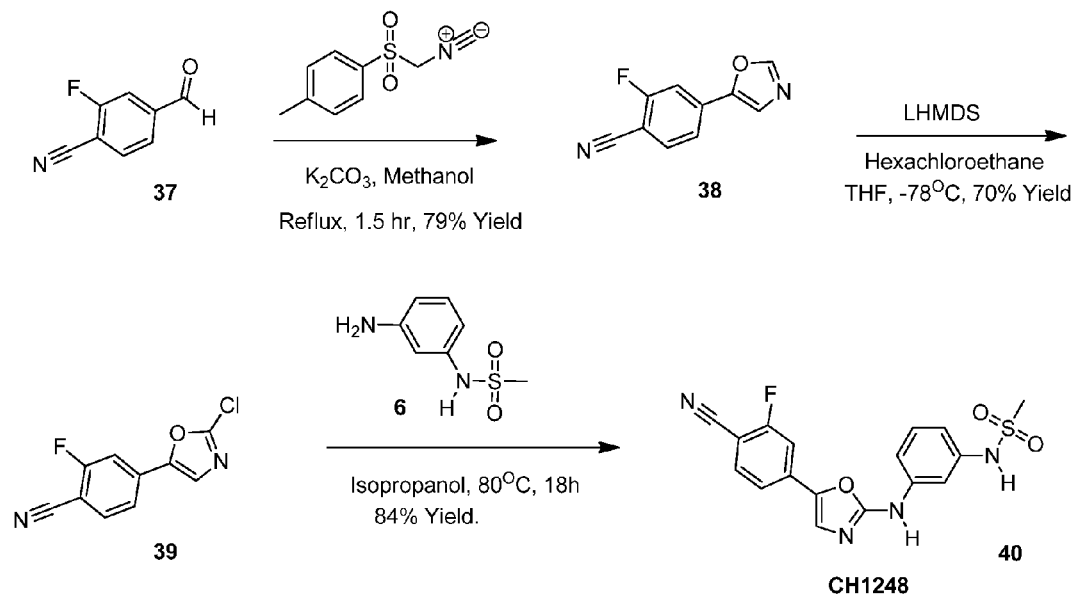
FIG. 27 depicts an exemplary synthetic route for the preparation of a compound of the invention.
Figure 28:
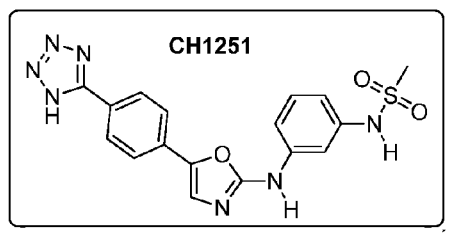
FIG. 28 depicts assay results for a compound of the invention.

The general synthetic scheme for CH1248 (compound 40) is found in FIG. 27.

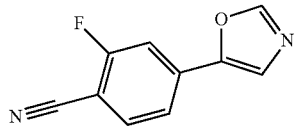 [SMILES: N#Cc1ccc(-c2cnco2)cc1F]

Compound 38: 2-fluoro-4-(oxazol-5-yl)benzonitrile

To a 100 mL round-bottom flask was added 2-fluoro-4-formylbenzonitrile 37 (1.00 g, 6.7 mmol), methanol (25 mL), p-toluene sulfonylmethyl isocyanide (1.44 g, 7.37 mmol), followed by potassium carbonate (1.195 g, 8.64 mmol). The reaction mixture was stirred at reflux for about 1.5 hour and followed by TLC. The solvent was then evaporated and saturated aq.NaHCO$_3$ was added. The resultant suspension was extracted with CH$_2$Cl$_2$ (2×20 mL). Combined organic layers were washed with brine, dried (anhydrous Na$_2$SO$_4$), and concentrated to leave a yellow solid. Crude product was further purified by MPLC (Biotage) silica column chromatography (Acetone/hexane as an eluent) to afford 2-fluoro-4-(oxazol-5-yl)benzonitrile 38 (5.48 g, 79% yield). MS (ES) m/z 189 (M+H$^+$).

Compound 39:
4-(2-chlorooxazol-5-yl)-2-fluorobenzonitrile

LiHMDS (1.06 M in THF, 1.32 mL, 1.40 mmol) was added to a solution of 2-fluoro-4-(oxazol-5-yl)benzonitrile 38 (0.22 g, 1.17 mmol) in THF (20 mL) at −78° C., and the mixture was stirred at −78° C. for 1 h. A solution of hexachloroethane (0.415 g, 1.75 mmol) in THF (5 mL) was added at −78° C., and the mixture was stirred at −78° C. for 2 h and allowed to warm to room temperature and stirred for 14 h. The reaction was quenched by adding EtOAC:H$_2$O (50 mL:15 mL), and then extracted with Ethyl acetate. The extracts were washed with brine, dried (Na$_2$SO$_4$) and concentrated. The product was purified by column chromatography (Acetone/hexane as an eluent) to provide 4-(2-chlorooxazol-5-yl)-2-fluorobenzonitrile 39 (0.18 g, 70% yield) as white solid. MS (ES) m/z 223 (M+H$^+$).

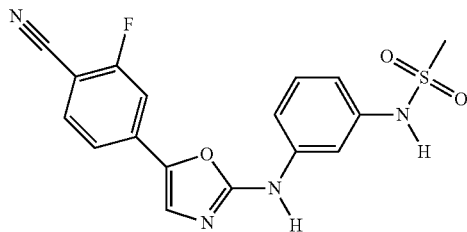 [SMILES: CS(=O)(=O)Nc1cccc(Nc2ncc(-c3ccc(C#N)c(F)c3)o2)c1]

Compound 40: N-(3-((5-(4-cyano-3-fluorophenyl)oxazol-2-yl)amino)phenyl)methanesulfonamide A mixture of 4-(2-chlorooxazol-5-yl)-2-fluorobenzonitrile 39 (0.225 g, 1.01 mmol) and commercially available N-(3-aminophenyl)methanesulfonamide 6 (0.188 g, 1.01 mmol) in 2-propanol (20 mL) was heated to 80° C. for 18 h with stirring. Reaction mixture was evaporated and crude product was purified using MPLC (Biotage) silica column (Biotage) (Acetone/hexane as an eluent) to provide N-(3-((5-(4-cyano-3-fluorophenyl)oxazol-2-yl)amino)phenyl)methane sulfonamide 40 (0.319 g, 84% yield) as a solid. MS (ES) m/z 373 (M+H$^+$).

Example 15

Synthesis of N-(3-((5-(4-(1H-tetrazol-5-yl)phenyl)oxazol-2-yl)amino)phenyl)methanesulfonamide

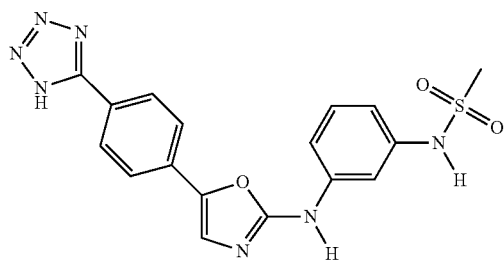 [SMILES: CS(=O)(=O)Nc1cccc(Nc2ncc(-c3ccc(-c4nnn[nH]4)cc3)o2)c1]

N-(3-((5-(4-(1H-tetrazol-5-yl)phenyl)oxazol-2-yl)amino)phenyl)methanesulfonamide

CH1251

Figure 29:
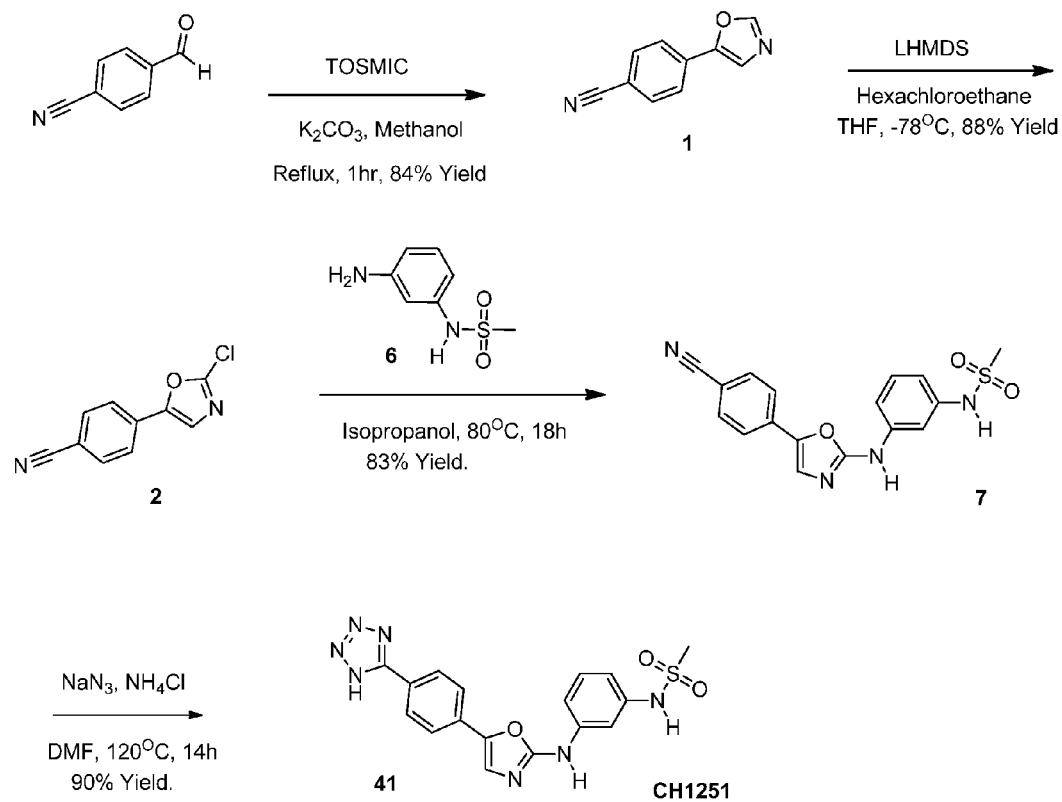
FIG. 29 depicts an exemplary synthetic route for the preparation of a compound of the invention.
Figure 30:
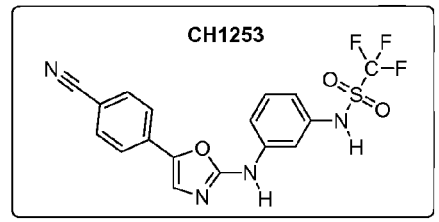
FIG. 30 depicts assay results for a compound of the invention.

The general synthetic scheme for CH1251 (compound 41) is found in FIG. 29. Compound 1, compound 2, and compound 7 were prepared as described above.

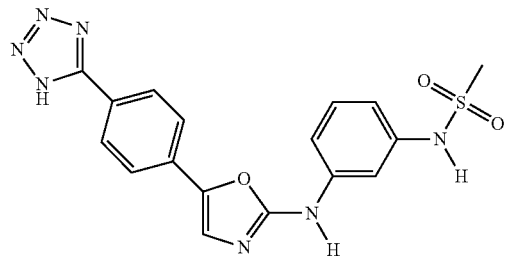 [SMILES: CS(=O)(=O)Nc1cccc(Nc2ncc(-c3ccc(-c4nnn[nH]4)cc3)o2)c1]

Compound 41: N-(3-((5-(4-(1H-tetrazol-5-yl)phenyl)oxazol-2-yl)amino)phenyl)methanesulfonamide N-(3-((5-(4-cyanophenyl)oxazol-2-yl)amino)phenyl)methanesulfonamide 7 (0.12 g, 0.338 mmol) was dissolved in anhydrous DMF (10 mL), Sodium azide (0.088 g, 1.35 mmol) and ammonium chloride (0.072 g, 1.35 mmol) were added to above solution. Resulting suspension was heated at 120° C. for overnight (14 hours). Reaction was cooled down and water was added. Resulting (precipitated) solid was filtered, washed with water, methanol, and water. This was further purified by dissolving into DMSO and re-precipitated with addition of water. Resulting solid was filtered, washed with water, methanol and dried under high vacuum to yield N-(3-((5-(4-(1H-tetrazol-5-yl)phenyl)oxazol-2-yl)amino)phenyl)methanesulfonamide 41 (0.12 g, 90%) as a white solid. MS (ES) m/z 398 (M+H$^+$).

Example 16

Synthesis of N-(3-((5-(4-cyanophenyl)oxazol-2-yl)amino)phenyl)-1,1,1-trifluoromethanesulfonamide

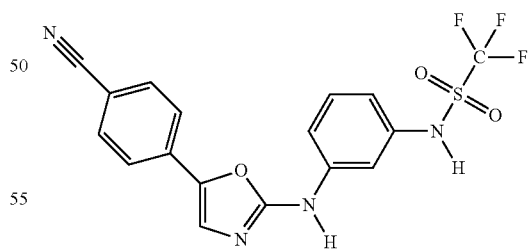

N-(3-((5-(4-cyanophenyl)oxazol-2-yl)amino)phenyl)-1,1,1-trifluoromethanesulfonamide

CH1253

Figure 31:
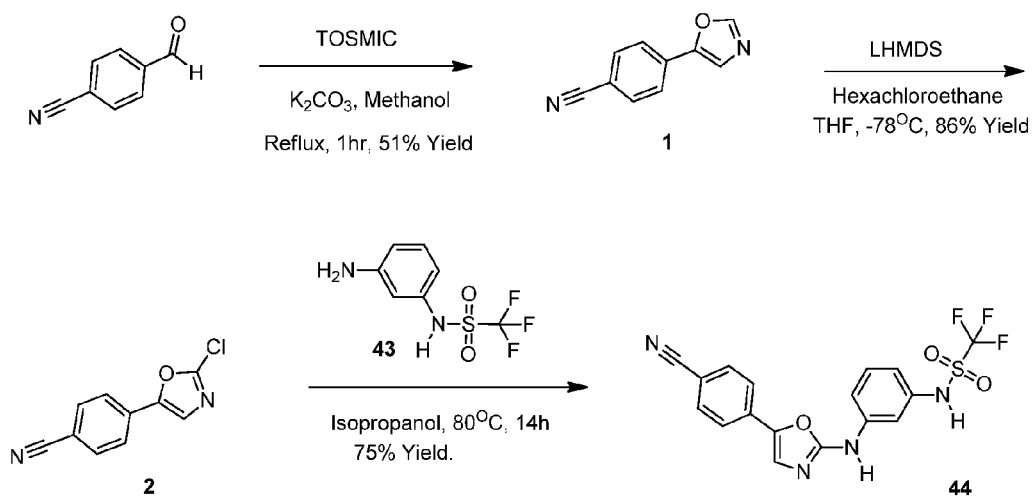
FIG. 31 depicts an exemplary synthetic route for the preparation of a compound of the invention.
Figure 32:
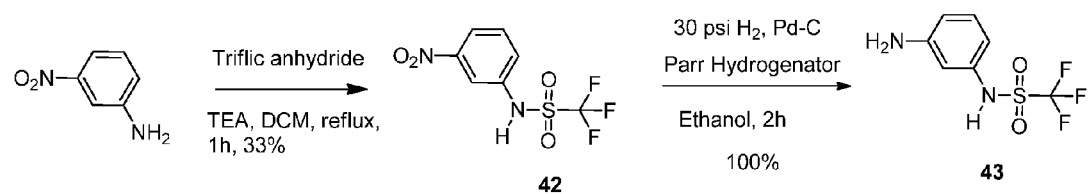
FIG. 32 depicts an exemplary synthetic route for the preparation of an intermediate compound of the invention.
Figure 33:
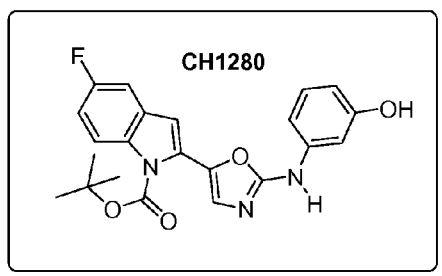
FIG. 33 depicts assay results for a compound of the invention.

The general synthetic scheme for CH1253 (compound 44) is found in FIG. 31. ompound 1 and compound 2 were prepared as described above.

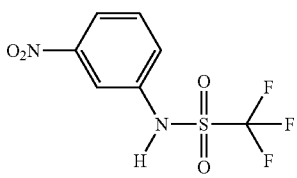

Compound 42: 1,1,1-trifluoro-N-(3-nitrophenyl) methanesulfonamide

Trifluoromethane sulfonic anhydride (6.09 mL, 36.2 mmol) is added to a solution of 3-Nitroaniline (5.00 g, 36.2 mmol) and Triethylamine (5.04 mL, 36.2 mmol) in anhydrous chloroform (50 mL) at 0° C. The cooling bath was removed and the mixture is heated at reflux temperature for 1 hour. After cooling to room temperature, the reaction mixture is poured onto a 10% NaOH solution. The aqueous phase is separated and washed with CHCl$_3$. The basic aq-phase is acidified with conc-HCl and extracted with ethyl acetate (2×65 mL). Combined organic layers are washed with brine, dried (anhydrous Na$_2$SO$_4$) and the solvent is evaporated to obtain 1,1,1-trifluoro-N-(3-nitrophenyl)methane sulfonamide 42 (3.2 g, 33% yield), which was further converted without further purification. MS (ES) m/z 271 (M+H$^+$).

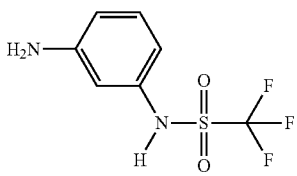 [SMILES: O=[N+]([O-])c1cccc(NS(=O)(=O)C(F)(F)F)c1]

Compound 43: N-(3-aminophenyl)-1,1,1-trifluoromethanesulfonamide 1,1,1-trifluoro-N-(3-nitrophenyl)methanesulfonamide 42 (0.5 g, 1.85 mmol) was dissolved in ethanol (20 mL) treated with H$_2$ (30 psi, Parr hydrogenator) for 2 h in the presence of Pd/C (catalytic, 50 mg). The reaction was monitored by TLC until the starting material was no longer detected. The Pd/C residue was removed by filtration over celite pad, followed by rotary evaporation of the solvent obtained 0.44 g of N-(3-aminophenyl)-1,1,1-trifluoromethanesulfonamide 43 (100% yield). The crude product was further used without further purification. MS (ES) m/z 241 (M+H$^+$).

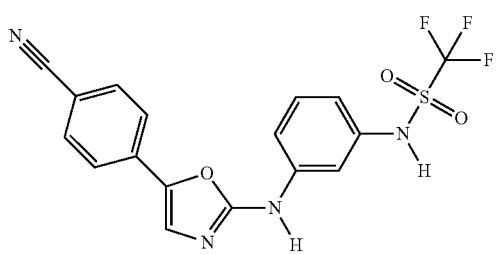 [SMILES: N#Cc1ccc(-c2cnc(Nc3cccc(NS(=O)(=O)C(F)(F)F)c3)o2)cc1]

Compound 44: N-(3-((5-(4-cyanophenyl)oxazol-2-yl)amino)phenyl)-1,1,1-trifluoromethane sulfonamide A mixture of 4-(2-chlorooxazol-5-yl)benzonitrile 2 (0.30 g, 1.47 mmol) and N-(3-aminophenyl)-1,1,1-trifluoromethanesulfonamide 43 (0.35 g, 1.45 mmol) in 2-propanol (25 mL) was heated to 80° C. for 14 h with stirring. Upon cooling, solvent was evaporated and silica column purified (Biotage) (Acetone/hexane as an eluent) to provide N-(3-((5-(4-cyanophenyl)oxazol-2-yl)amino)phenyl)-1,1,1-trifluoromethane sulfonamide 44 (0.45 g, 75% yield) as a solid. MS (ES) m/z 409 (M+H$^+$).

(NOTE: In this case, the entire product is isolated as free base due to sulfonamide functionality. No hydrochloride salt is observed)

Example 17

Synthesis of tert-butyl 5-fluoro-2-(2-((3-hydroxyphenyl)amino)oxazol-5-yl)-1H-indole-1-carboxylate

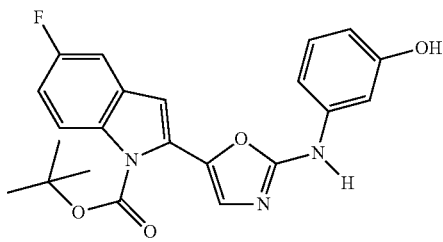 [SMILES: CC(C)(C)OC(=O)n1c(-c2cnc(Nc3cccc(O)c3)o2)cc2cc(F)ccc21]

tert-butyl 5-fluoro-2-(2-((3-hydroxyphenyl)amino) oxazol-5-yl)-1H-indole-1-carboxylate

CH1280

Figure 34:
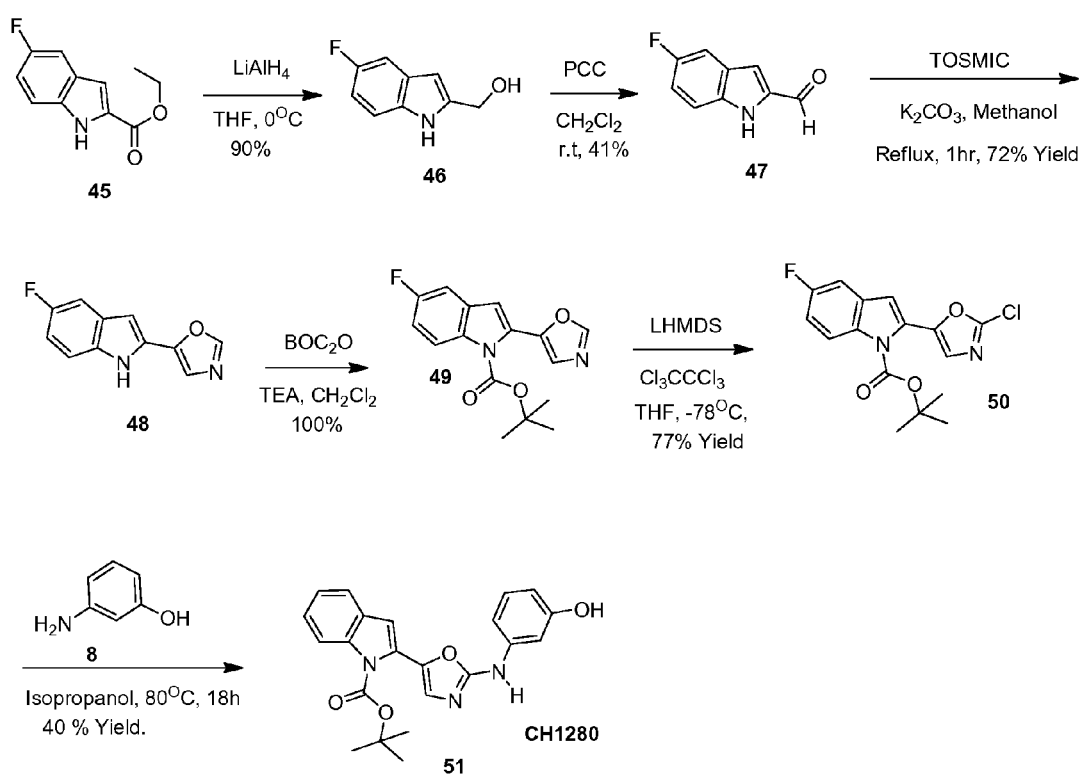
FIG. 34 depicts an exemplary synthetic route for the preparation of a compound of the invention.
Figure 35:
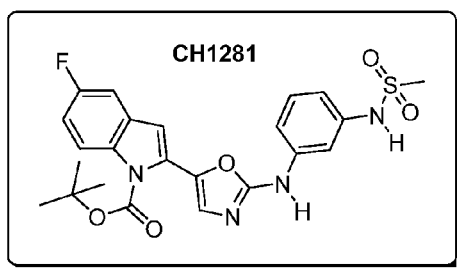
FIG. 35 depicts assay results for a compound of the invention.

The general synthetic scheme for CH1280 (compound 51) is found in FIG. 34.

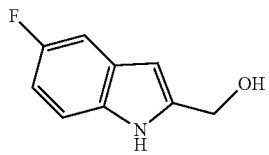 [SMILES: OCc1cc2cc(F)ccc2[nH]1]

Compound 46: (5-fluoro-1H-indol-2-yl)methanol

To ethyl 5-fluoro-1H-indole-2-carboxylate 45 (3.1 g, 14.96 mmol) in THF at 0° C. was added lithium aluminum hydride solution (1 M, in THF 0.625 g, 16.44 mmol) dropwise and the reaction mixture was stirred for 3.5 hours at 0° C. The reaction mixture was quenched with H$_2$O, 15% NaOH, and H$_2$O before it was filtered and rinsed with THF. Reaction mixture was dried (anhydrous Na$_2$SO$_4$) and evaporation of the solvent gave 2.21 g (90% yield) of the crude (5-fluoro-1H-indol-2-yl)methanol 46 which was used directly in the next step.

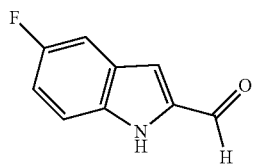 [SMILES: O=Cc1cc2cc(F)ccc2[nH]1]

Compound 47: 5-fluoro-1H-indole-2-carbaldehyde

To a stirred solution of crude (5-fluoro-1H-indol-2-yl) methanol 46 (1.55 g, 9.39 mmol) in anhydrous $CH_2Cl_2$ (50 mL) at cold-bath temperature (0° C.) was added portionwise pyridinium chlorochromate (PCC) (2.22 g, 10.29 mmol). Reaction was stirred at ambient temperature for 4 hours. Reaction was diluted with $CH_2Cl_2$ and filtered through a pad of celite and washed with $CH_2Cl_2$. After evaporation of solvent, crude product was silica-column chromatographed (Biotage) using Acetone:Hexane as an eluent to yield 5-fluoro-1H-indole-2-carbaldehyde 47 (0.627 g, 41% yield).

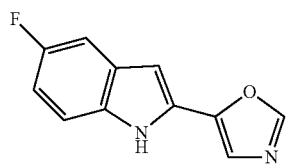 [SMILES: Fc1ccc2[nH]c(-c3cnco3)cc2c1]

Compound 48: 5-(5-fluoro-1H-indol-2-yl)oxazole

To a 100 mL round-bottom flask was added 5-fluoro-1H-indole-2-carbaldehyde 47 (0.627 g, 3.84 mmol), methanol (40 mL), p-toluene sulfonylmethyl isocyanide (0.826 g, 4.23 mmol), followed by potassium carbonate (0.68 g, 4.92 mmol). The reaction mixture was stirred at reflux for about 1.5 hour and followed by TLC. The solvent was then evaporated and saturated aq. $NaHCO_3$ was added. The resultant suspension was extracted with $CH_2Cl_2$ (2×20 mL). Combined organic layers were washed with brine, dried (anhydrous $Na_2SO_4$), and concentrated to leave a yellow solid. Crude product was further purified by silica-column chromatographed (Biotage) using Acetone:Hexane as an eluent to yield 5-(5-fluoro-1H-indol-2-yl)oxazole 48 (0.202 g, 72% yield). MS (ES) m/z 203 (M+H$^+$).

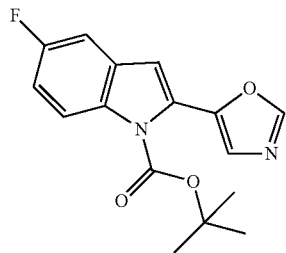 [SMILES: CC(C)(C)OC(=O)n1c(-c2cnco2)cc2cc(F)ccc21]

Compound 49: tert-butyl 5-fluoro-2-(oxazol-5-yl)-1H-indole-1-carboxylate

To a stirred solution of 5-(5-fluoro-1H-indol-2-yl)oxazole 48 (0.55 g, 2.72 mmol) in anhydrous $CH_2Cl_2$ (25 mL) at room temperature were added di tert-butyldicarbonate ($BOC_2O$) (0.83 g, 3.8 mmol), 4-Dimethylamino Pyridine (0.066 g, 0.54 mmol) and Triethylamine (0.74 mL, 5.44 mmol). Reaction was stirred for 2 hours at ambient temperature. It was concentrated and crude product was purified by silica-column chromatographed (Biotage) using Acetone:Hexane as an eluent to yield tert-butyl 5-fluoro-2-(oxazol-5-yl)-1H-indole-1-carboxylate 49 (0.83 g, 100% yield). MS (ES) m/z 303 (M+H$^+$).

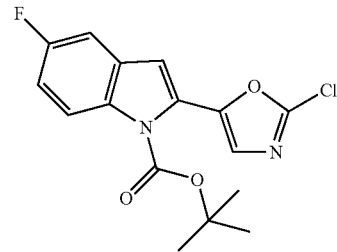 [SMILES: CC(C)(C)OC(=O)n1c(-c2cnc(Cl)o2)cc2cc(F)ccc21]

Compound 50: tert-butyl 2-(2-chlorooxazol-5-yl)-5-fluoro-1H-indole-1-carboxylate LiHMDS (1.06 M in THF, 3.44 mL, 3.43 mmol) was added to a solution of tert-butyl 5-fluoro-2-(oxazol-5-yl)-1H-indole-1-carboxylate 49 (0.865 g, 2.86 mmol) in THF (20 mL) at −78° C., and the mixture was stirred at −78° C. for 1 h. A solution of hexachloroethane (1.01 g, 4.29 mmol) in THF (5 mL) was added at −78° C., and the mixture was stirred at −78° C. for 2 h and allowed to warm to room temperature and stirred for 14 h. The reaction was quenched by adding EtOAC: $H_2O$ (50 mL:15 mL), and then extracted with Ethyl acetate. The extracts were washed with brine, dried ($Na_2SO_4$) and concentrated. The product was purified by column chromatography (Acetone/hexane as an eluent) to provide tert-butyl 2-(2-chlorooxazol-5-yl)-5-fluoro-1H-indole-1-carboxylate 50 (0.74 g, 77% yield) as white solid. MS (ES) m/z 337 (M+H$^+$).

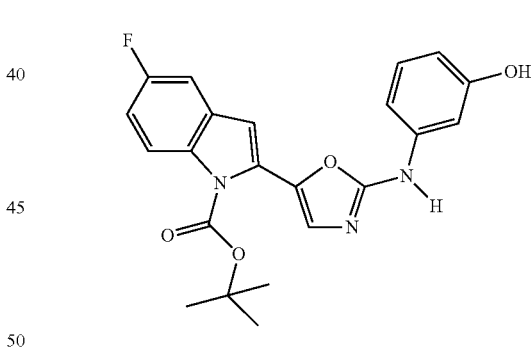

Compound 51: tert-butyl 5-fluoro-2-(2-((3-hydroxyphenyl)amino)oxazol-5-yl)-1H-indole-1-carboxylate A mixture of tert-butyl 2-(2-chlorooxazol-5-yl)-5-fluoro-1H-indole-1-carboxylate 50 (0.308 g, 0.916 mmol) and commercially available 3-aminophenol 8 (0.10 g, 0.916 mmol) in 2-propanol (20 mL) was heated to 80° C. for 18 h with stirring. Upon cooling, solvent was evaporated and silica column purified (Biotage) (Acetone/hexane as an eluent) to provide tert-butyl 5-fluoro-2-(2-((3-hydroxyphenyl)amino)

oxazol-5-yl)-1H-indole-1-carboxylate 51 (0.15 g, 40% yield) as solid. MS (ES) m/z 410 (M+H⁺).

Example 18

Synthesis of tert-butyl 5-fluoro-2-(2-((3-(methylsulfonamido)phenyl)amino)oxazol-5-yl)-1H-indole-1-carboxylate

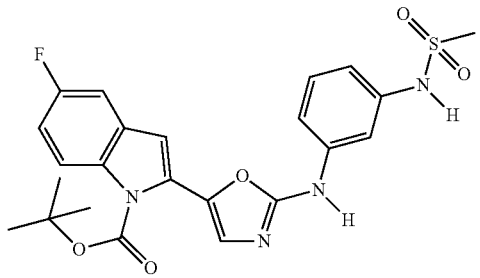 [SMILES: CC(C)(C)OC(=O)n1c(-c2cnc(Nc3cccc(NS(C)(=O)=O)c3)o2)cc2cc(F)ccc21]

tert-butyl 5-fluoro-2-(2-((3-(methylsulfonamido)phenyl)amino)oxazol-5-yl)-1H-indole-1-carboxylate

CH1281

Figure 36:
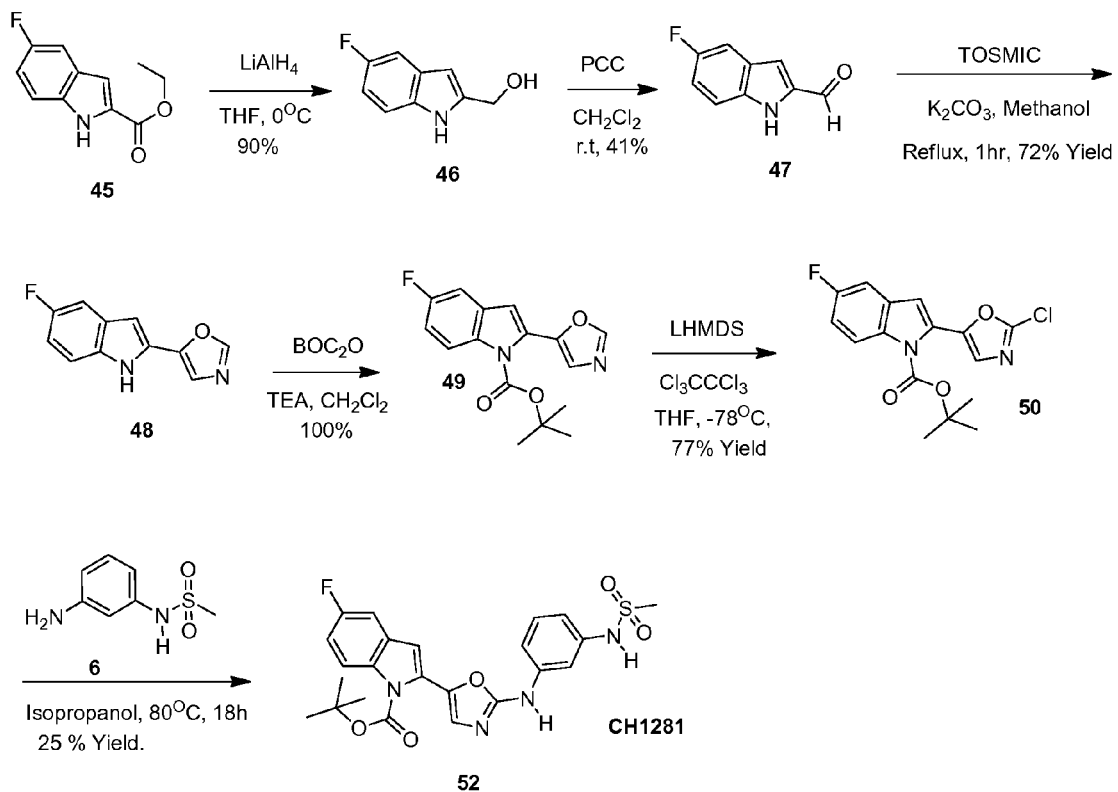
FIG. 36 depicts an exemplary synthetic route for the preparation of a compound of the invention.
Figure 37:
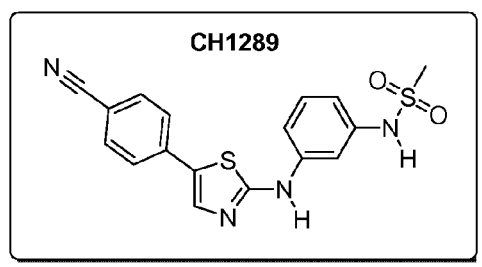
FIG. 37 depicts assay results for a compound of the invention.

The general synthetic scheme for CH1281 (compound 52) is found in FIG. 36. Compound 46, compound 47, compound 48, compound 49, and compound 50 were prepared as described above.

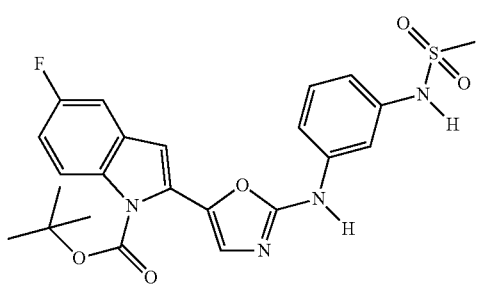 [SMILES: CC(C)(C)OC(=O)n1c(-c2cnc(Nc3cccc(NS(C)(=O)=O)c3)o2)cc2cc(F)ccc21]

Compound 52: tert-butyl 5-fluoro-2-(2-((3-(methylsulfonamido)phenyl)amino)oxazol-5-yl)-1H-indole-1-carboxylate A mixture of tert-butyl 2-(2-chlorooxazol-5-yl)-5-fluoro-1H-indole-1-carboxylate 50 (0.314 g, 0.934 mmol) and commercially available N-(3-aminophenyl)methanesulfonamide 6 (0.174 g, 0.934 mmol) in 2-propanol (20 mL) was heated to 80° C. for 18 h with stirring. Upon cooling, solvent was evaporated and silica column purified (Biotage) (Acetone/hexane as an eluent) to provide tert-butyl 5-fluoro-2-(2-((3-(methylsulfonamido)phenyl)amino)oxazol-5-yl)-1H-indole-1-carboxylate 52 (0.11 g, 25% yield) as solid. MS (ES) m/z 487 (M+H⁺).

Example 19

Synthesis of N-(3-((5-(4-cyanophenyl)thiazol-2-yl)amino)phenyl)methanesulfonamide

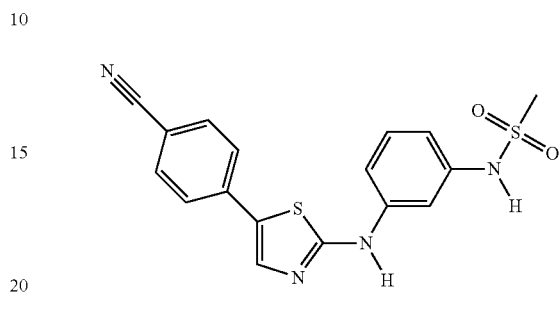

N-(3-((5-(4-cyanophenyl)thiazol-2-yl)amino)phenyl)methanesulfonamide

CH1289

Figure 38:
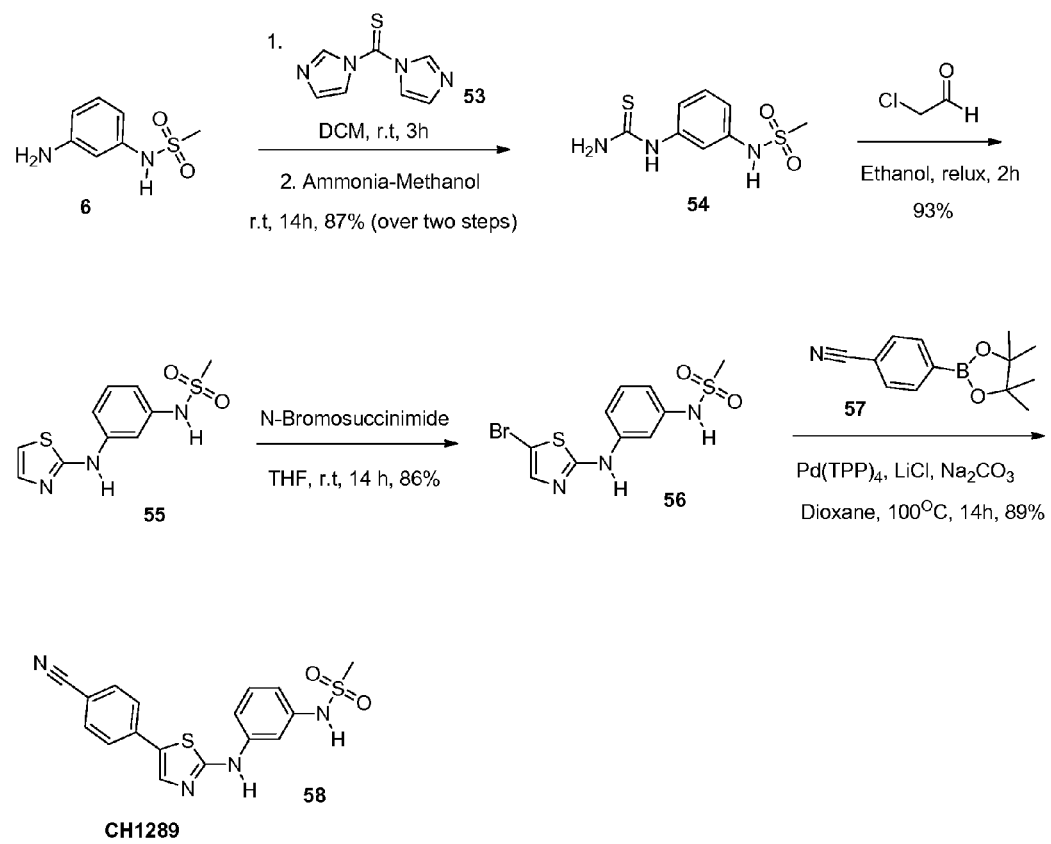
FIG. 38 depicts an exemplary synthetic route for the preparation of a compound of the invention.
Figure 39:
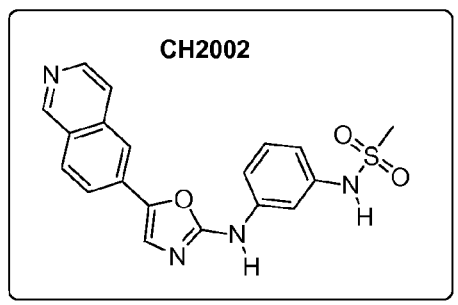
FIG. 39 depicts assay results for a compound of the invention.

The general synthetic scheme for CH1289 (compound 58) is found in FIG. 38.

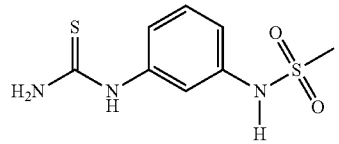

Compound 54: N-(3-thioureidophenyl)methanesulfonamide

To a stirred solution of thiocarbonyl diimidazole 53 (TCDI, 1.80 g, 10.10 mmol) in anhydrous CH₂Cl₂ (25 mL) at 0° C. was added DCM solution of commercially available N-(3-aminophenyl)methanesulfonamide 6 (1.00 g, 5.37 mmol) at 0° C. Reaction was stirred for 3 hours at room temperature. Reaction was again cooled to 0° C. and ammonia-in-methanol (excess, 20 mL) was added dropwise. After stirring for 14 hours at room temperature, it was concentrated and water (20 mL) was added, stirred for 1 hour. Solid product was filtered, washed with water. Solid was dried under vacuum to obtain N-(3-thioureidophenyl)methanesulfonamide 54 (1.14 g, 87% yield). Resulting product was further used without further purification. MS (ES) m/z 246 (M+H⁺).

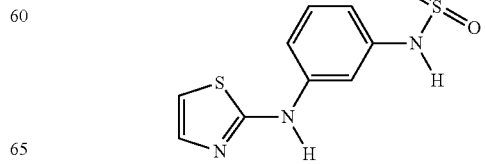

Compound 55: N-(3-(thiazol-2-ylamino)phenyl)methanesulfonamide

N-(3-thioureidophenyl)methanesulfonamide 54 (1.14 g, 4.65 mmol) and 50% aq. chloroacetaldehyde solution (3.65 mL, 23.25 mmol) were taken into ethanol and refluxed for 2 hours. Reaction mixture was concentrated and aq. Saturated NaHCO$_3$ was added. Resulting light brown solid was filtered and washed with water, dried under high vacuum to obtain N-(3-(thiazol-2-ylamino)phenyl)methanesulfonamide 55 (1.17 g, 93% yield). Resulting product was further used without further purification. MS (ES) m/z 270 (M+H$^+$).

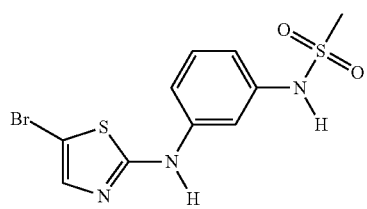 [SMILES: CS(=O)(=O)Nc1cccc(Nc2ncc(Br)s2)c1]

Compound 56: N-(3-((5-bromothiazol-2-yl)amino)phenyl)methanesulfonamide

To a stirred solution of N-(3-(thiazol-2-ylamino)phenyl) methanesulfonamide 55 (1.17 g, 1.85 mmol) in anhydrous THF (25 mL) was added N-bromosuccinimide (0.363 g, 2.03 mmol) at room temperature. Reaction mixture was stirred for 14 hours at ambient temperature. After completion of the reaction (as judged by TLC), it was concentrated and the crude product was MPLC (Biotage) silica column chromatographed using Acetone:Hexane as an eluent to obtain N-(3-((5-bromothiazol-2-yl)amino)phenyl)methanesulfonamide 56 (0.55 g, 86% yield). MS (ES) m/z 348 (M+H$^+$).

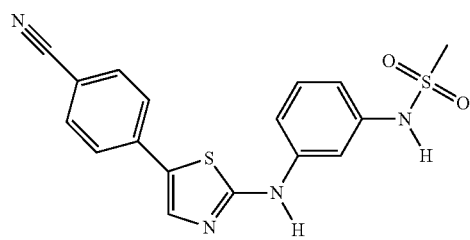

Compound 58: N-(3-((5-(4-cyanophenyl)thiazol-2-yl)amino)phenyl)methanesulfonamide To a mixture of N-(3-((5-bromothiazol-2-yl)amino)phenyl)methanesulfonamide 56 (0.159 g, 0.458 mmol), commercially available 4-(4,4,5,5-tetramethyl-1,3,2-dioxaborolan-2-yl)benzonitrile 57 (0.125 g, 0.545 mmol), Lithium chloride (0.038 g, 0.916 mmol) and tetrakis(triphenylphosphine)palladium (0.058 g, 0.05 mmol) in dry and degassed (using argon) 1,4-Dioxane (20 mL) was added aq. Na$_2$CO$_3$ (1M, 0.91 mL, 0.916 mmol). Reaction mixture was degassed again for 2-3 times for 10 minutes and resulting yellow mixture was stirred under argon at 100° C. for 14 hours. Reaction mixture was filtered through a small pad of celite and concentrated. Crude product was MPLC (Biotage) silica column chromatographed using Acetone:Hexane as an eluent to obtain N-(3-((5-(4-cyanophenyl)thiazol-2-yl)amino)phenyl)methanesulfonamide 58 (0.15 g, 89% yield). MS (ES) m/z 371 (M+H$^+$).

Example 20

Synthesis of N-(3-((5-(isoquinolin-6-yl)oxazol-2-yl)amino)phenyl)methanesulfonamide

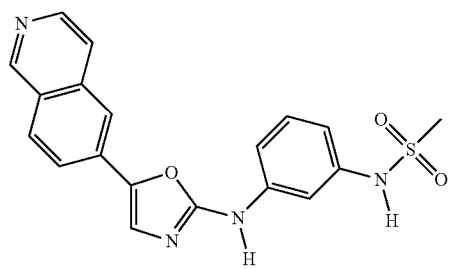 [SMILES: CS(=O)(=O)Nc1cccc(Nc2ncc(-c3ccc4cnccc4c3)o2)c1]

N-(3-((5-(isoquinolin-6-yl)oxazol-2-yl)amino)phenyl)methanesulfonamide

CH2002

Figure 40:
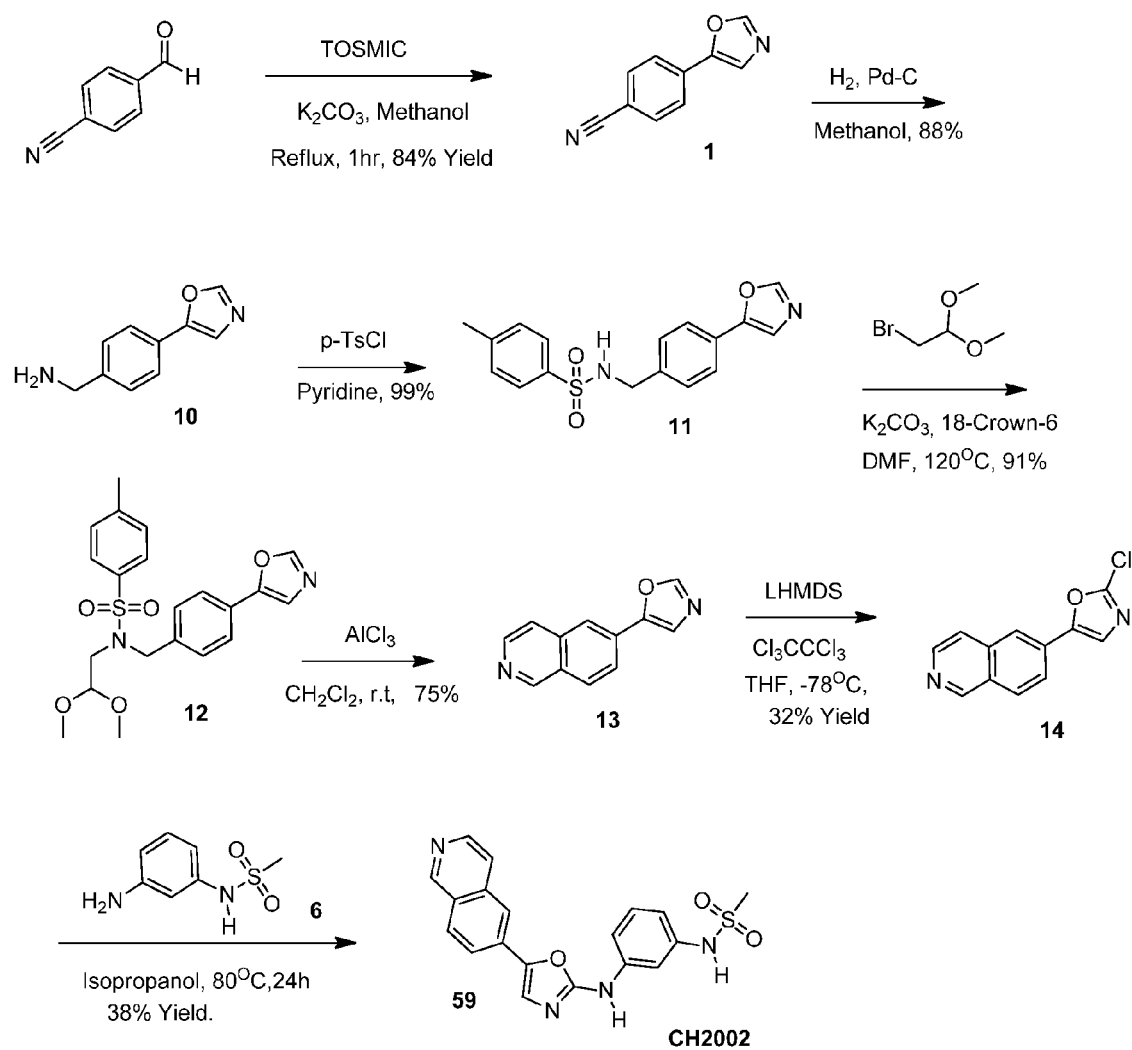
FIG. 40 depicts an exemplary synthetic route for the preparation of a compound of the invention.

The general synthetic scheme for CH2002 (compound 59) is found in FIG. 40. Compound 1, compound 10, compound 11, compound 12, compound 13, and compound 14 were prepared as described above.

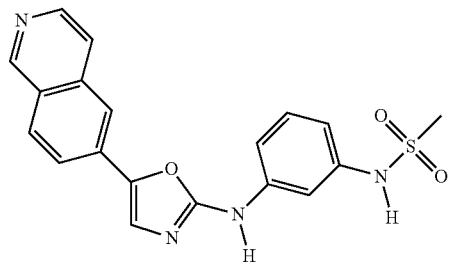 [SMILES: CS(=O)(=O)Nc1cccc(Nc2ncc(-c3ccc4cnccc4c3)o2)c1]

Compound 59: N-(3-((5-(isoquinolin-6-yl)oxazol-2-yl)amino)phenyl)methanesulfonamide A mixture of 2-chloro-5-(isoquinolin-6-yl)oxazole 14 (0.15 g, 0.652 mmol) and commercially available N-(3-aminophenyl)methanesulfonamide 6 (0.121 g, 0.649 mmol) in 2-propanol (20 mL) was heated to 80° C. for 12 h with stirring. Additional one more equivalent of N-(3-aminophenyl)methanesulfonamide 6 (0.121 g, 0.649 mmol) was added to reaction mixture and heated to 80° C. for further 12 h with stirring. Upon cooling, solvent was evaporated and silica column purified (Biotage) (Acetone/hexane as an eluent) to provide N-(3-((5-(isoquinolin-6-yl)oxazol-2-yl)amino)phenyl)methane sulfonamide 59 (0.09 g, 38% yield) as pale yellow solid. MS (ES) m/z 381 (M+H$^+$).

Example 21

Anti-Tumor Activity in COLO-205 and MDA-MB-468 Xenograft Mouse Models

The purpose of this study was to evaluate and compare the anti-tumor efficacy of the test article, Neos 518, in the MDA- MB-468 and COLO-205 Xenograft model. This study was divided into 2 parts based on the type of tumor models: a Colon cancer model (COLO-205 cells) and a breast cancer model (MDA-MB-468 cells). Tumors were established by inoculating BALB/c nu/nu mice with $5\times10^6$ of COLO-205 cells or $10\times10^6$ of MDA-MB-468 cells. Almost all of the animals developed palpable tumors. Tumors were measured approximately two times a week in order to determine their growth.

Animals inoculated with COLO-205 cells and with palpable tumors, were divided into two groups consisting of 5 animals per group. Group 1 was treated with vehicle and Group 2 was treated with Neos 518 (20 mg/kg).

Animals inoculated with MDA-MB-468 and with palpable tumors were divided into two groups consisting of 5 animals per group. Group 1 was treated with vehicle and Group 2 was treated with Neos 518 (20 mg/kg).

Control and test articles were administered via oral gavage every day, five times a week for two weeks. The body weight and tumor weights were recorded twice a week. After completion of the final dosing, the animals were observed for two additional weeks to monitor re-growth of the tumors. No remarkable changes in the body weight of mice in both studies were observed during the study.

In the COLO-205 xenograft models treated with Neos 518, a significant reduction in tumor volume as compared to control group was observed on Day 13 and this trend continued until the end of the study. A complete regression in tumor volume was not observed following dosing with Neos 518. However, no tumor re-growth was observed in any animals two weeks after the completion of dosing in Neos 518 treated animals In the MDA-MB-468 xenograft models, the animals were dosed every day, five times a week for two weeks and then observed for two weeks. A significant reduction in the tumor volume as compared to control group was observed on Day 7 and this trend continued until the end of the study. There was also a significant reduction in tumor volume on Day 7 and onwards as compared to the tumor volume on Day 1 in Neos 518 treated groups. No tumor re-growth was observed in any animals two weeks after the completion of dosing in Neos 518 treated animals.

Purpose

The purpose of the study was to determine anti-tumor efficacy of Neos 518 in COLO-205 and MDA-MB-468 Xenograft mouse models.

REFERENCES

The study was conducted based upon the following references:
ISO/IEC 17025, 2005, General Requirements for the Competence of Testing and Calibration Laboratories.
Sponsor Specifications
Identification of Test and Control Articles
Test Article:
Test Article Name: Neos 518
Physical Description: yellow powder
Storage Conditions: 2-8° C.
Vehicle Control (Sponsor Supplied):
Control Article Name: DMSO:PEG 300:Tween 80:PBS (5:15:2:18) in water
Physical Description Clear, colorless liquid
Storage Conditions Room Temperature
Identification of Test System Animals Used in the Study:
Species: BALB/c nu/nu mice
Sex: female (non-pregnant and nulliparous)
Weight/Age Range: 16.7-20.4 g, 5-6 weeks old weighed to the nearest 0.1 g
Health Status: healthy, not previously used in other experimental procedures
Animal Purchase: registered commercial breeder
Animal Identification: ear tag/tail marking
Acclimation: minimum 5 days, under same conditions as for the actual test
Animal Selection: selected from larger pool and examined to ensure lack of adverse clinical signs
Animal Care and Maintenance:
Animal Room Temperature: 68±5° F.
Animal Room Relative Humidity: 30-70%
Air Exchanges per Hour: a minimum of 10 changes per hour
Lights: 12-hour light/dark cycle, full spectrum fluorescent lights
Housing: group housed in ventilated micro-isolator cages
Cages: polycarbonate
Bedding: autoclaved laboratory grade bedding (contact)
Animal Rations: commercial rodent ration, ad libitum (irradiated pellets)
Water: autoclaved water, ad libitum
There were no known contaminants present in the feed, water, or bedding expected to interfere with the test data.
The laboratory and animal rooms are maintained as limited-access facilities.
Justification of Test System BALB/c nu/nu mice were used in this study because they have historically been used in xenograft studies to test anti-tumor efficacy of drug candidates.

Results:

The cell lines (COLO-205 and MDA-MB-468) were obtained from ATCC and cultured according to recommended specifications. Cells from a cell suspension were counted using the Trypan-blue viability test using a hemocytometer. Cell counts in quadrants of the hemocytometer were converted to a cells/mL value which enabled isolation of the appropriate number of cells per animal. Each animal was inoculated subcutaneously in the right flank region (for COLO-205 cells) or near mammary fat pad (for MDA-MB-468 cells) with 0.2 mL of a 50% RPMI/50% Matrigel™ mixture containing a suspension of tumor cells. For COLO-205, the mice were injected with approximately $5\times10^6$ cells. For MBA-MB-468, the mice were injected with approximately $10\times10^6$ cells.

Tumors were observed twice weekly until well established. Tumor weight was calculated using the formula: Tumor volume $(mm^3)=(a\times b^2/2)$ where 'b' is the smallest diameter and 'a' is the largest diameter in millimeters.

Once the established tumors reached a mean calculated volume of approximately 100 $mm^3$, the animals were randomized, using tumor weight, into treatment groups in order to reduce the variability of tumor sizes per group.

Following treatment, tumor and mouse body weight measurement were recorded twice weekly and gross observations were made at least once daily.

Figure 58:
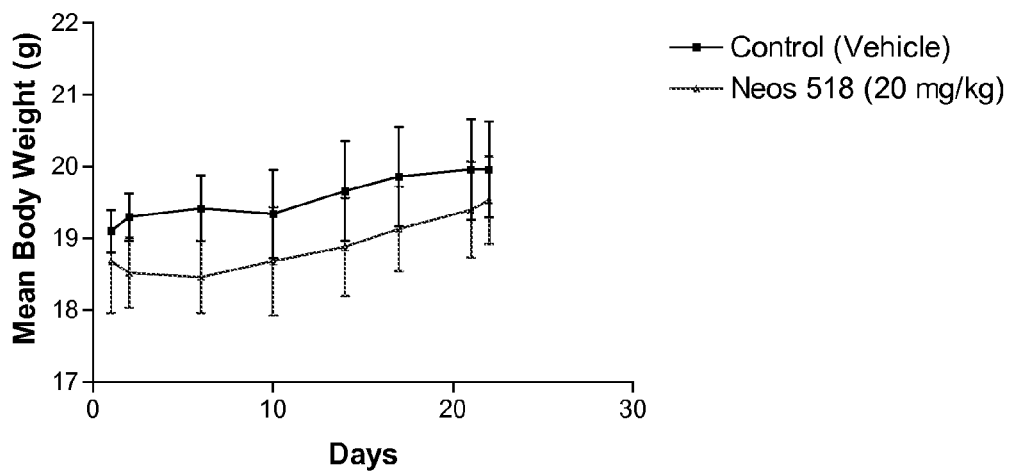
FIG. 58 depicts the effect of a compound of the invention (Neos 518) on body weights of mice in the (a) MBA-MB-468 and (b) COLO-205 tumor models. No remarkable changes in the body weight of mice in both studies were observed during the study.
Figure 58:
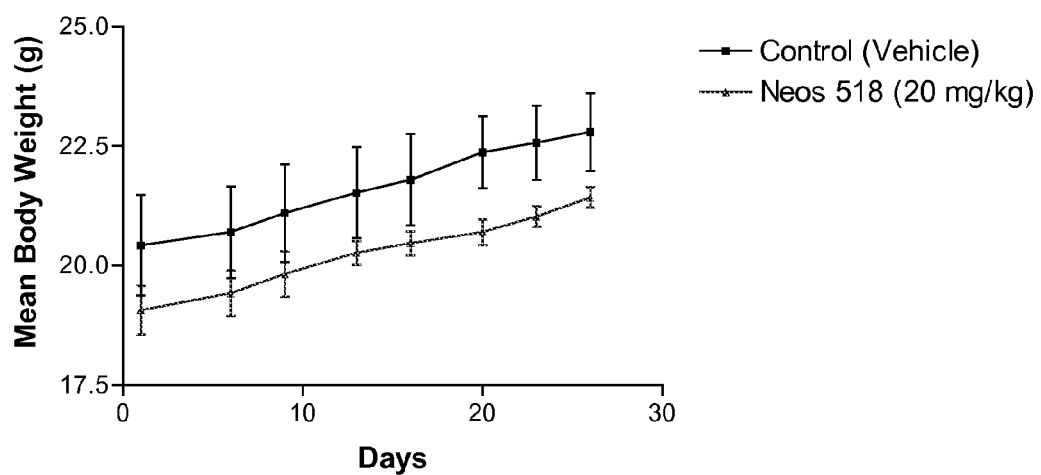
Figure 59:
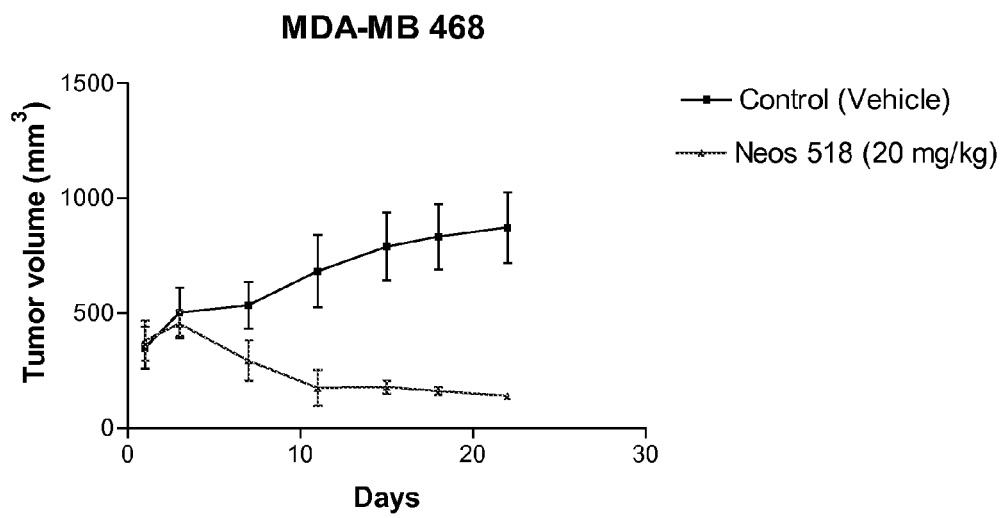
FIG. 59 depicts the effect of a compound of the invention (Neos 518) on tumor volume of mice in the MBA-MB-468 tumor model. A significant reduction in the tumor volume as compared to control group was observed on Day 7 and this trend continued until the end of the study. There was also a significant reduction in tumor volume on Day 7 and onwards as compared to the tumor volume on Day 1 in Neos 518 treated groups. No tumor re-growth was observed in any animals two weeks after the completion of dosing in Neos 518-treated animals.
Figure 60:
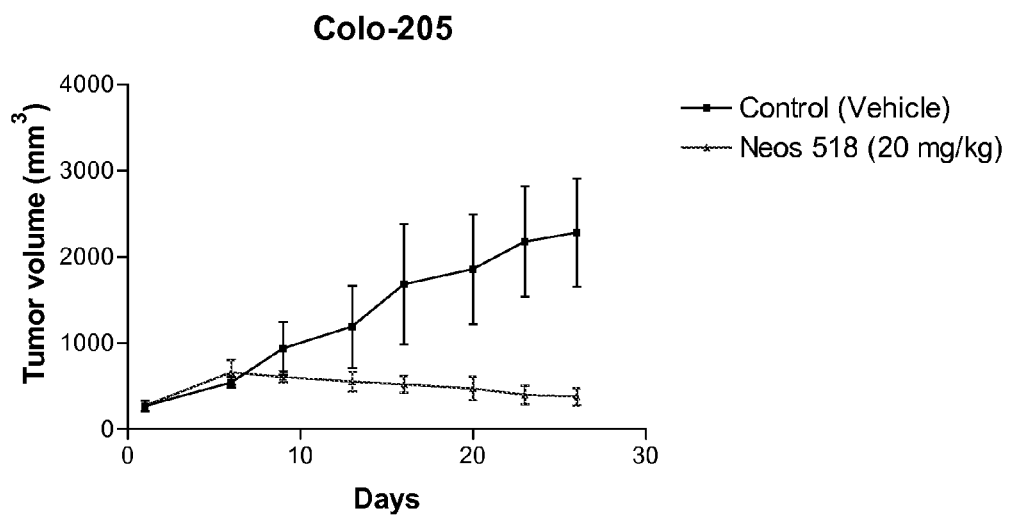
FIG. 60 depicts the effect of a compound of the invention (Neos 518) on tumor volume of mice in the COLO-205 tumor model. A significant reduction in tumor volume as compared to control group was observed on Day 13 and this trend continued until the end of the study. A complete regression in tumor volume was not observed following dosing with Neos 518. However, no tumor re-growth was observed in any animals two weeks after the completion of dosing in Neos 518-treated animals.

See FIGS. 58, 59, and 60.

Example 22

Pharmacokinetic Analysis of Compound 223 after a Single Oral Dose in Male ICR Mice Study Summary The objective of this study is to evaluate PK parameters of Neos 223 after a single oral dose of male ICR mice. The animals were treated with 20 mg/kg of Neos 223 on Day 1.

Blood samples were collected into $K_3$ EDTA containing tubes at pre-dose (0 h), and 0.25, 0.5, 1, 2, 4, 6, 8, 24, and 48 h post-dose via cardiac puncture after sacrifice.

The PK analysis was performed using WinNonlin™ software v5.2[2]. A non-compartmental analysis was performed using NCA model 202 for PK parameter determination.

AUC values were calculated using the linear/log trapezoidal method. The terminal rate constant of elimination ($\lambda_z$) of Neos 223 was calculated with a best fit linear regression.

Figures 63, 64:
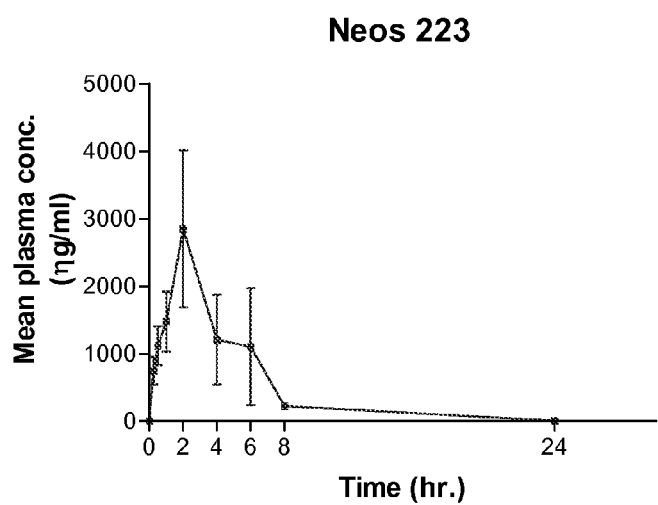
FIG. 63 depicts the mean plasma concentration of a compound of the invention (Compound 223) after single oral dosing in male ICR mice.
FIG. 64 tabulates the pharmacokinetic profile of a compound of the invention (Compound 223).

See FIG. 61 for a table outlining the design of the study.
Identification of Test and Control Articles/Formulations
Test Article Name: Neos 223
Batch Number: 2012B
Physical Description: white solid
Storage Conditions: 4° C.
Stability: Stable
Safety Precautions: Standard Laboratory Safety Precautions
Identification of Test System
  Number of Animals and Species: 30 ICR mice
  Sex: Male
  Weight/Age Range: approximately 20-25 g, weighed to the nearest 0.1 g, approximately 5-6 weeks old
  Health Status Healthy, previously unused in other experimental procedures.
  Acclimatization: At least 5 days before treatment
Results
  See FIGS. 62-64 for the mean concentration of Compound 223 after single oral dosing in male ICR mice, and for the resulting pharmacokinetic profile.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound of Formula III

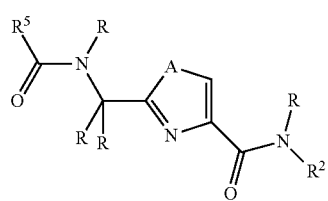

III wherein, independently for each occurrence, $R^2$ is substituted or unsubstituted aryl or substituted or unsubstituted heteroaryl;
A is —O—, —S—, or —NR—;
R is —H, or alkyl; and
$R^5$ is substituted or unsubstituted heteroaryl.

2. The compound of claim 1, wherein $R^2$ is

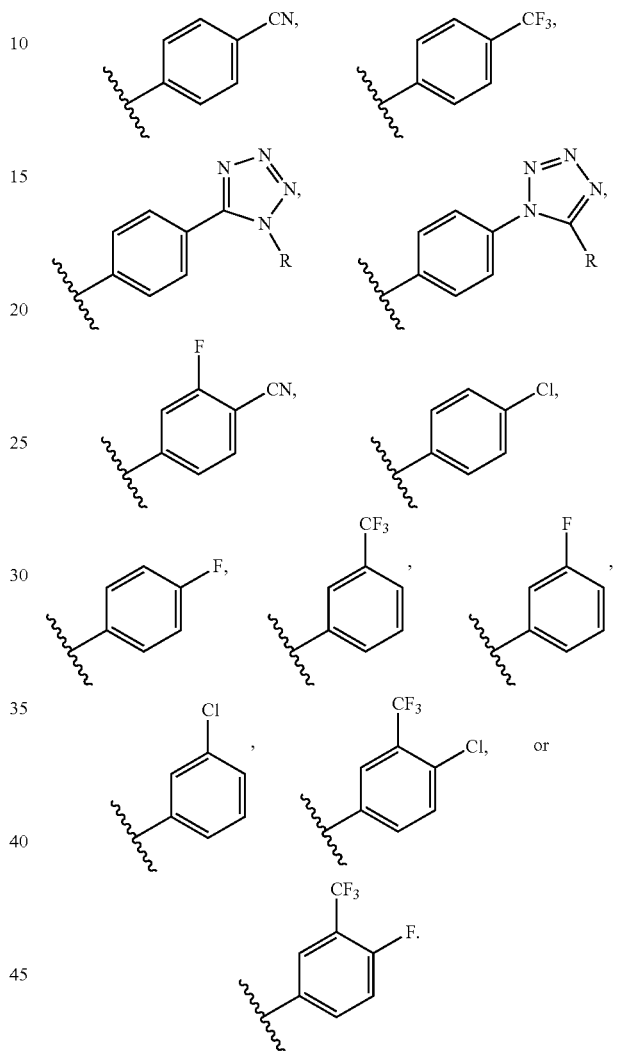

3. The compound of claim 1, wherein A is —O— or —S—.
4. The compound of claim 1, wherein $R^5$ is

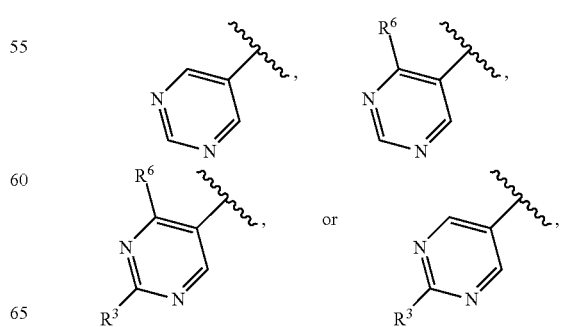

$R^3$ is —H, —OR$^4$, —NR$_2$, or halo; $R^6$ is halo, alkyl, haloalkyl, —OR$^4$, or —NR$^2$; and $R^4$ is —H, alkyl, or —(CR$_2$CR$_2$—O—)$_x$—R.

5. The compound of claim 1, having the following structure:

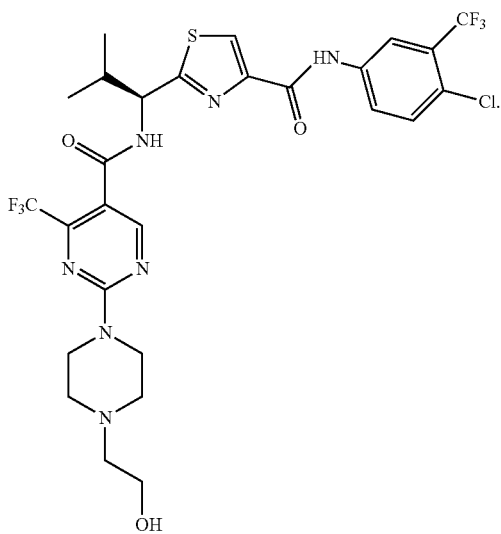 [SMILES: CC(C)[C@H](NC(=O)c1cnc(N2CCN(CCO)CC2)nc1C(F)(F)F)c1nc(C(=O)Nc2ccc(Cl)c(C(F)(F)F)c2)cs1]

6. A method of therapeutically treating cancer, comprising administering to a mammal in need thereof a therapeutically effective amount of a compound of claim 1, wherein the cancer is mediated by an abnormal increase in activity of CDK2, CDK4, or VEGFR2.

7. A method of inhibiting CDK2, CDK4, or VEGFR2 in a cell, comprising contacting the cell with an effective amount of a compound of claim 1.

8. A method of treating a disease, comprising administering to a mammal having said disease a therapeutically effective amount of a compound of claim 1, wherein the disease is characterized by cellular proliferation; the disease is mediated by an abnormal increase in activity of CDK2, CDK4, or VEGFR2; and the disease is associated with neo-vascularization or vascular permeability.

9. The method of claim 8, wherein the disease is selected from the group consisting of: blood vessel proliferative disorders, including arthritis and restenosis; fibrotic disorders, including hepatic cirrhosis and atherosclerosis; mesangial cell proliferative disorders, including glomerulonephritis, diabetic nephropathy, malignant nephrosclerosis, thrombotic microangiopathy syndromes, proliferative retinopathies, organ transplant rejection, and glomerulopathies; and metabolic disorders, including psoriasis, diabetes mellitus, chronic wound healing, inflammation, and neurodegenerative diseases.

10. A method of therapeutically treating cancer, comprising administering to a mammal in need thereof a therapeutically effective amount of the compound of claim 5, wherein the cancer is mediated by an abnormal increase in activity of CDK2, CDK4, or VEGFR2.

11. A method of inhibiting CDK2, CDK4, or VEGFR2 in a cell, comprising contacting the cell with an effective amount of the compound of claim 5.

12. A method of treating a disease, comprising administering to a mammal having said disease a therapeutically effective amount of the compound of claim 5, wherein the disease is characterized by cellular proliferation; the disease is mediated by an abnormal increase in activity of CDK2, CDK4, or VEGFR2; and the disease is associated with neo-vascularization or vascular permeability.

13. The method of claim 12, wherein the disease is selected from the group consisting of: blood vessel proliferative disorders, including arthritis and restenosis; fibrotic disorders, including hepatic cirrhosis and atherosclerosis; mesangial cell proliferative disorders, including glomerulonephritis, diabetic nephropathy, malignant nephrosclerosis, thrombotic microangiopathy syndromes, proliferative retinopathies, organ transplant rejection, and glomerulopathies; and metabolic disorders, including psoriasis, diabetes mellitus, chronic wound healing, inflammation, and neurodegenerative diseases.

14. A compound of Formula III

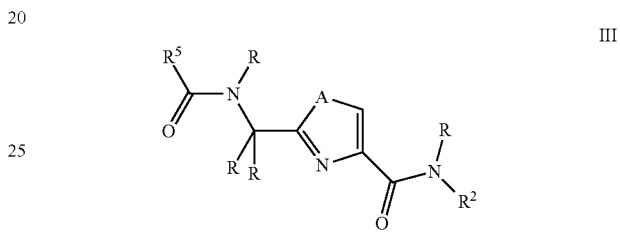

wherein, independently for each occurrence, $R^2$ is

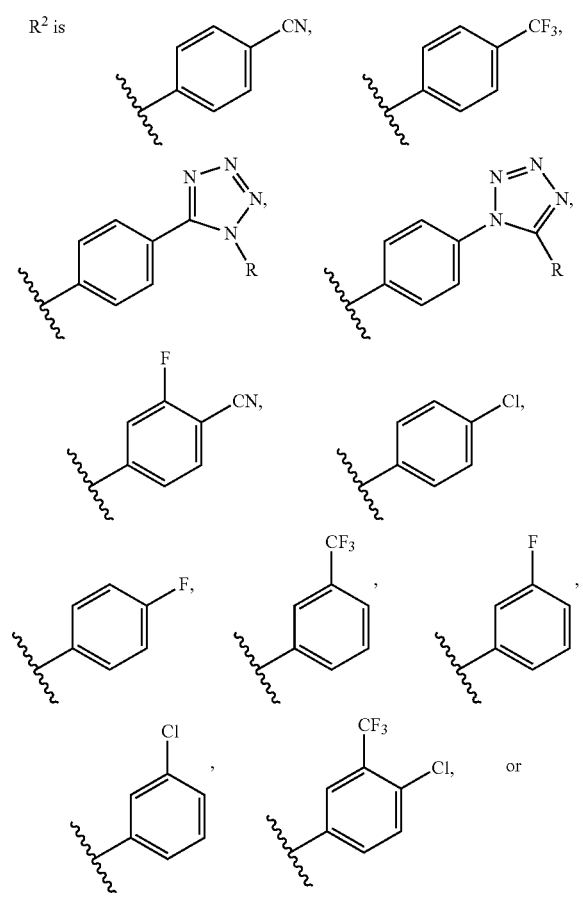

-continued

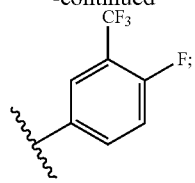

A is —S—;
R is —H or alkyl; and
R⁵ is substituted pyrimidinyl.

15. The compound of claim 14, wherein R² is

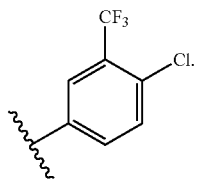 [SMILES: *c1ccc(Cl)c(C(F)(F)F)c1]

16. The compound of claim 14, wherein R is —H or isopropyl.

17. The compound of claim 14, wherein R⁵ is

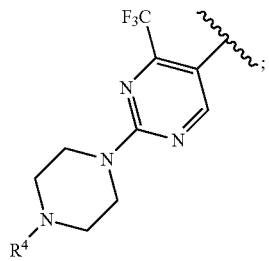

and R⁴ is —H, alkyl, or —(CR₂CR₂—O—)ₓ—R.

18. The compound of claim 14, wherein R⁵ is

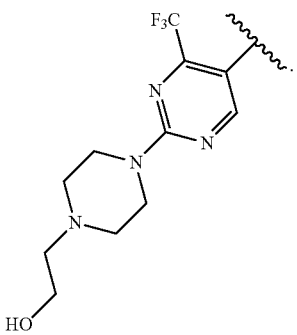

19. A method of therapeutically treating cancer, comprising administering to a mammal in need thereof a therapeutically effective amount of a compound of claim 14, wherein the cancer is mediated by an abnormal increase in activity of CDK2, CDK4, or VEGFR2.

20. A method of inhibiting CDK2, CDK4, or VEGFR2 in a cell, comprising contacting the cell with an effective amount of a compound of claim 14.

21. A method of treating a disease, comprising administering to a mammal having said disease a therapeutically effective amount of a compound of claim 14, wherein the disease is characterized by cellular proliferation; the disease is mediated by an abnormal increase in activity of CDK2, CDK4, or VEGFR2; and the disease is associated with neo-vascularization or vascular permeability.

22. The method of claim 21, wherein the disease is selected from the group consisting of: blood vessel proliferative disorders, including arthritis and restenosis; fibrotic disorders, including hepatic cirrhosis and atherosclerosis; mesangial cell proliferative disorders, including glomerulonephritis, diabetic nephropathy, malignant nephrosclerosis, thrombotic microangiopathy syndromes, proliferative retinopathies, organ transplant rejection, and glomerulopathies; and metabolic disorders, including psoriasis, diabetes mellitus, chronic wound healing, inflammation, and neurodegenerative diseases.

* * * * *

UNITED STATES PATENT AND TRADEMARK OFFICE
CERTIFICATE OF CORRECTION

PATENT NO.      : 8,546,400 B2              Page 1 of 1
APPLICATION NO. : 13/737328
DATED           : October 1, 2013
INVENTOR(S)     : Laxman S. Desai et al.

It is certified that error appears in the above-identified patent and that said Letters Patent is hereby corrected as shown below:

On the Title Page: Item 54 and in the Specification: Col. 1, Line 1 the title should read as follows:

1,3-Oxazole-4-Carboxamides, 1,3-Thiazole-4-Carboxamides, and 1,3-Imidazole-4-Carboxamides as Inhibitors of Cyclin Dependent Kinases Signed and Sealed this
Third Day of December, 2013

Margaret A. Focarino
*Commissioner for Patents of the United States Patent and Trademark Office*